(12) United States Patent
Kharul et al.

(10) Patent No.: US 8,835,469 B2
(45) Date of Patent: Sep. 16, 2014

(54) SUBSTITUTED BENZAMIDE DERIVATIVES AS GLUCOKINASE (GK) ACTIVATORS

(75) Inventors: Rajendra Kharul, Ahmedabad (IN); Mukul R. Jain, Ahmedabad (IN); Pankaj R. Patel, Ahmedabad (IN)

(73) Assignee: Cadila Healthcare Limited, Gujarat (IN)

( * ) Notice: Subject to any disclaimer, the term of this patent is extended or adjusted under 35 U.S.C. 154(b) by 177 days.

(21) Appl. No.: 13/387,885

(22) PCT Filed: Jul. 22, 2010

(86) PCT No.: PCT/IN2010/000486
§ 371 (c)(1),
(2), (4) Date: Apr. 3, 2012

(87) PCT Pub. No.: WO2011/013141
PCT Pub. Date: Feb. 3, 2011

(65) Prior Publication Data
US 2012/0184544 A1 Jul. 19, 2012

(30) Foreign Application Priority Data
Jul. 31, 2009 (IN) .......................... 1767/MUM/2009

(51) Int. Cl.
| | | |
|---|---|---|
| C07D 413/14 | (2006.01) | |
| C07D 417/12 | (2006.01) | |
| C07D 417/14 | (2006.01) | |
| A61K 31/497 | (2006.01) | |
| A61K 31/428 | (2006.01) | |
| A61K 31/496 | (2006.01) | |

(52) U.S. Cl.
USPC ........... 514/360; 514/361; 514/363; 548/131; 548/139; 548/143

(58) Field of Classification Search
USPC ........... 548/131, 139, 143; 514/360, 361, 363
See application file for complete search history.

(56) References Cited

FOREIGN PATENT DOCUMENTS

| | | |
|---|---|---|
| EP | 1600442 | 11/2005 |
| WO | WO2008050010 | 5/2008 |

OTHER PUBLICATIONS

Sarabu R. et al.: "Glucokinase activators as new type 2 diabetes therapeutic agents". Expert Opinion on Therapeutic Patents, 2008, 18(7), 759-768.
International Search Report of PCT/IN2010/000486, dated: Jan. 25, 2011.
International Preliminary Report on Patentability of PCT/IN2010/000486, dated: Jul. 13, 2011.

*Primary Examiner* — Kahsay Habte
(74) *Attorney, Agent, or Firm* — McCarter & English, LLP; Steven G. Davis; Wei Song

(57) ABSTRACT

The present invention relates to substituted benzamide derivatives of the Formula I and their pharmaceutically acceptable salts, pharmaceutically acceptable solvates, enantiomers, diastereomers, prodrugs, metabolites, and polymorphs and can be useful for treating disease states mediated by glucokinase. Compounds disclosed herein can be used for reducing blood glucose levels and for increasing insulin secretion for treating type II diabetes. The invention also relates to processes for the preparation of the compounds of invention, pharmaceutical compositions containing the compounds, and their use.

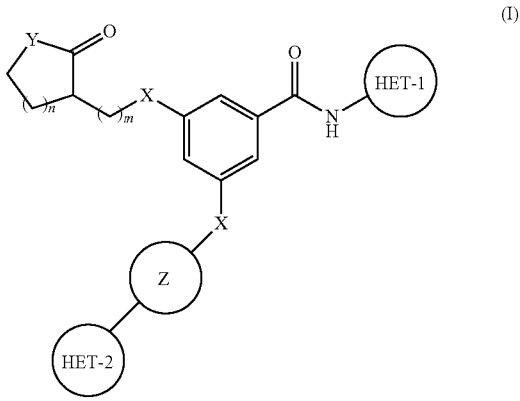

(I)

14 Claims, No Drawings

SUBSTITUTED BENZAMIDE DERIVATIVES AS GLUCOKINASE (GK) ACTIVATORS

RELATED APPLICATIONS

This application is a 35 U.S.C. § 371 national stage filing of International Application No. PCT/IN2010/000486, filed Jul. 22, 2010, which claims priority under 35 U.S.C. § 119 to India Patent Application Ser. No. 1767/MUM/2009, filed Jul. 31, 2009. The entire contents of each of the aforementioned applications are incorporated herein by reference in their entirety.

FIELD OF THE INVENTION

The present invention relates to substituted benzamide derivatives and their pharmaceutically acceptable salts, pharmaceutically acceptable solvates, enantiomers, diastereomers, prodrugs, metabolites, and polymorphs, and can be useful for treating disease states mediated by glucokinase. Compounds disclosed herein can be used for reducing blood glucose levels and for increasing insulin secretion for treating type II diabetes. The invention also relates to processes for the preparation of the compounds of invention, pharmaceutical compositions containing the compounds, and their use.

BACKGROUND OF THE INVENTION

Glucokinase (GK) also referred as hexokinase IV or hexokinase D and belongs to the family of hexokinases. It catalyzed phosphorylation of hexoses such as D-glucose, D-mannose, D-fructose and 2-deoxy-D-glucose by $MgATP^{2-}$. (Cardenas, M. L. et. al., *Biochim. Biophys. Acta*, 1401, 242-264 (1998)). Glucokinase differs from other hexokinases in terms of its enzyme kinetics. It has positive co-operativity and low affinity for glucose. In contrast to other hexokinases, it does not get inhibited by its end product, glucose-6-phosphate.

Glucokinase is principally expressed in liver and pancreatic β-cells. The glucose concentration at which glucokinase exhibits half maximum activity is 8 mM. The other three hexokinases get saturated at very low glucose concentration (<1 mM). Therefore, the flux of glucose through GK pathway rises as the concentration of glucose in the blood increases from fasting (5 mM) to postprandial (~10 mM) levels following carbohydrate containing meal [Printz, R. G., Magnuson, M. A. and Granner, D. K. in *Ann. Rev. Nutrition*, vol. 13, (R. E. Olson, D. M. Bier, and D. B. McCormik, eds.) Annual Review Inc. Palo Alto, Calif, pages 463-496, 1993]. A decade ago, these and subsequent findings led to the hypothesis that GK functions as glucose sensor in hepatocyte and pancreatic β-cells. (Meglasson, M. D. et. al. *Amer. J. Physiol.*, 246, E1-E13, 1984).

Recently, transgenic animal study has confirmed that GK does play a critical role in whole-body glucose-homeostasis. Animals those do not express GK die within few days of birth with severe diabetes while animals with GK overexpression have improved glucose tolerance [Grupe, A. et. al. *Cell*, 83, 69-78, (1995); Ferrie, T. et. al. *FASEB J.*, 10, 1213-1218, (1996)].

There are both, activating and deactivating mutations reported for GK gene. Deactivating mutations cause diabetes called type 2 maturity onset diabetes of young (MODY2) (Vionnet, N., et. al., *Nature*, 356, 721-22, (1992); Matschinsky, F. M., et. al. *J. Clin. Invest*. 92, 2092-98, (1993)) while activating mutations cause persistent hyperinsulinemic hypoglycemia of infancy (PHHI) (Christesen, H. B. et. al., *Diabetes,* 51, 1240-46, (2002)). These literature data supports the notion that small molecules as glucokinase activators will help to treat diabetes particularly type II diabetes.

International (PCT) Patent Publication No. WO 01/44216 discloses 2, 3-disubstituted trans olefin N-heteroaromatic or urido proprionamides as glucokinase activators which increase insulin secretion in the treatment of type II diabetes. U.S. Patent No. US2003/0225286 discloses hydantoin compounds which are active as glucokinase activators and useful to increase insulin secretion for treating type II diabetes. European Patent Publication No. EP 1305301 discloses alpha-acyl & alpha-heteroatom-substituted benzene acetamide as glucokinase activators. International (PCT) Patent Publication No. WO2005/080359 discloses benzamide derivatives and their use as glucokinase activating agents. International (PCT) Patent Publication No. WO2005/080360 discloses benzamide derivatives as glucokinase activators. International (PCT) Patent Publication No. WO2005/121110 discloses heteroaryl benzamide derivatives for use as glucokinase activators in the treatment of diabetes. International (PCT) Patent Publication No. WO 2006/040528 discloses phenoxy benzamide compounds with utility in the treatment of type II diabetes and obesity. International (PCT) Publication No. WO 2007/007042 describes heteroaryl benzamide derivatives for use as glucokinase activators in the treatment of diabetes. International (PCT) Publication No. WO 2008/050101 describes chemical compounds which may be useful in the treatment or prevention of a disease or medical condition mediated through glucokinase such as type 2 diabetes.

However, the therapeutic potential of these compounds to treat diseases has not yet been proved and so there remains the need to develop newer medicines which are better or of comparable efficacy with the present treatment regimes, have lesser side effects and require a lower dosage regime.

We herein disclose novel compounds of general Formula (I) which are glucokinase activators and are useful for the prevention and treatment of disease states mediated by Glucokinase (GK).

SUMMARY OF THE INVENTION

In one aspect there are provided novel substituted benzamide derivatives represented by the general Formula (I),

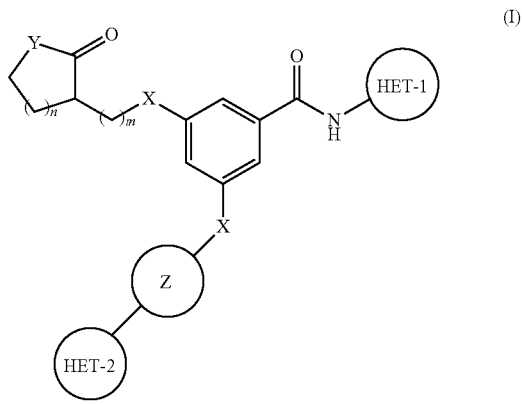

and their pharmaceutically acceptable salts, pharmaceutically acceptable solvates, enantiomers, diastereomers, prodrugs, metabolites, and polymorphs.

In another aspect of the invention there are provided processes for the preparation of compounds represented by the general Formula (I), and their pharmaceutically acceptable salts, pharmaceutically acceptable solvates, enantiomers, diastereomers, prodrugs, metabolites, and polymorphs.

In another aspect of the invention there are provided pharmaceutical compositions containing compounds of the general Formula (I), or their pharmaceutically acceptable salts, pharmaceutically acceptable solvates, enantiomers, diastereomers, prodrugs, metabolites, or polymorphs, in combination with suitable carriers, excipients, or diluents or other media normally employed in preparing such compositions, which can be used for the prevention and treatment of disease states mediated by Glucokinase (GK).

The details of one or more embodiments of the inventions are set forth in the description below. Other features, objects and advantages of the inventions will be apparent from the description.

DESCRIPTION OF THE INVENTION

Accordingly, the present invention relates to compounds of the general Formula (I),

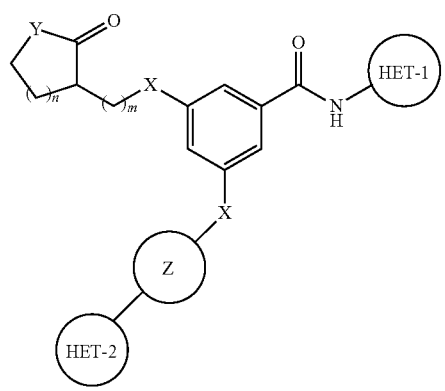

and their pharmaceutically acceptable salts, pharmaceutically acceptable solvates, enantiomers, diastereomers, prodrugs, metabolites, polymorphs, and pharmaceutical compositions containing them, wherein X=O, $CH_2$, S; Y=O, $CH_2$, $CR^1R^2$, $NR^1$, $NCOR^1$; HET-1 is a 5- or 6-membered, C-linked heteroaryl ring containing a nitrogen atom in 2-position relative to the amide nitrogen to which the ring is attached and optionally containing 1 or 2 further ring heteroatoms independently selected from O, N and S, which ring is optionally substituted with one or more $R^3$; Ring 'Z' is selected from phenyl or 'HET-3', wherein 'HET-3' is a 5- or 6-membered heteroaryl or heterocyclic ring containing 1, 2 or 3 heteroatoms independently selected from O, S and N and wherein either the phenyl or the 'HET-3' independently is further substituted with one or more of $R^3$; 'HET-2' is a 4-, 5- or 6-membered, C- or N-linked heteroaryl or heterocyclyl ring containing 1, 2, 3 or 4 heteroatoms independently selected from O, S and N & wherein further one of the —$CH_2$ groups in the ring can be optionally replaced with a —C(O) group, the sulfur atom when present in the heterocyclic ring may optionally be oxidized to a S(O) or S(O)$_2$ group, and wherein the 'HET-2' is further optionally substituted on any of the available atom with one or more $R^3$; $R^3$ at each occurance is independently selected from hydrogen, halogen, cyano, optionally substituted groups selected from —$NR^1R^2$, $C_{(1-6)}$ alkyl, $C_{(2-6)}$alkenyl, $C_{(2-6)}$alkyne, $C_{(1-6)}$ haloalkyl, $C_{(1-6)}$ alkoxy, $C_{(1-6)}$ haloalkoxy, $C_{(3-6)}$ cycloalkyl, —$(CH_2)_p$—$COOR^1$, —$(CH_2)_p$—$CONR^1R^2$, $CONHR^1$, perfluoroalkyl, $C_{(1-4)}$ alkoxyalkyl, aryl, arylalkyl, amino, aminoalkyl, alkylamino, alkylaminoalkyl, alkyl$C_{(1-4)}$alkoxy, wherein each of $R^3$ when further substituted, the substituents are independently selected from amino, halo, cyano, nitro, hydroxyl, alkoxy groups; and $R^1$ and $R^2$ at each occurrence is independently selected from hydrogen, halogen, amino, cyano, nitro, optionally substituted groups selected from $C_{(1-4)}$ alkyl, $C_{(2-4)}$ alkenyl, $C_{(2-4)}$ alkynyl, $C_{(1-4)}$ alkoxy, $C_{(1-4)}$ haloalkyl groups or alternatively, when possible, $R^1$ & $R^2$ together with the atom to which they are attached may further form a cycloalkyl or heterocyclic ring containing heteroatoms selected from O, S and N; m=0, 1, 2; n=0, 1, 2; o=0, 1, 2; p=0, 1, 2.

In one embodiment there are provided compounds, wherein 'HET'-1 is a 5- or 6-membered, C-linked heteroaryl ring containing a nitrogen atom in 2-position relative to the amide nitrogen to which the ring is attached, and optionally containing 1 or 2 further ring heteroatoms independently selected from O, N and S, which ring is optionally substituted with one or more $R^3$; ring 'Z' is phenyl, substituted with 1 to 3 substituents selected from $R^3$; X=O, $CH_2$, S; Y=O, $CH_2$, $CR^1R^2$, $NR^1$, $NCOR^1$; and $R^3$, $R^1$, $R^2$, m, m, o, p, and 'HET-2' are as defined earlier.

In another embodiment there are provided compounds, wherein 'HET-1' is a 5- or 6-membered, C-linked heteroaryl ring containing a nitrogen atom in 2-position relative to the amide nitrogen to which the ring is attached, and optionally containing 1 or 2 further ring heteroatoms independently selected from O, N and S, which ring is optionally substituted with one or more $R^3$; ring 'Z' represents 'HET-3', optionally substituted with 1 to 3 substituents selected from $R^3$; X=O, $CH_2$, S; Y=O, $CH_2$, $CR^1R^2$, $NR^1$, $NCOR^1$; and $R^3$, $R^1$, $R^2$, m, m, o, p, and 'HET-2' are as defined earlier.

In yet another embodiment there are provided compounds, wherein 'HET-1' is a 5- or 6-membered, C-linked heteroaryl ring containing a nitrogen atom in 2-position relative to the amide nitrogen to which the ring is attached and optionally containing 1 or 2 further ring heteroatoms independently selected from O, N and S, which ring is optionally substituted with one or more $R^3$; ring 'Z' is phenyl, substituted with 1 to 3 substituents selected from $R^3$; X=O, $CH_2$, S; Y=O, $CH_2$, $CR^1R^2$, $NR^1$, $NCOR^1$; $R^3$, $R^1$, $R^2$, m, m, o, and p are as defined earlier; and 'HET-2' is selected from the following cyclic groups:

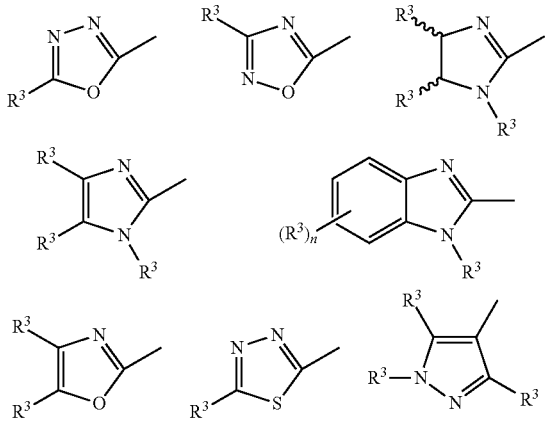

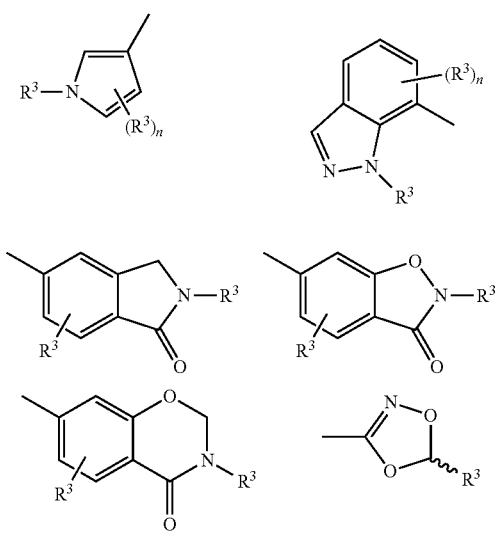

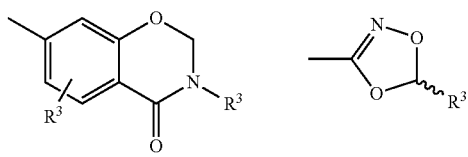

In still another embodiment there are provided compounds of Formula (I), wherein 'HET-1' is a 5- or 6-membered, C-linked heteroaryl ring containing a nitrogen atom in 2-position relative to the amide nitrogen to which the ring is attached and optionally containing 1 or 2 further ring heteroatoms independently selected from O, N and S, which ring is optionally substituted with one or more $R^3$; ring 'Z' represents 'HET-3', optionally substituted with 1 to 3 substituents selected from $R^3$; X=O, CH$_2$, S; Y=O, CH$_2$, CR$^1$R$^2$, NR$^1$, NCOR$^1$; $R^3$, $R^1$, $R^2$, m, m, o, and p are as defined earlier; and 'HET-2' is selected from the following cyclic groups:

In a further embodiment there are provided compounds of Formula (I), wherein X=O, CH$_2$; Y=O, CH$_2$, CR$^1$R$^2$; ring 'Z' represents phenyl, substituted with 1 to 3 substituents selected from $R^3$ and 'HET-1', 'HET-2', $R^1$, $R^2$, $R^3$, m, n, o, and p are as defined earlier.

In another embodiment there are provided compounds of Formula (I), wherein X=O, CH$_2$; Y=O, CH$_2$, CR$^1$R$^2$, NR$^1$; ring 'Z' represents phenyl, substituted with 1 to 3 substituents selected from $R^3$, wherein $R^3$ at each occurrence independently represents hydrogen, halo, C$_{(1-6)}$ alkyl, C$_{(2-6)}$alkenyl, and aryl, wherein when any of $R^3$ is further substituted, the substituents are selected from halo, nitro, hydroxyl, alkoxy groups; $R^1$ and $R^2$ at each occurrence is independently selected from hydrogen, halo, hydroxyl, cyano, C$_{(1-4)}$alkyl, C$_{(1-4)}$alkoxy, and; 'HET-1', 'HET-2', m, n, o, and p are as defined earlier.

In yet another embodiment there are provided compounds of Formula (I), wherein X=O, CH$_2$; Y=O, CR$^1$R$^2$, NR$^1$; ring Z is phenyl, substituted with 1 to 3 substituents selected from $R^3$, wherein $R^3$ at each occurrence independently represents hydrogen, halo, C$_{(1-6)}$alkyl groups; $R^1$ and $R^2$ at each occurrence is indepently selected from hydrogen, halo, hydroxyl, cyano, C$_{(1-4)}$alkyl, C$_{(1-4)}$alkoxy; m=0, 1; n=0, 1; o=0; p=0, 1; 'HET-1' is as defined earlier & 'HET-2' is selcted from but not limited to the following cyclic groups;

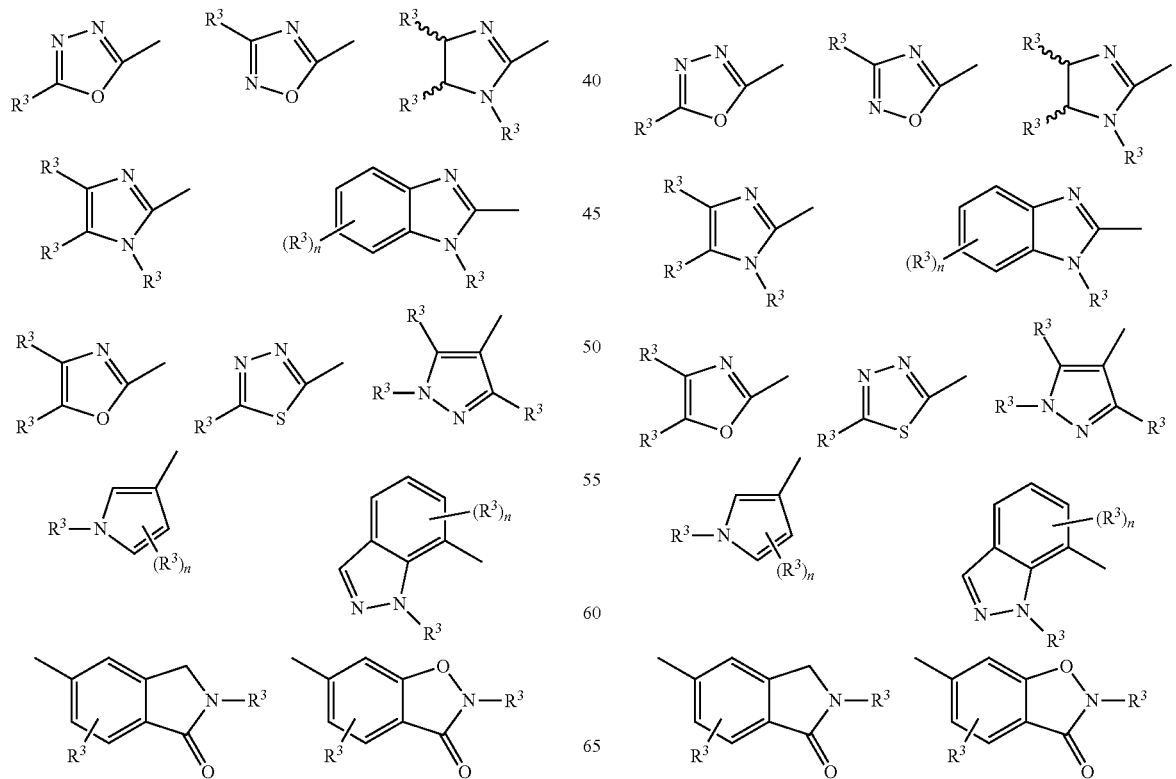

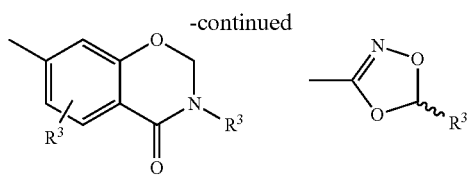

Various groups, radicals described above may be selected from:

"Alkyl", as well as other groups having the prefix "alk", such as alkoxy and alkanoyl, means carbon chain which may either be linear or branched, and combinations thereof, unless the carbon chain is defined otherwise. Examples of alkyl group include, but not limited to, methyl, ethyl, propyl, iso-propyl, butyl, sec-butyl, tert.-butyl, pentyl, hexyl etc. Where the specified number of carbon atoms permits e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Alkenyl" means carbon chains which contain at least one carbon-carbon double bond, and which may be linear or branched or combinations thereof, unless the carbon chain is defined otherwise. Examples of alkenyl include, but not limited to, vinyl, allyl, isopropenyl, hexenyl, pentenyl, heptenyl, 1-propenyl, 2-butenyl, 2-methyl-2-butenyl etc. Where the specified number of carbon atoms permits, e.g., from $C_{5-10}$, the term alkenyl also includes cycloalkenyl groups and combinations of linear, branched and cyclic structures. When no number of carbon atoms is specified, $C_{(2-6)}$ is intended.

"Alkynyl" means carbon chains which contain at least one carbon-carbon triple bond, and which may be linear or branched or combinations thereof. Examples of alkynyl include ethynyl, propargyl, 3-methyl-1-pentynyl etc. When no number of carbon atoms is specified, $C_{(2-6)}$ is intended.

"Cycloalkyl" is the subset of alkyl and means saturated carbocyclic ring having a specified number of carbon atoms, preferably 3-6 carbon atoms. Examples of cycloalkyl include cyclopropyl, cyclobutyl, cyclopentyl, cyclohexyl, cycloheptyl etc. A cycloalkyl group generally is monocyclic unless otherwise stated. Cycloalkyl groups are saturated unless and otherwise stated.

The "alkoxy" refers to the straight or branched chain alkoxides of the number of carbon atoms specified.

The term "alkylamino" refers to straight or branched alkylamines of the number of carbon atoms specified.

"Aryl" means a mono- or polycyclic aromatic ring system cotaining carbon ring atoms. The preffered aryls are monocyclic or bicyclic 6-10 membered aromatic ring systems. Phenyl and naphthyl are preferred aryls.

"Heterocycle" and "heterocyclyl" refer to saturated or unsaturated non-aromatic rings or ring systems containing at least one heteroatom selected from O, S, N further including the oxidized forms of sulfur, namely SO & $SO_2$. Examples of heterocycles include tetrahydrofuran (THF), dihydrofuran, 1,4-dioxane, morpholine, 1,4-dithiane, piperazine, piperidine, 1,3-dioxolane, imidazoline, imidazolidine, pyrrolidine, pyrroline, tetrahydropyran, dihydropyran, oxathiolane, dithiolane, 1,3-dioxane, 1,3-dithiane, oxathiane, thiomorpholine etc.

"Heteroaryl" means an aromatic or partially aromatic heterocycle that contains at least one ring heteroatom selected from O, S and N. Heteroaryls thus include heteroaryls fused to the other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl etc. For heterocyclyl and heteroaryl groups, rings and ring systems containing from 3-15 carbon atoms are included, forming 1-3 rings.

"Halogen" refers to fluorine, chlorine, bromine, iodine. Chlorine and fluorine are generally preferred.

Suitable groups and substituents on the groups may be selected from those described anywhere in the specification.

The term "substituted," as used herein, means that any one or more hydrogens on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

Particularly useful compounds may be selected from, but not limited to:

3-(4-(5-Methyl-1,3,4-oxadiazol-2-yl)phenoxy)-5-((1-methyl-2-oxopyrrolidin-3-yl)methoxy)-N-(thiazol-2-yl)benzamide;

3-(4-(5-Methyl-1,3,4-oxadiazol-2-yl)phenoxy)-5-((1-methyl-2-oxopyrrolidin-3-yl)methoxy)-N-(4-methylthiazol-2-yl)benzamide;

3-(4-(5-Methyl-1,3,4-oxadiazol-2-yl)phenoxy)-5-methyl-2-oxopyrrolidin-3-yl)methoxy)-N-(5-methylthiazol-2-yl)benzamide;

N-(5-Chlorothiazol-2-yl)-3-(4-(5-methyl-1,3,4-oxadiazol-2-yl)phenoxy)-5-((1-methyl-2-oxopyrrolidin-3-yl)methoxy)benzamide;

N-(5-Fluorothiazol-2-yl)-3-(4-(5-methyl-1,3,4-oxadiazol-2-yl)phenoxy)-5-((1-methyl-2-oxopyrrolidin-3-yl)methoxy)benzamide;

Ethyl 4-(hydroxymethyl)-2-(3-(4-(5-methyl-1,3,4-oxadiazol-2-yl)phenoxy)-5-((1-methyl-2-oxopyrrolidin-3-yl)methoxy)benzamido)thiazole-5-carboxylate;

Ethyl 2-(3-(4-(5-methyl-1,3,4-oxadiazol-2-yl)phenoxy)-5-((1-methyl-2-oxopyrrolidin-3-yl)methoxy)benzamido)thiazole-5-carboxylate;

Ethyl 4-(methoxymethyl)-2-(3-(4-(5-methyl-1,3,4-oxadiazol-2-yl)phenoxy)-5-((1-methyl-2-oxopyrrolidin-3-yl)methoxy)benzamido)thiazole-5-carboxylate;

Ethyl 2-(2-(3-(4-(5-methyl-1,3,4-oxadiazol-2-yl)phenoxy)-5-((1-methyl-2-oxopyrrolidin-3-yl)methoxy)benzamido)thiazol-4-yl)acetate;

2-(2-(3-(4-(5-Methyl-1,3,4-oxadiazol-2-yl)phenoxy)-5-((1-methyl-2-oxopyrrolidin-3-yl)methoxy)benzamido)thiazol-4-yl)acetic acid;

N-(4-(2-Amino-2-oxoethyl)thiazol-2-yl)-3-(4-(5-methyl-1,3,4-oxadiazol-2-yl)phenoxy)-5-((1-methyl-2-oxopyrrolidin-3-yl)methoxy)benzamide;

N-(4-(2-(diethylamino)-2-oxoethyl)thiazol-2-yl)-3-(4-(5-methyl-1,3,4-oxadiazol-2-yl)phenoxy)-5-((1-methyl-2-oxopyrrolidin-3-yl)methoxy)benzamide;

3-(4-(5-Methyl-1,3,4-oxadiazol-2-yl)phenoxy)-5-((1-methyl-2-oxopyrrolidin-3-yl)methoxy)-N-(4-(2-oxo-2-(piperidin-1-yl)ethyl)thiazol-2-yl)benzamide;

3-(4-(5-Methyl-1,3,4-oxadiazol-2-yl)phenoxy)-5-((1-methyl-2-oxopyrrolidin-3-yl)methoxy)-N-(4-(2-(4-methylpiperazin-1-yl)-2-oxoethyl)thiazol-2-yl)benzamide;

3-(4-(5-Methyl-1,3,4-oxadiazol-2-yl)phenoxy)-5-((1-methyl-2-oxopyrrolidin-3-yl)methoxy)-N-(4-(2-morpholino-2-oxoethyl)thiazol-2-yl)benzamide;

3-(4-(5-Methyl-1,3,4-oxadiazol-2-yl)phenoxy)-5-((1-methyl-2-oxopyrrolidin-3-yl)methoxy)-N-(pyrazin-2-yl)benzamide;

Methyl 6-(3-(4-(5-methyl-1,3,4-oxadiazol-2-yl)phenoxy)-5-methyl-2-oxopyrrolidin-3-yl)methoxy)benzamido)nicotinate;

N-(Benzo[d]thiazol-2-yl)-3-(4-(5-methyl-1,3,4-oxadiazol-2-yl)phenoxy)-5-((1-methyl-2-oxopyrrolidin-3-yl)methoxy)benzamide;

N-(1H-Indazol-4-yl)-3-(4-(5-methyl-1,3,4-oxadiazol-2-yl)phenoxy)-5-((1-methyl-2-oxopyrrolidin-3-yl)methoxy)benzamide;

N-(5,5-Dimethyl-4-oxo-4,5-dihydrothiazol-2-yl)-3-(4-(5-methyl-1,3,4-oxadiazol-2-yl)phenoxy)-5-((1-methyl-2-oxopyrrolidin-3-yl)methoxy)benzamide;

3-(4-(5-Methyl-1,3,4-oxadiazol-2-yl)phenoxy)-5-((1-methyl-2-oxopyrrolidin-3-yl)methoxy)-N-(1H-pyrazol-3-yl)benzamide;

3-(4-(5-Methyl-1,3,4-oxadiazol-2-yl)phenoxy)-N-(5-methyl-1,3,4-thiadiazol-2-yl)-5-((1-methyl-2-oxopyrrolidin-3-yl)methoxy)benzamide;

N-(5-Cyclopropyl-1,3,4-thiadiazol-2-yl)-3-(4-(5-methyl-1,3,4-oxadiazol-2-yl)phenoxy)-5-((1-methyl-2-oxopyrrolidin-3-yl)methoxy)benzamide;

N-(5-Cyclopropyl-1,3,4-thiadiazol-2-yl)-3-(4-(3-methyl-1,2,4-oxadiazol-5-yl)phenoxy)-5-((1-methyl-2-oxopyrrolidin-3-yl)methoxy)benzamide;

3-(4-(3-Methyl-1,2,4-oxadiazol-5-yl)phenoxy)-5-((1-methyl-2-oxopyrrolidin-3-yl)methoxy)-N-(thiazol-2-yl)benzamide;

3-(4-(3-Methyl-1,2,4-oxadiazol-5-yl)phenoxy)-5-((1-methyl-2-oxopyrrolidin-3-yl)methoxy)-N-(4-methylthiazol-2-yl)benzamide;

3-(4-(3-Methyl-1,2,4-oxadiazol-5-yl)phenoxy)-5-((1-methyl-2-oxopyrrolidin-3-yl)methoxy)-N-(5-methylthiazol-2-yl)benzamide;

N-(5-Chlorothiazol-2-yl)-3-(4-(3-methyl-1,2,4-oxadiazol-5-yl)phenoxy)-5-((1-methyl-2-oxopyrrolidin-3-yl)methoxy)benzamide;

N-(5-Fluorothiazol-2-yl)-3-(4-(3-methyl-1,2,4-oxadiazol-5-yl)phenoxy)-5-((1-methyl-2-oxopyrrolidin-3-yl)methoxy)benzamide;

3-(4-(3-Ethyl-1,2,4-oxadiazol-5-yl)phenoxy)-5-((1-methyl-2-oxopyrrolidin-3-yl)methoxy)-N-(thiazol-2-yl)benzamide;

3-(4-(3-Ethyl-1,2,4-oxadiazol-5-yl)phenoxy)-5-((1-ethyl-2-oxopyrrolidin-3-yl)methoxy)-N-(thiazol-2-yl)benzamide;

3-(4-(3-Ethyl-1,2,4-oxadiazol-5-yl)phenoxy)-5-((1-isopropyl-2-oxopyrrolidin-3-yl)methoxy)-N-(thiazol-2-yl)benzamide;

3-(4-(1,2,4-Oxadiazol-5-yl)phenoxy)-5-((1-methyl-2-oxopyrrolidin-3-yl)methoxy)-N-(thiazol-2-yl)benzamide;

3-(4-(1,2,4-Oxadiazol-5-yl)phenoxy)-5-((1-methyl-2-oxopyrrolidin-3-yl)methoxy)-N-(5-methylthiazol-2-yl)benzamide;

3-(4-(1,2,4-Oxadiazol-5-yl)phenoxy)-N-(5-fluorothiazol-2-yl)-5-methyl-2-oxopyrrolidin-3-yl)methoxy)benzamide;

3-(4-(5-Methyl-1,3,4-oxadiazol-2-yl)phenoxy)-5-(1-methyl-2-oxopyrrolidin-3-yloxy)-N-(thiazol-2-yl)benzamide;

3-(4-(5-Methyl-1,3,4-oxadiazol-2-yl)phenoxy)-5-(1-methyl-2-oxopyrrolidin-3-yloxy)-N-(4-methylthiazol-2-yl)benzamide;

3-(4-(5-Methyl-1,3,4-oxadiazol-2-yl)phenoxy)-5-(1-methyl-2-oxopyrrolidin-3-yloxy)-N-(5-methylthiazol-2-yl)benzamide;

N-(5-Chlorothiazol-2-yl)-3-(4-(5-methyl-1,3,4-oxadiazol-2-yl)phenoxy)-5-(1-methyl-2-oxopyrrolidin-3-yloxy)benzamide;

N-(5-Fluorothiazol-2-yl)-3-(4-(5-methyl-1,3,4-oxadiazol-2-yl)phenoxy)-5-(1-methyl-2-oxopyrrolidin-3-yloxy)benzamide;

Ethyl 4-(methoxymethyl)-2-(3-(4-(5-methyl-1,3,4-oxadiazol-2-yl)phenoxy)-5-(1-methyl-2-oxopyrrolidin-3-yloxy)benzamido)thiazole-5-carboxylate;

Ethyl 2-(2-(3-(4-(5-methyl-1,3,4-oxadiazol-2-yl)phenoxy)-5-(1-methyl-2-oxopyrrolidin-3-yloxy)benzamido)thiazol-4-yl)acetate;

2-(2-(3-(4-(5-Methyl-1,3,4-oxadiazol-2-yl)phenoxy)-5-(1-methyl-2-oxopyrrolidin-3-yloxy)benzamido)thiazol-4-yl)acetic acid;

N-(4-(2-Amino-2-oxoethyl)thiazol-2-yl)-3-(4-(5-methyl-1,3,4-oxadiazol-2-yl)phenoxy)-5-(1-methyl-2-oxopyrrolidin-3-yloxy)benzamide;

N-(4-(2-(Diethylamino)-2-oxoethyl)thiazol-2-yl)-3-(4-(5-methyl-1,3,4-oxadiazol-2-yl)phenoxy)-5-(1-methyl-2-oxopyrrolidin-3-yloxy)benzamide;

3-(4-(5-Methyl-1,3,4-oxadiazol-2-yl)phenoxy)-5-(1-methyl-2-oxopyrrolidin-3-yloxy)-N-(4-(2-oxo-2-(piperidin-1-yl)ethyl)thiazol-2-yl)benzamide;

3-(4-(5-Methyl-1,3,4-oxadiazol-2-yl)phenoxy)-5-(1-methyl-2-oxopyrrolidin-3-yloxy)-N-(4-(2-morpholino-2-oxoethyl)thiazol-2-yl)benzamide;

3-(4-(5-Methyl-1,3,4-oxadiazol-2-yl)phenoxy)-5-(1-methyl-2-oxopyrrolidin-3-yloxy)-N-(4-(2-(4-methylpiperazin-1-yl)-2-oxoethyl)thiazol-2-yl)benzamide;

3-(1-Ethyl-2-oxopyrrolidin-3-yloxy)-5-(4-(5-methyl-1,3,4-oxadiazol-2-yl)phenoxy)-N-(thiazol-2-yl)benzamide;

3-(1-Isopropyl-2-oxopyrrolidin-3-yloxy)-5-(4-(5-methyl-1,3,4-oxadiazol-2-yl)phenoxy)-N-(thiazol-2-yl)benzamide;

3-(4-(5-Ethyl-1,3,4-oxadiazol-2-yl)phenoxy)-5-(1-methyl-2-oxopyrrolidin-3-yloxy)-N-(thiazol-2-yl)benzamide;

N-(5,5-dimethyl-4-oxo-4,5-dihydrothiazol-2-yl)-3-(4-(5-methyl-1,3,4-oxadiazol-2-yl)phenoxy)-5-(1-methyl-2-oxopyrrolidin-3-yloxy)benzamide;

N-(Benzo[d]thiazol-2-yl)-3-(4-(5-methyl-1,3,4-oxadiazol-2-yl)phenoxy)-5-(1-methyl-2-oxopyrrolidin-3-yloxy)benzamide;

3-(4-(5-Methyl-1,3,4-oxadiazol-2-yl)phenoxy)-N-(5-methyl-1,3,4-thiadiazol-2-yl)-5-(1-methyl-2-oxopyrrolidin-3-yloxy)benzamide;

N-(5-Cyclopropyl-1,3,4-thiadiazol-2-yl)-3-(4-(5-methyl-1,3,4-oxadiazol-2-yl)phenoxy)-5-(1-methyl-2-oxopyrrolidin-3-yloxy)benzamide;

N-(1H-Indazol-4-yl)-3-(4-(5-methyl-1,3,4-oxadiazol-2-yl)phenoxy)-5-(1-methyl-2-oxopyrrolidin-3-yloxy)benzamide;

3-(4-(5-Methyl-1,3,4-oxadiazol-2-yl)phenoxy)-5-(1-methyl-2-oxopyrrolidin-3-yloxy)-N-(pyrazin-2-yl)benzamide;

Methyl 6-(3-(4-(5-methyl-1,3,4-oxadiazol-2-yl)phenoxy)-5-(1-methyl-2-oxopyrrolidin-3-yloxy)benzamido)nicotinate;

3-(4-(5-Ethyl-1,3,4-oxadiazol-2-yl)phenoxy)-5-(1-methyl-2-oxopyrrolidin-3-yloxy)-N-(thiazol-2-yl)benzamide;
3-(4-(5-Isopropyl-1,3,4-oxadiazol-2-yl)phenoxy)-5-(1-methyl-2-oxopyrrolidin-3-yloxy)-N-(thiazol-2-yl)benzamide;
3-(1-Ethyl-2-oxopyrrolidin-3-yloxy)-5-(4-(5-methyl-1,3,4-oxadiazol-2-yl)phenoxy)-N-(thiazol-2-yl)benzamide;
3-(4-(3-Methyl-1,2,4-oxadiazol-5-yl)phenoxy)-5-(1-methyl-2-oxopyrrolidin-3-yloxy)-N-(thiazol-2-yl)benzamide;
3-(4-(3-Methyl-1,2,4-oxadiazol-5-yl)phenoxy)-5-(1-methyl-2-oxopyrrolidin-3-yloxy)-N-(4-methylthiazol-2-yl)benzamide;
3-(4-(3-Methyl-1,2,4-oxadiazol-5-yl)phenoxy)-5-(1-methyl-2-oxopyrrolidin-3-yloxy)-N-(5-methylthiazol-2-yl)benzamide;
N-(5-Chlorothiazol-2-yl)-3-(4-(3-methyl-1,2,4-oxadiazol-5-yl)phenoxy)-5-(1-methyl-2-oxopyrrolidin-3-yloxy)benzamide;
N-(5-Fluorothiazol-2-yl)-3-(4-(3-methyl-1,2,4-oxadiazol-5-yl)phenoxy)-5-(1-methyl-2-oxopyrrolidin-3-yloxy)benzamide;
N-(Benzo[d]thiazol-2-yl)-3-(4-(3-methyl-1,2,4-oxadiazol-5-yl)phenoxy)-5-(1-methyl-2-oxopyrrolidin-3-yloxy)benzamide;
3-(4-(3-Methyl-1,2,4-oxadiazol-5-yl)phenoxy)-N-(5-methyl-1,3,4-thiadiazol-2-yl)-5-(1-methyl-2-oxopyrrolidin-3-yloxy)benzamide;
N-(5-Cyclopropyl-1,3,4-thiadiazol-2-yl)-3-(4-(3-methyl-1,2,4-oxadiazol-5-yl)phenoxy)-5-(1-methyl-2-oxopyrrolidin-3-yloxy)benzamide;
3-(4-(3-Methyl-1,2,4-oxadiazol-5-yl)phenoxy)-5-(1-methyl-2-oxopyrrolidin-3-yloxy)-N-(1H-pyrazol-3-yl)benzamide;
3-(4-(3-Methyl-1,2,4-oxadiazol-5-yl)phenoxy)-N-(1-methyl-1H-pyrazol-3-yl)-5-(1-methyl-2-oxopyrrolidin-3-yloxy)benzamide;
3-(4-(1H-Imidazol-2-yl)phenoxy)-5-(1-methyl-2-oxopyrrolidin-3-yloxy)-N-(thiazol-2-yl)benzamide;
3-(4-(1-Methyl-1H-imidazol-2-yl)phenoxy)-5-(1-methyl-2-oxopyrrolidin-3-yloxy)-N-(thiazol-2-yl)benzamide;
3-(4-(1H-Benzo imidazol-2-yl)phenoxy)-5-(1-methyl-2-oxopyrrolidin-3-yloxy)-N-(thiazol-2-yl)benzamide;
3-(4-(1-Methyl-1H-benzo[d]imidazol-2-yl)phenoxy)-5-(1-methyl-2-oxopyrrolidin-3-yloxy)-N-(thiazol-2-yl)benzamide;
3-(4-(4,5-Dihydro-1H-imidazol-2-yl)phenoxy)-5-(1-methyl-2-oxopyrrolidin-3-yloxy)-N-(thiazol-2-yl)benzamide;
3-(1-Methyl-2-oxopyrrolidin-3-yloxy)-5-(4-(1-methyl-4,5-dihydro-1H-imidazol-2-yl)phenoxy)-N-(thiazol-2-yl)benzamide;
3-(4-Cyanophenoxy)-5-(1-methyl-2-oxopyrrolidin-3-yloxy)-N-(thiazol-2-yl)benzamide;
3-(1-Methyl-2-oxopyrrolidin-3-yloxy)-5-(4-(oxazol-2-yl)phenoxy)-N-(thiazol-2-yl)benzamide;
3-(4-(1,3-Dimethyl-1H-1,2,4-triazol-5-yl)phenoxy)-5-(1-methyl-2-oxopyrrolidin-3-yloxy)-N-(thiazol-2-yl)benzamide;
(S)-3-(4-(5-Methyl-1,3,4-oxadiazol-2-yl)phenoxy)-5-((2-oxopyrrolidin-3-yl)oxy)-N-(thiazol-2-yl)benzamide;
(R)-3-(4-(5-Methyl-1,3,4-oxadiazol-2-yl)phenoxy)-5-((2-oxopyrrolidin-3-yl)oxy)-N-(thiazol-2-yl)benzamide;
(S)—N-(Benzo[d]thiazol-2-yl)-3-(4-(5-methyl-1,3,4-oxadiazol-2-yl)phenoxy)-5-((2-oxopyrrolidin-3-yl)oxy)benzamide;
(R)—N-(Benzo[d]thiazol-2-yl)-3-(4-(5-methyl-1,3,4-oxadiazol-2-yl)phenoxy)-5-((2-oxopyrrolidin-3-yl)oxy)benzamide;
(R)-3-(4-(5-Methyl-1,3,4-oxadiazol-2-yl)phenoxy)-N-(4-methylthiazol-2-yl)-5-((2-oxopyrrolidin-3-yl)oxy)benzamide;
(S)-3-(4-(5-Methyl-1,3,4-oxadiazol-2-yl)phenoxy)-N-(4-methylthiazol-2-yl)-5-((2-oxopyrrolidin-3-yl)oxy)benzamide;
(R)-3-(4-(5-Methyl-1,3,4-oxadiazol-2-yl)phenoxy)-N-(5-methylthiazol-2-yl)-5-((2-oxopyrrolidin-3-yl)oxy)benzamide;
(S)-3-(4-(5-Methyl-1,3,4-oxadiazol-2-yl)phenoxy)-N-(5-methylthiazol-2-yl)-5-((2-oxopyrrolidin-3-yl)oxy)benzamide;
(R)-3-(4-(5-Methyl-1,3,4-oxadiazol-2-yl)phenoxy)-5-((2-oxopyrrolidin-3-yl)oxy)-N-(4-phenylthiazol-2-yl)benzamide;
(S)-3-(4-(5-Methyl-1,3,4-oxadiazol-2-yl)phenoxy)-5-((2-oxopyrrolidin-3-yl)oxy)-N-(4-phenylthiazol-2-yl)benzamide;
(R)-Ethyl 2-(3-(4-(5-methyl-1,3,4-oxadiazol-2-yl)phenoxy)-5-((2-oxopyrrolidin-3-yl)oxy)benzamido)thiazole-4-carboxylate;
(S)-Ethyl 2-(4-(5-methyl-1,3,4-oxadiazol-2-yl)phenoxy)-5-((2-oxopyrrolidin-3-yl)oxy)benzamido)thiazole-4-carboxylate;
3-(4-(1,3-Dimethyl-1H-1,2,4-triazol-5-yl)phenoxy)-5-(1-methyl-2-oxopyrrolidin-3-yloxy)-N-(thiazol-2-yl)benzamide;
3-(4-(1,3-Dimethyl-1H-1,2,4-triazol-5-yl)phenoxy)-5-(1-methyl-2-oxopyrrolidin-3-yloxy)-N-(4-methylthiazol-2-yl)benzamide;
3-(4-(1,3-Dimethyl-1H-1,2,4-triazol-5-yl)phenoxy)-5-(1-methyl-2-oxopyrrolidin-3-yloxy)-N-(5-methylthiazol-2-yl)benzamide;
N-(5-Chlorothiazol-2-yl)-3-(4-(1,3-dimethyl-1H-1,2,4-triazol-5-yl)phenoxy)-5-(1-methyl-2-oxopyrrolidin-3-yloxy)benzamide;
3-(4-(1,3-Dimethyl-1H-1,2,4-triazol-5-yl)phenoxy)-N-(5-fluorothiazol-2-yl)-5-(1-methyl-2-oxopyrrolidin-3-yloxy)benzamide;
3-(4-(1,3-Dimethyl-1H-1,2,4-triazol-5-yl)phenoxy)-5-(1-ethyl-2-oxopyrrolidin-3-yloxy)-N-(thiazol-2-yl)benzamide;
3-(4-(1,3-Dimethyl-1H-1,2,4-triazol-5-yl)phenoxy)-5-(1-isopropyl-2-oxopyrrolidin-3-yloxy)-N-(thiazol-2-yl)benzamide;
3-(4-(1,3-Dimethyl-1H-1,2,4-triazol-5-yl)phenoxy)-N-(5,5-dimethyl-4-oxo-4,5-dihydrothiazol-2-yl)-5-(1-methyl-2-oxopyrrolidin-3-yloxy)benzamide;
N-(Benzo[d]thiazol-2-yl)-3(4-(1,3-dimethyl-1H-1,2,4-triazol-5-yl)phenoxy)-5-(1-methyl-2-oxopyrrolidin-3-yloxy)benzamide;
3-(4-(1,3-Dimethyl-1H-1,2,4-triazol-5-yl)phenoxy)-N-(1H-indazol-4-yl)-5-(1-methyl-2-oxopyrrolidin-3-yloxy)benzamide;
(S)-3-(4-(5-Methyl-1,3,4-oxadiazol-2-yl)phenoxy)-5-((1-methyl-2-oxopyrrolidin-3-yl)oxy)-N-(thiazol-2-yl)benzamide;
(R)-3-(4-(5-Methyl-1,3,4-oxadiazol-2-yl)phenoxy)-5-((1-methyl-2-oxopyrrolidin-3-yl)oxy)-N-(thiazol-2-yl)benzamide;
(S)-3-(4-(5-Methyl-1,3,4-oxadiazol-2-yl)phenoxy)-5-((1-methyl-2-oxopyrrolidin-3-yl)oxy)-N-(5-methylthiazol-2-yl)benzamide;

(R)-3-(4-(5-Methyl-1,3,4-oxadiazol-2-yl)phenoxy)-5-((1-methyl-2-oxopyrrolidin-3-yl)oxy)-N-(5-methylthiazol-2-yl)benzamide;
(S)-3-(4-(5-Methyl-1,3,4-oxadiazol-2-yl)phenoxy)-5-((1-methyl-2-oxopyrrolidin-3-yl)oxy)-N-(4-methylthiazol-2-yl)benzamide;
(R)-3-(4-(5-Methyl-1,3,4-oxadiazol-2-yl)phenoxy)-5-((1-methyl-2-oxopyrrolidin-3-yl)oxy)-N-(4-methylthiazol-2-yl)benzamide;
(S)-3-(4-(5-Ethyl-1,3,4-oxadiazol-2-yl)phenoxy)-5-((1-methyl-2-oxopyrrolidin-3-yl)oxy)-N-(thiazol-2-yl)benzamide;
(R)-3-(4-(5-Ethyl-1,3,4-oxadiazol-2-yl)phenoxy)-5-((1-methyl-2-oxopyrrolidin-3-yl)oxy)-N-(thiazol-2-yl)benzamide;
(S)-3-(4-(5-Isopropyl-1,3,4-oxadiazol-2-yl)phenoxy)-5-((1-methyl-2-oxopyrrolidin-3-yl)oxy)-N-(thiazol-2-yl)benzamide;
(R)-3-(4-(5-Isopropyl-1,3,4-oxadiazol-2-yl)phenoxy)-5-((1-methyl-2-oxopyrrolidin-3-yl)oxy)-N-(thiazol-2-yl)benzamide;
(S)-3-(4-(5-Isopropyl-1,3,4-oxadiazol-2-yl)phenoxy)-5-((1-methyl-2-oxopyrrolidin-3-yl)oxy)-N-(5-methylthiazol-2-yl)benzamide;
(R)-3-(4-(5-Isopropyl-1,3,4-oxadiazol-2-yl)phenoxy)-5-((1-methyl-2-oxopyrrolidin-3-yl)oxy)-N-(4-methylthiazol-2-yl)benzamide;
(S)-3-(4-(5-Isopropyl-1,3,4-oxadiazol-2-yl)phenoxy)-5((1-methyl-2-oxopyrrolidin-3-yl)oxy)-N-(4-methylthiazol-2-yl)benzamide;
(S)-3-((1-Ethyl-2-oxopyrrolidin-3-yl)oxy)-5-(4-(5-methyl-1,3,4-oxadiazol-2-yl)phenoxy)-N-(thiazol-2-yl)benzamide;
(R)-3-((1-Ethyl-2-oxopyrrolidin-3-yl)oxy)-5-(4-(5-methyl-1,3,4-oxadiazol-2-yl)phenoxy)-N-(thiazol-2-yl)benzamide;
(R)-3-((1-Ethyl-2-oxopyrrolidin-3-yl)oxy)-5-(4-(5-methyl-1,3,4-oxadiazol-2-yl)phenoxy)-N-(5-methylthiazol-2-yl)benzamide;
(S)-3-((1-Ethyl-2-oxopyrrolidin-3-yl)oxy)-5-(4-(5-methyl-1,3,4-oxadiazol-2-yl)phenoxy)-N-(5-methylthiazol-2-yl)benzamide;
(R)-3-((1-Ethyl-2-oxopyrrolidin-3-yl)oxy)-5-(4-(5-methyl-1,3,4-oxadiazol-2-yl)phenoxy)-N-(4-methylthiazol-2-yl)benzamide;
(S)-3((1-Ethyl-2-oxopyrrolidin-3-yl)oxy)-5-(4-(5-methyl-1,3,4-oxadiazol-2-yl)phenoxy)-N-(4-methylthiazol-2-yl)benzamide, and their pharmaceutically acceptable salts, pharmaceutically acceptable solvates, enantiomers, diastereomers, prodrugs, metabolites, and polymorphs.

In another aspect there are provided pharmaceutical compositions comprising a therapeutically effective amount of a compound disclosed herein and optionally one or more pharmaceutically acceptable carriers, excipients or diluents.

In another aspect there are provided methods for treating disease states mediated by glucokinase, comprising administering to patient in need thereof a therapeutically effective amount of a compound disclosed herein and optionally one or more pharmaceutically acceptable carriers, excipients or diluents. These methods encompass one or more of the following features. For example, the disease can be type II diabetes. In another example, the compounds may be useful in reducing blood glucose levels and increasing insulin secretion.

The novel compounds of the present invention are prepared using the reactions and techniques described below, together with conventional techniques known to those skilled in the art of organic synthesis, or variations thereon as appreciated by those skilled in the art.

The reactions are performed in solvents appropriate to the reagents and materials employed and are suitable for the transformations being effected. Preferred methods include, but not limited to those described below, where all symbols are as defined earlier unless and otherwise defined below.

The compounds of Formula (I) can be prepared as described in scheme 1: Methyl 3,5-dihydroxybenzoate 2 may be subjected to regioselective nucleophilic displacement reaction with compound 3 in the presence of a suitable base, for example, potassium carbonate, cesium carbonate, or sodium carbonate, in one or more suitable polar solvents, for example, 1,4-dioxane, dimethylformamide, dimethylacetamide, dimethyl sulfoxide, or mixtures thereof, to yield phenol 4. The Phenol 4 may be subjected to second nucleophilic substitution reaction with compound 5 using a suitable base in one or more suitable polar solvents in the presence of a suitable salt selected from Cu(I) salts or Cu(II) salts or Pd (0) or Pd (II) salts, to yield ester 6. The basic hydrolysis of the ester 6, followed by acidic treatment yield acid 7. The acid 7 thus obtained may be coupled with differentially substituted heteroaryl amines 8 to yield the compound (I) of the invention.

Scheme 1:

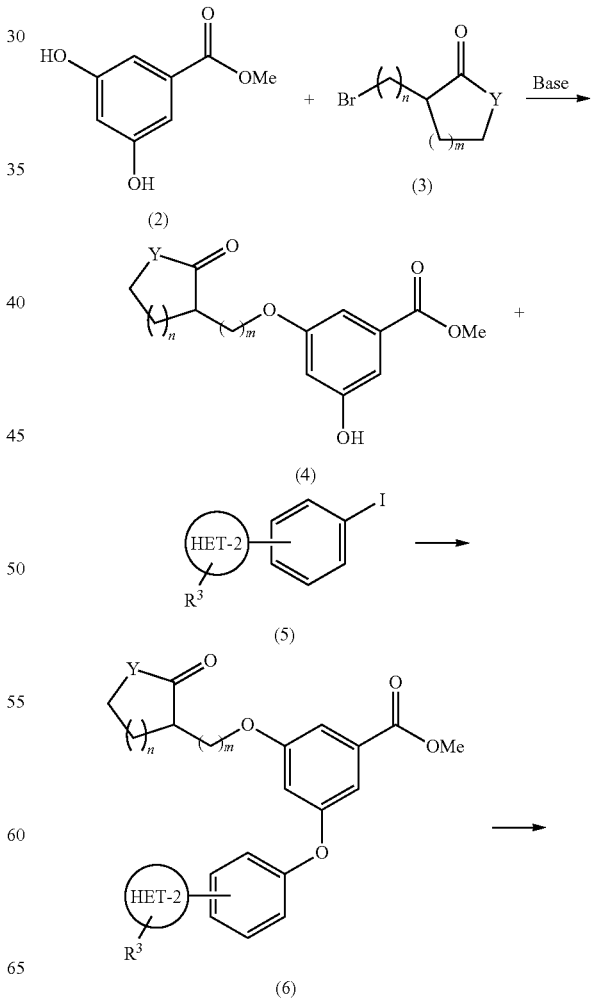

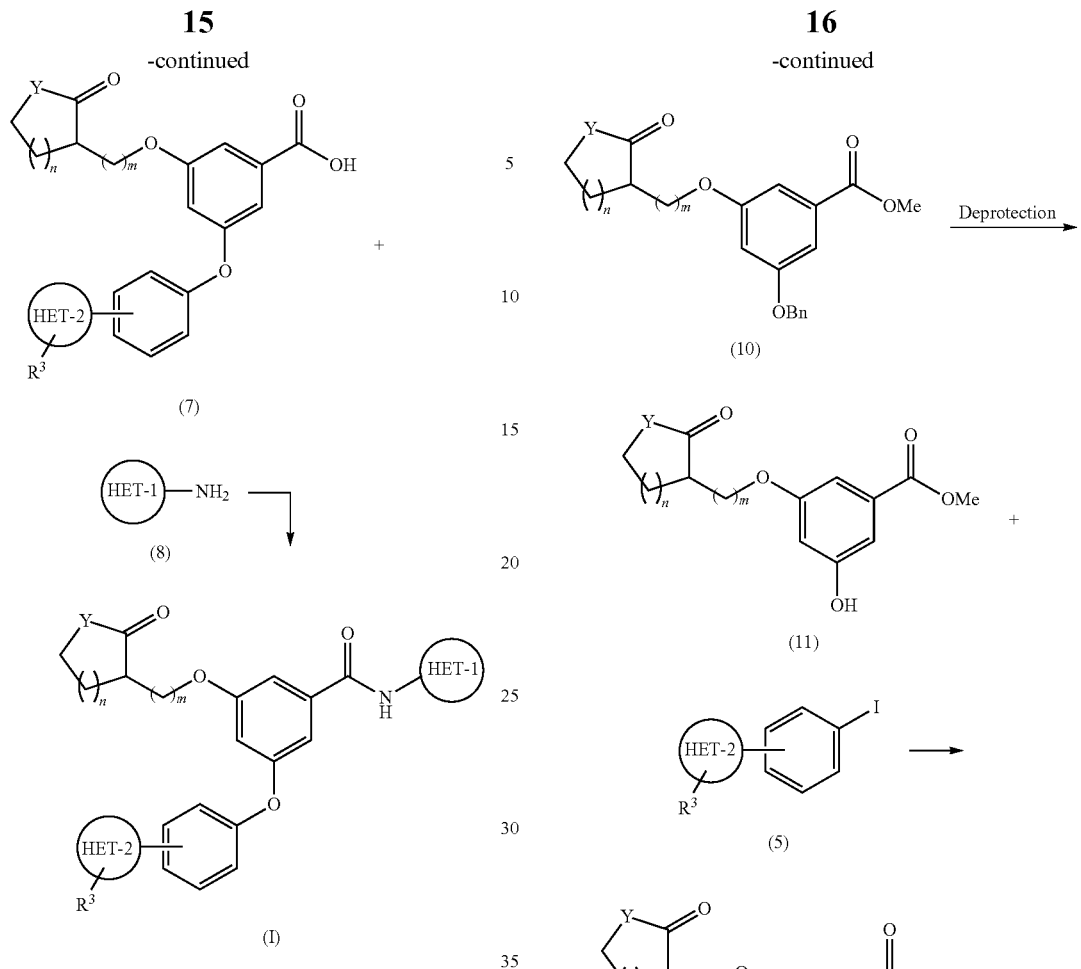

Alternatively, the compounds of Formula (I) can be prepared as described in scheme 2:

Methyl-3,5-dihydroxy benzoate 2 may be monoprotected regioselectively to get phenol 9, followed by nucleophilc displacement reaction with compound 3 using a suitable base in one or more suitable polar solvents, to yield compound 10. Suitable deprotection followed by second nucleophilic reaction with compound 5 in presence of a suitable base in a suitable polar solvent in presence of suitable salts selected from Cu(I) salts or Cu(II) salts or Pd (0) or Pd (II) salts to yield ester 6. The basic hydrolysis of ester 6 followed by acidic treatment gives acid 7. The acid 7 thus obtained may be coupled with differentially substituted heteroaryl amines 8 to furnish the compound (I) of the invention.

Scheme 2:

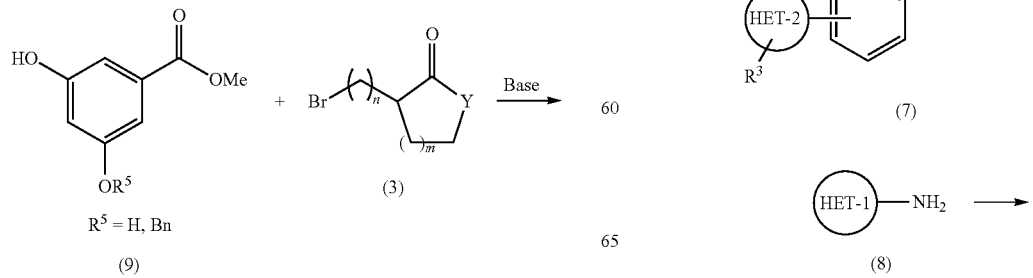

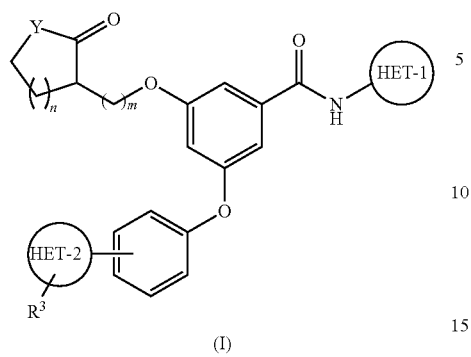

(I)

The compounds of Formula (I) can also be prepared as described in scheme 3:

Either Methyl 3,5-dihydroxybenzoate or monoprotected methyl benzoate 9 may be subjected to a nucleophilic displacement reaction with the benzaldehyde 12 employing a suitable base in a suitable polar solvent, to yield aldehyde 13. The aldehyde 13 may be converted to compound 14 by utilizing aldehyde functionality according to the literature techniques known to those skilled in the art of organic synthesis, or variations thereon as appreciated by those skilled in the art. Suitable deprotection of compound 14, followed by nucleophilic displacement reaction with compound 16 (wherein P=Br, I, Cl) using a suitable base in a suitable polar solvents yields ester 6.

The ester 6 may be prepared alternatively by subjecting compounds 15 and 16 (P=—OH) to Mitsunobu reaction conditions. The basic hydrolysis of ester 6, followed by acidic treatment gives acid 7. The acid 7 thus obtained may be coupled with differentially substituted heteroaryl amines 8 to give the compound (I) of the invention.

Scheme 3:

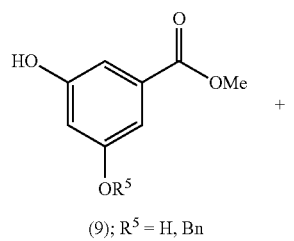

(9); $R^5$ = H, Bn (12)

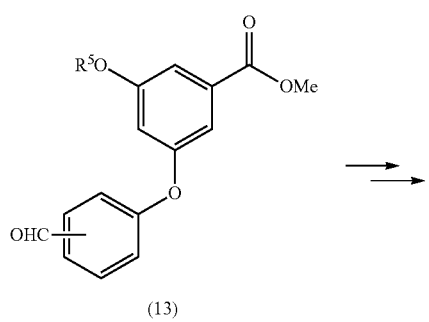

(13)

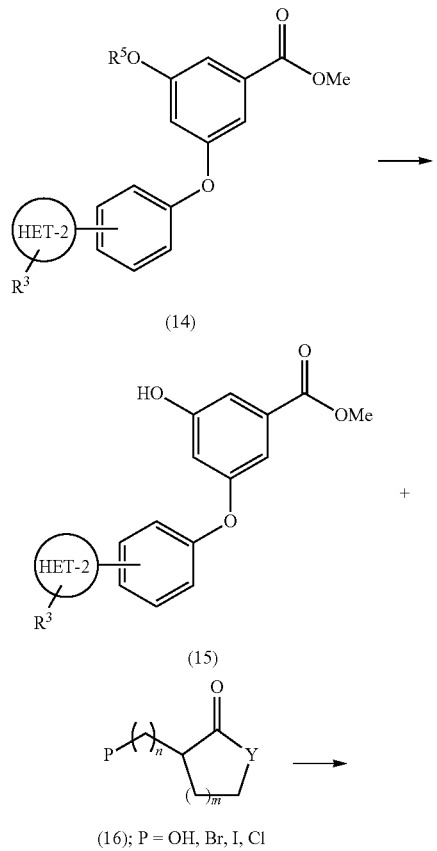

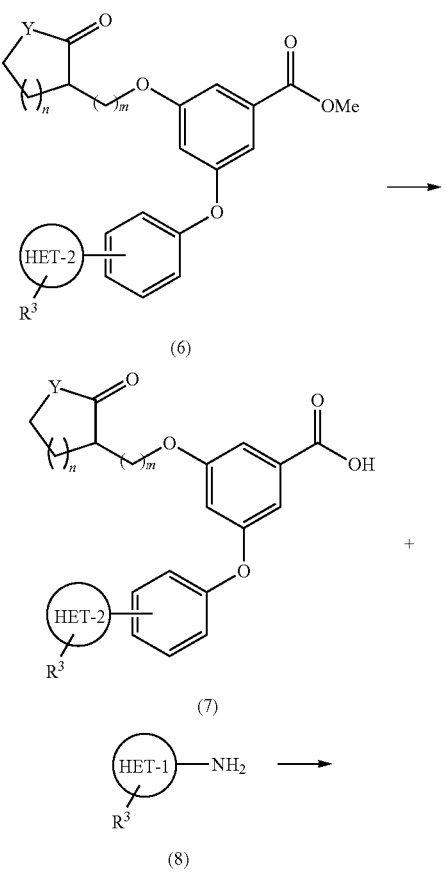

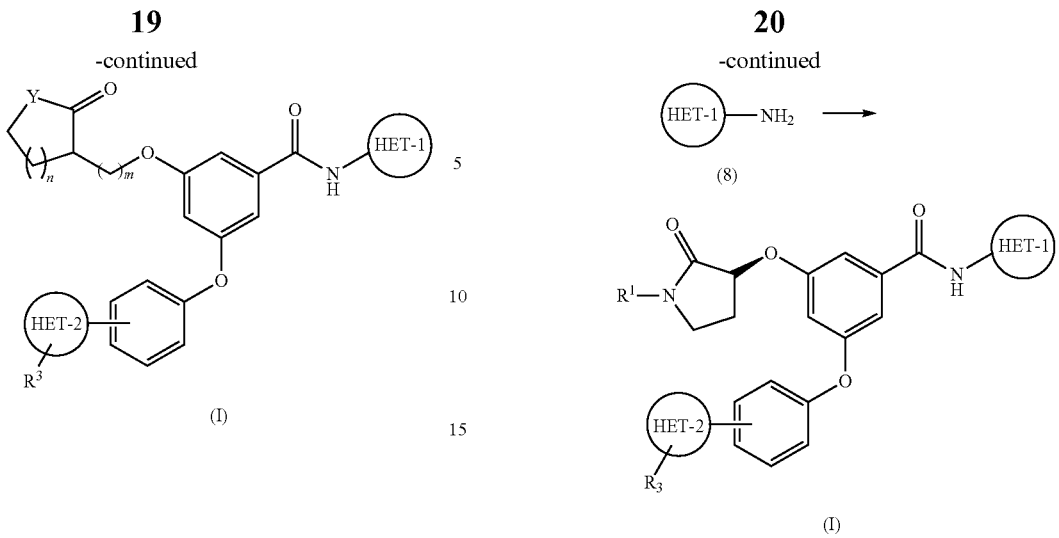

Scheme 4A:

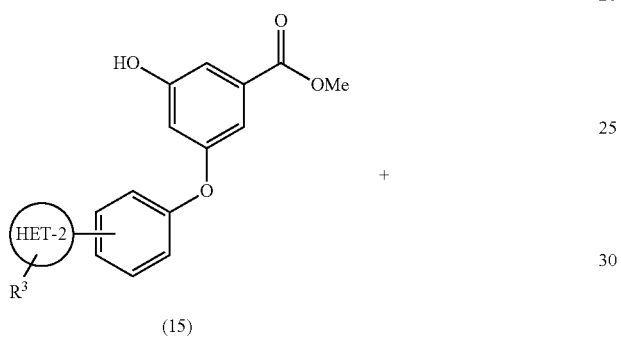

Chiral compounds of the invention can be prepared using Scheme 4A and Scheme 4B. Phenol 15 and intermediate 16 ($R^{10}$=H) may be subjected to Mitsunobu reaction under standrad reaction procedure to furnish ester 17. After N-alkylation, ester to 17 may be subjected to hydrolysis followed by acidification to yield the acid 18. Acid 18 may be coupled with differentially substituted heteroaryl amines to furnish compounds (I) of the invention.

Scheme 4B:

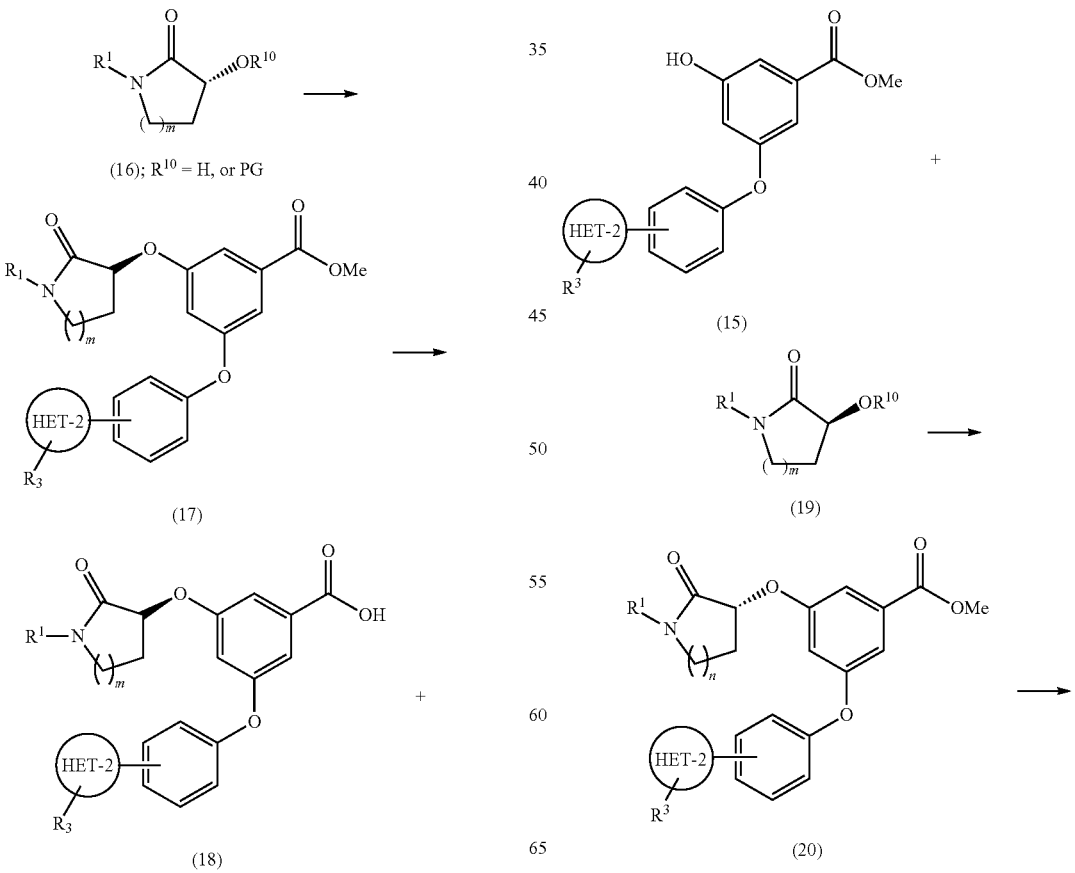

]Scheme 5A:

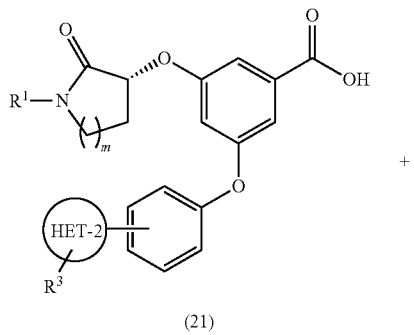
(21)

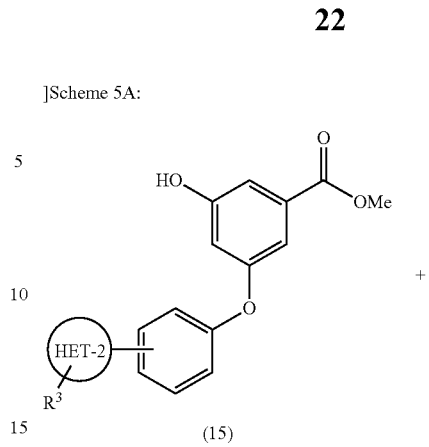
(15)

HET-1—NH₂ ⟶
(8)

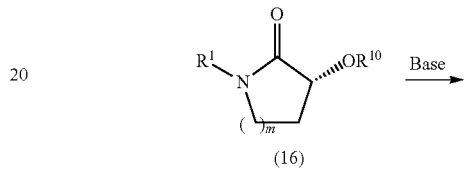
(16)

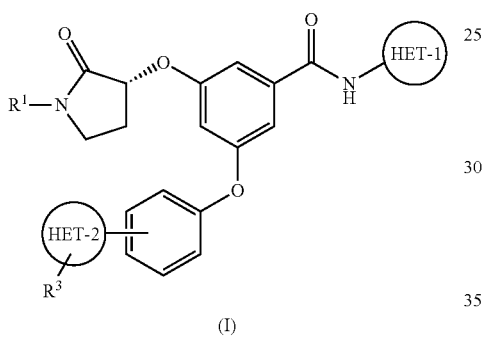
(I)

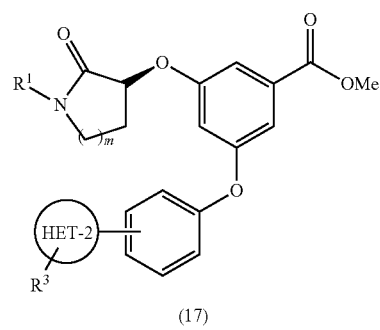
(17)

Phenol 15 and intermediate 19 (R¹⁰=H) may be subjected to Mitsunobu reaction under standrad reaction procedure to furnish ester 20. After N-alkylation, ester 20 may be subjected to hydrolysis followed by acidification to yield the acid 21. Acid 21 may be coupled with differentially substituted heteroaryl amines to furnish compounds (I) of the invention.

Alternatively, intermediate 17 may also be prepared by reacting phenol 15 with compound 16, wherein R¹⁰=PG, in presence of a base, in polar solvents (Scheme 5A). PG being leaving group may be selected from mesylate, tosylate, besylate, and the like. Base may be selected from cesium carbonate, potassium carbonate, sodium carbonate, and the like. Polar solvents may be selected from 1,4-dioxane, tetrahydrofuran, dimethylformamide, dimethylacetamide, and the like. Intermediate 17 may be further converted to compounds (I) according to Scheme 4A.

Intermediate 20 may also be prepared by reacting phenol 15 with compound 19, wherein R¹⁰=PG, in presence of a base, in polar solvents (Scheme 5B). PG being leaving group may be selected from mesylate, tosylate, besylate, and the like. Base may be selected from cesium carbonate, potassium carbonate, sodium carbonate, and the like. Polar solvents may be selected from 1,4-dioxane, tetrahydrofuran, dimethylformamide, dimethylacetamide, and the like. Intermediate 20 may be further converted to compounds (I) according to Scheme 4B.

Scheme 5B:

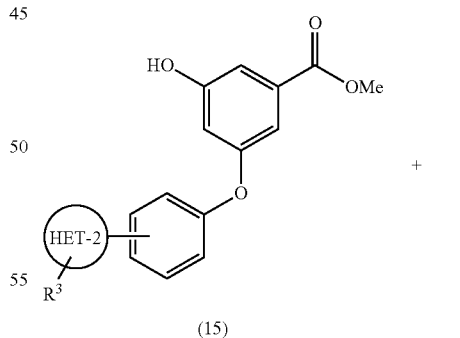
(15)

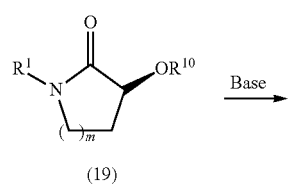
(19)

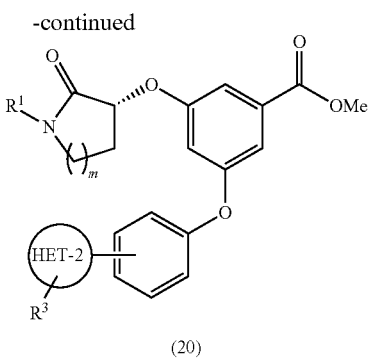

Scheme 6:

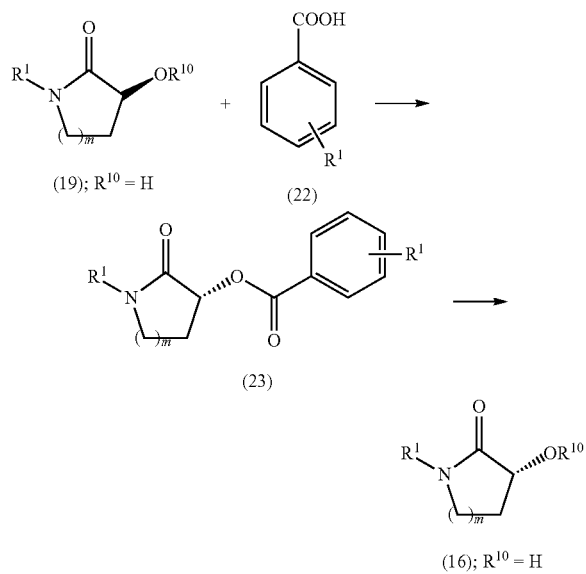

Intermediate 16 can also be prepared according to scheme 6, wherein all symbols are as defined earlier unless and otherwise defined below. Compound 19 ($R^{10}$=PG; PG=tosylate, mesylate, besylate) may be treated with aryl carboxylic acid 22 in presence of a suitable base, for example, cesium carbonate, potassium carbonate, or sodium carbonate, in one or more polar solvents, for example, dimethylformamide, 1,4-dioxane, dimethylacetamide, or tetrahydrofuran, to yield ester 23 with inversion. Alternatively, compound 19 ($R^{10}$=H) may be coupled with aryl carboxylic acid 22 in the presence of a peptide coupling reagent, for example, DCC, EDC.HCl, TBTU, HATU and Copper (I) halide, and a base, for example, cesium carbonate, potassium carbonate, or sodium carbonate, in one or more chlorinated solvents selected from dichloromethane, or chloroform to give an ester 23. The ester 23 can be hydrolyzed using conventional techniques known to those skilled in the art of organic synthesis, or variations thereon to give the compound 16 ($R^{10}$=H).

List of abbreviations used in the description of the preparation of the compounds of the present invention:
bs: broad singlet
n-BuLi: n-butyl lithium
$CDCl_3$: Deuterated chloroform
$CHCl_3$: Chloroform
d: doublet
dd: doublet of doublet
dt: doublet of triplet
DCC: Dicylcohexylcarbodiimide.
DCM: Dichloromethane
DMAP: 4-(Dimethylamino) pyridine
DMF: N,N-Dimethyl formamide
DMSO: Dimethyl sulfoxide
EDCI: N-(3-Dimethylaminopropyl)-N'-ethylcarbodiimide
$Et_3N$: Triethyl amine
EtOAc: Ethyl acetate
EtOH: Ethanol
HCl(g): Hydrogen chloride (gas)
HOBT: 1-Hydroxybenzotriazole
HPLC: High Performance Liquid Chromatography
$K_2CO_3$: Potassium carbonate
KI: Potassium iodide
KOH: Potassium hydroxide
$LiAlH_4$: Lithium Aluminum Hydride
LiHMDS: Lithium bis(trimethylsilyl)amide
MeOH: Methanol
m: multiplet
mmol: millimoles
MsCl: Methane sulfonyl chloride
MS: Mass spectrum
NaCN: Sodium cyanide
NaH: Sodium hydride
$^1$H NMR: Proton nuclear magnetic resonance
Pet ether: Petroleum ether, boiling range (60-80° C.)
s: singlet
$SOCl_2$: Thionyl chloride
t: Triplet
td: triplet of doublet
THF: Tetrahydrofuran
TLC: Thin layer chromatography
HPLC: Ultra Performance Liquid Chromatography The invention is further illustrated by the following examples, which are provided merely to be exemplary of the invention and do not limit the scope of the invention. Certain modifications and equivalents will be apparent to those skilled in the art and are intended to be included within the scope of the invention. $^1$H NMR spectral data given in the examples (vide infra) are recorded using a 400 MHz spectrometer (Bruker AVANCE-400) and reported in g scale. Until and otherwise mentioned the solvent used for NMR is $CDCl_3$.

EXAMPLE 1

3-(4-(5-Methyl-1,3,4-oxadiazol-2-yl)phenoxy)-5-(1-methyl-2-oxopyrrolidin-3-yloxy)-N-(thiazol-2-yl)benzamide 4-(Dimethylamino)pyridine (DMAP) (0.149 g), N-(3-Dimethylaminopropyl)-N'-ethylcarbodiimide hydrochloride (EDCI.HCl) (0.524 g) were added to a solution of 3-(1-Methoxypropan-2-yloxy)-5-(4-(5-methyl-1,3,4-oxadiazol-2-yl)phenoxy)benzoic acid (0.5 g) (Intermediate 1) in dry DCM under nitrogen at 0-5° C. 2-Aminothiazole (0.134 g) was added and the mixture was stirred for 16 h at room temperature. It was diluted with commercially available DCM. Organic phase was washed with dil HCl, saturated solution of $NaHCO_3$, water, brine, dried over $Na_2SO_4$, filtered and concentrated in vacuo to get the crude residue. The residue was chromatographed using silica gel as stationary phase and MeOH:$CHCl_3$ gradient as mobile phase up to yield the product (0.3 g) as a white solid.

$^1$H NMR (DMSO-$d_6$, 400 MHz) δ ppm: 1.92-2.01 (m, 1 H), 2.59 (s, 3 H), 2.60-2.65 (m, 1 H), 2.79 (s, 3 H), 3.31-3.34 (m, 1 H), 3.36-3.44 (m, 1 H), 5.15 (t, J=7.6 Hz, 1 H), 7.08 (s, 1 H), 7.24 (d, J=8.8 Hz, 2 H), 7.27-7.29 (m, 1 H), 7.40 (s, 1 H), 7.54 (s, 1 H), 7.62 (s, 1 H), 7.99 (d, J=8.8 Hz, 2 H), 12.60 (bs, 1 H); ESI-MS m/z (relative intensities): 492.03 (M+H)$^+$ (100%), 514.02 (M+Na)$^+$ (15%); UPLC Purity: 93.59%, Ret.time: 3.59 min.

Intermediate 1: 3-(4-(5-Methyl-1,3,4-oxadiazol-2-yl)phenoxy)-5-(1-methyl-2-oxo pyrrolidin-3-yloxy) benzoic acid A solution of Methyl 3-(4-(5-methyl-1,3,4-oxadiazol-2-yl)phenoxy)-5-(1-methyl-2-oxopyrrolidin-3-yloxy)benzoate (7 g) (Intermediate 2) in a mixture of THF and to methanol (1:1 ratio) was treated with a solution of sodium hydroxide (2 g) in water and the reaction mixture was stirred for 1 h at room temperature. The resulting solution was concentrated under vacuum to remove THF and methanol, diluted with water, and washed with EtOAc. The aqueous phase was cooled and acidified with 0.1N HCl and extracted with DCM, combined organic extracts washed with brine, dried over $Na_2SO_4$ and concentrated in vacuo to give the product (3.5 g) as white solid.

$^1$H NMR (CDCl$_3$, 400 MHz) δ ppm: 2.20-2.27 (m, 1 H), 2.59-2.67 (m, 1 H), 2.77 (s, 3 H), 2.95 (s, 3 H), 3.38-3.44 (m, 1 H), 3.49-3.54 (m, 1 H), 4.96 (t, J=7.2 Hz, 1 H), 6.93-6.95 (m, 1 H), 7.07 (d, J=8.8 Hz, 2 H), 7.32-7.34 (m, 1 H), 7.52 (d, J=8.8 Hz, 2 H), 9.96-9.98 (m, 2 H); ESI-MS (relative intensities): 431.9 (M+Na)$^+$ (70%).

Intermediate 2: Methyl 3-(4-(5-methyl-1,3,4-oxadiazol-2-yl)phenoxy)-5-(1-methyl-2-oxo-pyrrolidin-3-yloxy)benzoate To a stirred mixture of Methyl 3-hydroxy-5-(1-methyl-2-oxopyrrolidin-3-yloxy)benzoate (15 g) (Intermediate 3), N,N-dimethylglycine hydrochloride (2.3 g), copper (II) iodide (1 g) in dry 1,4-dioxane was added 2-(4-iodophenyl)-5-methyl-1,3,4-oxadiazole (15.4 g) (Intermediate 4) under nitrogen. The reaction mixture was refluxed for 24 h. The reaction mixture was cooled, quenched with water and extracted with DCM. Combined organic washings were washed with water, brine, dried over $Na_2SO_4$, filtered and concentrated in vacuo to get the crude product. The crude product was purified by column chromatography using silica gel as stationary phase and ethyl acetate: petroleum ether (9:1) as mobile phase to give the product (7 g) as thick liquid.

$^1$H NMR (DMSO-d$_6$, 400 MHz) δ ppm: 1.91-1.98 (m, 1 H), 2.49-2.54 (m, 1 H), 2.56 (s, 3 H), 2.77 (s, 3 H), 3.34-3.41 (m, 2 H), 3.81 (s, 3 H), 5.12 (t, J=7.6 Hz, 1 H), 7.13-7.15 (m, 2 H), 7.22 (d, J=8.8 Hz, 2 H), 7.42 (s, 1 H), 7.97 (d, J=8.8 Hz, 2 H); ESI-MS (relative intensities): 423.9 (M+H)$^+$ (100%), 446.2 (M+Na)$^+$ (30%).

Intermediate 3: Methyl 3-hydroxy-5-(1-methyl-2-oxopyrrolidin-3-yloxy)benzoate To a stirred solution of Methyl 3,5-dihydroxybenzoate (20 g) [CAS No. 2150-44-9] in dry DMF was added potassium carbonate (48 g) and the suspension stirred at ambient temperature under nitrogen. To this 3-Bromo-1-methyl-pyrrolidin-2-one (40 g) (Intermediate 5) [*J. Med. Chem.*, 1987, 30, 1995-98] was added in three equal portions in 4 h intervals at room temperature and stirred overnight at ambient temperature. It was then quenched with water. The aqueous suspension was extracted with DCM. The to combined extracts were washed with water, brine, dried over $Na_2SO_4$, and filtered, concentrated under reduced pressure to get the thick liquid residue. The crude product was purified by column chromatography using silica gel as stationary phase and ethyl acetate: petroleum ether as a mobile phase to yield the product as white solid (15 g).

$^1$H NMR (CDCl$_3$, 400 MHz) δ ppm: 2.08-2.10 (m, 1 H), 2.60-2.67 (m, 1 H), 3.04 (s, 3H), 3.40-3.43 (m, 1 H), 3.48-3.51 (m, 1 H), 3.87 (s, 3 H), 4.91 (t, J=7.2 Hz, 1 H), 6.59-6.61 (m, 1 H), 7.07-7.09 (m, 1 H), 7.09-7.13 (m, 1 H), 8.02 (s, 1 H); ESI-MS (relative intensities): 287.9 (M+Na)$^+$ (30%).

Following examples (Example 2-7) were prepared by using similar procedure as that of example 1 with suitable modifications as are well within the scope of a skilled person.

EXAMPLE 2

3-(4-(5-Methyl-1,3,4-oxadiazol-2-yl)phenoxy)-5-(1-methyl-2-oxopyrrolidin-3-yloxy)-N-(5-methylthiazol-2-yl)benzamide $^1$H NMR (DMSO-d$_6$, 400 MHz) δ ppm: 1.94-1.99 (m, 1 H), 2.35 (s, 3 H), 2.56 (s, 3 H), 2.58-2.61 (m, 1 H), 2.78 (s, 3 H), 3.28-3.39 (m, 1 H), 3.40-3.42 (m, 1 H), 5.14 (t, J=8 Hz, 1 H), 7.00 (t, J=2.0 Hz, 1 H), 7.22 (s, 1 H), 7.23 (d, J=8.4 Hz, 2 H), 7.40 (s, 1 H), 7.60 (s, 1 H), 7.98 (d, J=8.4 Hz, 2 H), 12.47 (bs, 1 H); ESI MS m/z (relative intensities): 506 (M+H)$^+$ (100%); UPLC Purity: 98.4%, Ret.time: 3.80 min.

EXAMPLE 3

Ethyl 2-(2-(3-(4-(5-methyl-1,3,4-oxadiazol-2-yl)phenoxy)-5-(1-methyl-2-oxopyrrolidin-3-yloxy)benzamido)thiazol-5-yl)acetate $^1$H NMR (CDCl$_3$, 400 MHz) δ ppm: 1.27 (t, J=7.2 Hz, 3 H), 2.15-2.20 (m, 1 H), 2.58-2.59 (m, 1 H), 2.60 (s, 3 H), 2.93 (s, 3 H), 3.37-3.43 (m, 1 H), 3.45-3.48 (m, 1 H), 3.69 (s, 2 H), 4.18 (q, J=7.2 Hz, 2 H), 4.96 (t, J=7.6 Hz, 1 H), 6.82 (s, 1 H), 6.97 (t, J=2.4 Hz, 1 H), 7.13 (d, J=8.8 Hz, 2 H), 7.22 (s, 1 H), 7.42 (s, 1 H), 8.02 (d, J=8.8 Hz, 2 H); UPLC Purity: 94.46%, Ret.time: 3.98 min.

EXAMPLE 4

2-(2-(3-(4-(5-Methyl-1,3,4-oxadiazol-2-yl)phenoxy)-5-((1-methyl-2-oxopyrrolidin-3-yl)oxy)benzamido)thiazol-4-yl)acetic acid $^1$H NMR (DMSO-d$_6$, 400 MHz) δ ppm: 1.92-2.01 (m, 1 H), 2.56 (s, 3 H), 2.60-2.65 (m, 1 H), 2.79 (s, 3 H), 3.31-3.34 (m, 1 H), 3.36-3.44 (m, 1 H), 3.62 (s, 2 H), 5.15 (t, J=7.2 Hz, 1 H), 7.02 (s, 1 H), 7.07 (s, 1 H), 7.24 (d, J=8.2 Hz, 2 H), 7.42 (s, 1 H), 7.62 (s, 1 H), 7.98 (d, J=8.4 Hz, 2 H), 12.50 (bs, 1 H), 12.60 (s, 1 H); ESI-MS m/z (relative intensities): 550.11 (M+H)$^+$, (100%), 572.01 (M+Na)$^+$, (15%); UPLC Purity: 92.90%, Ret.time: 3.37 min.

EXAMPLE 5

3-(4-(5-Methyl-1,3,4-oxadiazol-2-yl)phenoxy)-5-((1-methyl-2-oxopyrrolidin-3-yl)oxy)-N-(4-(2-(3-oxomorpholino)ethyl)thiazol-2-yl)benzamide $^1$H NMR (DMSO-d$_6$, 400 MHz) δ ppm: 2.15-2.24 (m, 1 H), 2.56-2.62 (m, 1 H), 2.62 (s, 3 H), 2.93 (s, 3 H), 2.93-2.96 (m, 2 H), 3.25 (t, J=5.2 Hz, 2 H), 3.38-3.44 (m, 1 H), 3.50-3.52 (m, 1 H), 3.68-3.74 (m, 2 H), 3.78 (t, J=5.2 Hz, 2 H), 4.15 (s, 2 H), 4.96 (t, J=6.8 Hz, 1 H), 6.67 (s, 1 H), 6.99 (t, J=2 Hz, 1 H), 7.11 (d, J=8.8 Hz, 2 H), 7.24 (s, 1H), 7.52 (s, 1 H), 8.02 (d, J=8.8 Hz, 2 H); ESI MS m/z (relative intensities): 619.23 (M+H)$^+$ (74%), 641.23 (M+Na)$^+$ (100%); UPLC Purity: 92.90%, Ret.time: 3.009 min.

EXAMPLE 6

N-(4,5-Dihydrothiazol-2-yl)-3-(4-(5-methyl-1,3,4-oxadiazol-2-yl)phenoxy)-5-((1-methyl-2-oxopyrrolidin-3-yl)oxy)benzamide $^1$H NMR (CDCl$_3$, 400 MHz) δ ppm: 2.17-2.23 (m, 1 H), 2.59 (s, 3 H), 2.59-2.62 (m, 1 H), 2.96 (s, 3 H), 3.25 (t, J=4.8 Hz, 2 H), 3.40-3.44 (m, 1 H), 3.52-3.55 (m, 1 H), 3.78 (t, J=4.8 Hz, 2 H), 4.96 (t, J=6.87 Hz, 1 H), 6.68 (s, 1 H), 6.97 (t, J=2 Hz, 1 H), 7.12 (d, J=8.8 Hz, 2 H), 7.48 (s, 1 H), 8.02 (d, J=8.8 Hz, 2 H); UPLC Purity: 98.47%, Ret.time: 3.014 min.

EXAMPLE 7

3-(4-(5-Methyl-1,2,4-oxadiazol-3-yl)phenoxy)-5-((1-methyl-2-oxopyrrolidin-3-yl)oxy)-N-(thiazol-2-yl)benzamide $^1$H NMR (CDCl$_3$, 400 MHz) δ ppm: 2.13-2.21 (m, 1 H), 2.55-2.63 (m, 1 H), 2.65 (s, 3 H), 2.93 (s, 3 H), 3.34-3.36 (m, 1 H), 3.47-3.53 (m, 1 H), 4.94 (t, J=7.6 Hz, 1 H), 6.96-6.99 (m, 2 H), 7.12 (d, J=8.8 Hz, 2 H), 7.29 (s, 1 H), 7.37 (d, J=3.6 Hz, 1 H), 7.45 (s, 1 H), 8.05 (d, J=8.8 Hz, 2 H); ESI MS m/z (relative intensities): 492.14 (M+H)$^+$ (100%), 514.07 (M+Na)$^+$ (83%); UPLC Purity: 97.14%, Ret.time: 4.078 min.

EXAMPLE 8

N-(5-Cyclopropyl-1,3,4-thiadiazol-2-yl)-3-(4-(5-methyl-1,3,4-oxadiazol-2-yl)phenoxy)-5-((1-methyl-2-oxopyrrolidin-3-yl)oxy)benzamide 4-(Dimethylamino)pyridine (DMAP) (0.149 g), N-(3-Dimethylaminopropyl)-N'-ethylcarbodiimide hydrochloride (EDCI.HCl) (0.524 g) were added to a solution of 3-(1-methoxypropan-2-yloxy)-5-(4-(5-methyl-1,3,4-oxadiazol-2-yl)phenoxy)benzoic acid (0.5 g) (Intermediate 1) in dry DCM under nitrogen at 0-5° C. 5-cyclopropyl-1,3,4-thiadiazol-2-amine (0.134 g) was added and the mixture was stirred for 16 h at room temperature. It was diluted with commercially available DCM. Organic phase was washed with dil HCl, saturated solution of NaHCO$_3$, Water, brine, dried over Na$_2$SO$_4$, filtered and concentrated in vacuo to get the crude residue. The residue was chromatographed using silica gel as stationary phase and MeOH: CHCl$_3$ gradient as mobile phase up to yield the product (0.3 g) as a white solid.

$^1$H NMR (CDCl$_3$, 400 MHz) δ ppm: 1.07-1.12 (m, 2 H), 1.12-1.18 (m, 2 H), 2.17-2.20 (m, 1 H), 2.28-2.31 (m, 1 H), 2.58-2.60 (m, 1 H), 2.62 (s, 3 H), 2.93 (s, 3 H), 3.43-3.49 (m, 1 H), 3.51-3.54 (m, 1H), 5.01 (t, J=7.2 Hz, 1 H), 6.96 (t, J=2.4 Hz, 1 H), 7.12 (d, J=8.8 Hz, 2 H), 7.42-7.44 (m, 1 H), 7.22-7.25 (m, 1 H), 8.02 (d, J=8.8 Hz, 2 H); ESI MS m/z (relative intensities): 533.1 (M+H)$^+$, (100%), 555 (M+Na)$^+$ (10%); UPLC Purity: 99.14%, Ret.time: 3.71 min.

Intermediate 3: Methyl 3-(hydroxy)-5-[(1-methyl-2-oxopyrrolidin-3-yl)oxy]benzoate Methyl-3-(benzyloxy)-5-[(1-methyl-2-oxopyrrolidin-3-yl)oxy]benzoate (6.1 g) (Intermediate 6) was dissolved in THF: Methanol mixture (1:1), and 10% Pd/C (0.6 g) was added to this mixture. The reaction mixture was stirred under hydrogen atmosphere for 16 h. After 16 h, TLC showed absence of starting material and formation of polar spot when checked in 10% methanol: chloroform, the reaction mixture was filtered through celite on Buckner funnel. The filtrate was concentrated under vacuum to get the solid product (3.27 g).

$^1$H NMR (CDCl$_3$, 400 MHz) δ ppm: 1.89-1.92 (m, 1 H), 2.51-2.54 (m, 1 H), 2.77 (s, 3 H), 3.34-3.37 (m, 2 H), 3.80 (s, 3 H), 4.96 (t, J=7.2 Hz, 1 H), 6.66 (t, J=2 Hz, 1 H), 6.97 (t, J=1.6 Hz, 1 H), 7.01 (t, J=1.2 Hz, 1 H), 9.88 (s, 1H); ESI MS m/z (relative intensities): 266.2 (M+H)$^+$ (100%); UPLC Purity: 99.00%, Ret. time: 2.67 min.

Intermediate 6: Methyl 3-(benzyloxy)-5-[(1-methyl-2-oxopyrrolidin-3-yl)oxy]benzoate Methyl 3-hydroxy-5-(benzyloxy)benzoate (4.75 g) (CAS No. 54915-31-0] was dissolved in DMF in single necked round bottomed flask fitted with stop cock with N$_{2(g)}$ balloon. Potassium carbonate (8.4 g) was added and reaction was stirred for 15 min. 3-Bromo-1-methyl-pyrrolidine-2-one (4.91 g) (Intermediate 5) [*J. Med. Chem.,* 1987, 30, 1995-98] was added to reaction mixture in three different portions at room temperature. The reaction was stirred at ambient temperature for 16 h and monitored by TLC using 10% methanol: chloroform as mobile phase. After 16 h, TLC showed completion of reaction mixture and formation of one polar spot. The reaction mixture was diluted with ice-cold water and extracted with EtOAc. All organic layers were combined and washed with water, brine, dried over anhydrous sodium sulfate, filtered and concentrated under vacuum to get crude thick liquid product. The crude product was purified by flash column chromatography. The desired product was eluted at 50% of EtOAc: Chloroform. Pure white solid was obtained after column purification (6.1 g).

$^1$H NMR (CDCl$_3$, 400 MHz) δ ppm: 2.07-2.16 (m, 1 H), 2.53-2.61 (m 1 H), 2.88 (s, 3H), 3.34-3.40 (m, 1 H), 3.46-3.51 (m, 1 H), 3.91 (s, 3 H), 4.88 (t, J=7.2 Hz, 1 H), 5.3 (s, 2 H), 6.89 (t, J=2 HZ, 1 H), 7.31-7.38 (m, 3 H), 7.39-7.44 (m, 4 H); ESI MS m/z (relative intensities): 378.0 (M+H)$^+$ (100%); UPLC Purity: 93.27%, Ret.time: 4.31 min.

Following examples (Example 9-12) were prepared by using similar procedure as that of example 1 with suitable modifications as are well within the scope of a skilled person

EXAMPLE 9

3-(4-(5-Methyl-1,3,4-oxadiazol-2-yl)phenoxy)-5-((1-methyl-2-oxopyrrolidin-3-yl)oxy)-N-(pyrazin-2-yl)benzamide $^1$H NMR (DMSO-d$_6$, 400 MHz) δ ppm: 1.96-1.99 (m, 1 H), 2.48-2.52 (m, 1 H), 2.56 (s, 3 H), 2.78 (s, 3 H), 3.34-3.41 (m, 2 H), 5.16 (t, J=7.6 Hz, 1 H), 7.09 (s, 1 H), 7.23 (d, J=8.4 Hz, 2 H), 7.38 (s, 1 H), 7.57 (s, 1 H), 7.99 (d, J=8.8 Hz, 2 H), 8.41 (s, 1 H), 8.46 (s, 1 H), 9.37 (s, 1 H), 11.16 (s, 1 H); UPLC Purity: 97.41%, Ret.time: 3.279 min.

EXAMPLE 10

3-(3-(5-Methyl-1,3,4-oxadiazol-2-yl)phenoxy)-5-((1-methyl-2-oxopyrrolidin-3-yl)oxy)-N-(thiazol-2-yl)benzamide $^1$H NMR (CDCl$_3$, 400 MHz) δ ppm: 2.22-2.26 (m, 1 H), 2.55-2.59 (m, 1 H), 2.61 (s, 3 H), 2.93 (s, 3 H), 3.37-3.43 (m, 1 H), 3.48-3.54 (m, 1 H), 4.96 (t, J=7.6 Hz, 1 H), 6.96 (d, J=2.4 Hz, 1 H), 7.01 (d, J=3.6 Hz, 1 H), 7.20-7.22 (m, 2 H), 7.39-7.42 (m, 1 H), 7.48-7.50 (m, 1 H), 7.62-7.65 (m, 1 H), 7.67-7.68 (m, 1 H), 7.82-7.84 (m, 1 H); ESI-MS m/z (relative intensities): 492.08 (M+H)$^+$ (70%), 514.05 (M+Na)$^+$, (100%); UPLC Purity: 94.41%, Ret.time: 3.63 min.

EXAMPLE 11

3-(3-(2-Amino-1H-benzo[d]imidazole-1-carbonyl)-5-(4-(5-methyl-1,3,4-oxadiazol-2-yl)phenoxy)phenoxy)-1-methylpyrrolidin-2-one $^1$H NMR (DMSO-d$_6$, 400 MHz) δ ppm: 1.95-2.01 (m, 1 H), 2.56 (s, 3 H), 2.58-2.59 (m, 1 H), 2.79 (s, 3 H), 3.34-3.41 (m, 2 H), 5.13 (t, J=7.6 Hz, 1 H), 7.06 (s, 1 H), 7.13-7.15 (m, 2 H), 7.24 (d, J=8.8 Hz, 2 H), 7.40-7.41 (m, 2 H), 7.42 (s, 1 H), 7.63 (s, 1 H), 7.99 (d, J=8.8 Hz, 2 H), 12.29 (s, 2 H).

EXAMPLE 12 tert-Butyl 5-methyl-3-(3-(4-(5-methyl-1,3,4-oxadiazol-2-yl)phenoxy)-5-((1-methyl-2-oxo pyrrolidin-3-yl)oxy)benzamido)-1H-pyrazole-1-carboxylate $^1$H NMR (DMSO-d$_6$, 400 MHz) δ ppm: 1.55 (s, 9 H), 1.9-2.0 (m, 2 H), 2.49 (s, 3 H), 2.56 (s, 3 H), 2.78 (s, 3 H), 3.29-3.40 (m, 2 H), 5.13 (t, J=7.6 Hz, 1 H), 6.76 (s, 1 H), 7.03 (s, 1 H), 7.22 (d, J=8.8 Hz, 2 H), 7.35 (s, 1 H), 7.55 (s, 1 H), 7.98 (d, J=8.8 Hz, 2 H), 11.27 (s, 1 H); ESI-MS m/z (relative intensities): 589.28 (M+H)$^+$ (22%), 611.22 (M+Na)$^+$, (100%); UPLC Purity: 98.02%, Ret.time: 4.31 min.

EXAMPLE 13

3-(4-(5-Methyl-1,3,4-oxadiazol-2-yl)phenoxy)-5-(1-methyl-2-oxopyrrolidin-3-yloxy)-N-(4-methylthiazol-2-yl)benzamide 4-(Dimethylamino)pyridine (DMAP) (0.149 g), N-(3-Dimethylaminopropyl)-N'-ethylcarbodiimide hydrochloride (EDCI.HCl) (0.524 g) were added to a solution of 3-(1-Methoxypropan-2-yloxy)-5-(4-(5-methyl-1,3,4-oxadiazol-2-yl)phenoxy)benzoic acid (0.5 g) (Intermediate 1) in dry DCM under nitrogen at 0-5° C. 2-amino-4-methyl thiazole (0.134 g) was added and the mixture was stirred for 16 h at room temperature. It was diluted with commercially available DCM. Organic phase was washed with dil HCl, saturated solution of NaHCO$_3$, water, brine, dried over Na$_2$SO$_4$, filtered and concentrated in vacuo to get the crude residue. The residue was chromatographed to yield pure titled compound (0.3 g) as a white solid.

$^1$H NMR (DMSO-d$_6$, 400 MHz) δ ppm: 1.90-1.99 (m, 1 H). 2.28 (s, 3 H), 2.58 (s, 3 H), 2.60-2.66 (m, 1 H), 2.79 (s, 3 H), 3.28-3.39 (m, 1 H), 3.40-3.43 (m, 1 H), 5.14 (t, J=7.6 Hz, 1 H), 6.81 (s, 1 H), 7.00 (s, 1 H), 7.23 (d, J=7.2 Hz, 2 H), 7.40 (s, 1 H), 7.61 (s, 1 H), 7.99 (d, J=6.8 Hz, 2 H), 12.58 (s, 1 H); ESI MS m/z (relative intensities): 506 (M+H)$^+$, (100%); UPLC Purity: 99.7%, Ret.time: 3.795 min.

Intermediate 2: Methyl 3-[4-(5-methyl-1,3,4-oxadiazol-2-yl)phenoxy]-5-[(1-methyl-2-oxo-pyrrolidin-3-yl)oxy]-benzoate To a stirring solution of Methyl 3-hydroxy-5-[4-(5-methyl-1,3,4-oxadiazol-2-yl)phenoxy]benzoate (4 g) (Intermediate 7) in dry DMF, 3-Bromo-1-methyl-pyrrolidine-2-one (4.12 g) (Intermediate 5) [J. Med. Chem., 1987, 30, 1995-98] was added under nitrogen atmosphere at room temperature in three portions at 4 h interval. The reaction mixture was stirred at room temperature for 16 h and then warmed to 45-50° C. for 3 h. The reaction was monitored by TLC. After completion, reaction mixture was diluted with ice cold water and extracted with EtOAc. All organic layers were combined and washed with water, brine, dried over anhydrous sodium sulphate, filtered and concentrated under vacuum to get crude thick liquid product. Crude residue was chromatographed to yield pure compound (5.2 g).

$^1$H NMR (DMSO-d$_6$, 400 MHz) δ ppm: 1.91-1.98 (m, 1 H), 2.49-2.54 (m, 1 H), 2.56 (s, 3 H), 2.77 (s, 3 H), 3.34-3.41 (m, 2 H), 3.81 (s, 3 H), 5.12 (t, J=7.6 Hz, 1 H), 7.13-7.15 (m, 2 H), 7.22 (d, J=8.8 Hz, 2 H), 7.42 (s, 1 H), 7.97 (d, J=8.8 Hz, 2 H); ESI MS m/z (relative intensities): 424.14 (M+H)$^+$ (100%), 446.13 (M+Na)$^+$ (80%); UPLC Purity: 95.89%, Ret. time: 3.687 min.

Intermediate 7: Methyl 3-hydroxy-5-[4-(5-methyl-1,3,4-oxadiazol-2-yl)phenoxy]benzoate To a solution of Methyl 3-(benzyloxy)-5-[4-(5-methyl-1,3,4-oxadiazol-2-yl)phenoxy]benzoate (28 g) (Intermediate 8) in glacial acetic acid, suspension of 10% Pd/C in glacial acetic acid was added in Parr hydrogenation apparatus. The reaction was subjected under 60 PSI of hydrogen for 6 h. After completion, the reaction mixture was filtered to remove catalyst. Filtrate was poured into ice, the solid obtained was filtered, washed with water, saturated sodium bicarbonate solution, water, petroleum ether, air dried to obtain desired product (18 g, 70%).

$^1$H NMR (CDCl$_3$, 400 MHz) δ ppm: 2.56 (s, 3 H), 3.79 (s, 3 H), 6.75-6.76 (m, 1 H), 6.99 (d, J=8.8 HZ, 2 H), 7.28 (s, 1 H), 7.38 (s, 1 H), 7.99 (d, J=8.8 Hz, 2 H), 10.24 (bs, 1 H); ESI MS m/z (relative intensities): 327.17 (M+1)$^+$ (90%), 349.14 (M+Na)$^+$ (100%) UPLC Purity: 97.40%, Ret.time: 3.661 min.

Intermediate 8: Methyl 3-(benzyloxy)-5-[4-(5-methyl-1,3,4-oxadiazol-2-yl)phenoxy]benzoate To a stirring solution of Methyl 3-[4-(2-acetylhydrazinecarbonyl)phenoxy]-5-(benzyloxy)benzoate (32 g) (Intermediate 9) in dry toluene was added thionyl chloride (10.5 g) drop wise at room temperature under nitrogen atmosphere. The reaction was refluxed and monitored by TLC. After completion of the reaction, reaction mixture was diluted with water and extracted with EtOAc. All organic layers were combined and washed with saturated sodium bicarbonate solution, water, and brine, dried over anhydrous sodium sulphate, filtered and concentrated under vacuum to get crude pale yellow solid (30 g). The crude compound was purified by solvent trituration.

$^1$H NMR (CDCl$_3$, 400 MHz) δ ppm: 2.61 (s, 3 H), 3.90 (s, 3 H), 5.09 (s, 2 H), 6.87-6.88 (m, 1 H), 7.08 (d, J=8.8 Hz, 2 H), 7.32-7.33 (m, 1 H), 7.34-7.43 (m, 5 H), 7.48-7.49 (m, 1 H), 8.00 (d, J=8.8 Hz, 2 H); ESI MS m/z (relative intensities): 417.18, (M+H)$^+$, (100%), 439.17 (M+Na)$^+$ (80%) UPLC Purity: 93.98%, Ret.time: 5.218 min.

Intermediate 9: Methyl 3-[4-(2-acetylhydrazinecarbonyl)phenoxy]-5-(benzyloxy)benzoate To a stirring solution of 4-[3-(Benzyloxy)-5-(methoxycarbonyl)phenoxy]benzoic acid (30 g) (Intermediate 10) in dry DCM in a round bottomed flask, DMF (1.5 mL, catalytic) was added under N₂ atmosphere. Oxalyl chloride (20.1 g) was added slowly drop wise to the reaction mixture at 0-5° C. After complete conversion of the acid to its acid chloride, volatile material was removed under vacuum on rotary evaporator.

Residue thus obtained was dissolved in DCM and transferred to the solution of acetichydrazide (8.8 g) and pyridine (12.4 mL) in dry DCM at 0-5° C. under nitrogen atmosphere. Reaction was brought to room temperature and stirred for 15 minutes. The reaction mixture was diluted with dil. HCl (1N) and DCM. Layers were separated, organic layer was washed with water, brine, dried over anhydrous sodium sulphate, filtered and concentrated under vacuum to get pure white solid. $^1$H NMR (CDCl$_3$, 400 MHz) δ ppm: 2.12 (s, 3 H), 3.88 (s, 3 H), 5.08 (s, 2 H), 6.85 (s, 1 H), 6.99 (d, J=8 Hz, 2 H), 7.29-7.28 (m, 1 H), 7.42-7.33 (m, 5 H), 7.48-7.49 (m, 1 H), 7.80 (d, J=8.4 Hz, 2 H), 8.81 (d, J=5.6 Hz, 1 H), 9.15 (d, J=5.2 Hz, 1 H); ESI MS m/z (relative intensities): 435.20, (M+H)$^+$ (35%), 457.13 (M+Na)$^+$ (15%); UPLC Purity: 98.88, Ret.time: 4.198 min.

Intermediate 10: 4-[3-(benzyloxy)-5-(methoxycarbonyl)phenoxy]benzoic acid

To a stirring solution of Methyl 3-(benzyloxy)-5-(4-formylphenoxy)benzoate (30 g) (Intermediate 11) in acetone, Jones reagent was added drop wise at 0° C. until the brown color persists in the reaction mixture. After completion of the reaction mixture was diluted with water and extracted with DCM. All organic layers were combined and washed with water, brine, dried over anhydrous sodium sulphate, filtered and concentrated under vacuum to get pure white solid (30 g).
$^1$H NMR (CDCl$_3$, 400 MHz) δ ppm: 3.90 (s, 3 H), 5.1 (s, 2 H), 6.88 (t, J=2 Hz, 1 H), 7.02 (d, J=8.8 Hz, 2 H), 7.32-7.36 (m, 2 H), 7.37-7.43 (m, 4 H), 7.51 (s, 1 H), 8.09 (d, J=8.8 Hz, 2 H); ESI MS m/z (relative intensities): 377.2 (M−1) (100%); UPLC Purity: 99.08%, Ret.time: 4.99 min.

Intermediate 11: Methyl 3-(benzyloxy)-5-(4-formylphenoxy)benzoate

To a single necked round bottomed flask fitted with stop cock with N$_{2(g)}$ balloon, in DMF was added Methyl 3-(benzyloxy)-5-hydroxybenzoate (24 g) (Intermediate 12). Under stirring, potassium carbonate (38 g) followed by 4-fluorobenzaldehyde (13.84 g) were added at room temperature. The reaction was heated at 90° C. for 16 h with constant stirring. The reaction mixture was diluted with water and extracted with EtOAc. All organic layers were combined and washed with water, brine, dried over anhydrous sodium sulphate, filtered and concentrated under vacuum to get crude thick liquid product. The crude product was purified by flash column chromatography to yield title compound (32.5 g).
$^1$H NMR (CDCl$_3$, 400 MHz) δ ppm: 3.90 (s, 3 H), 5.10 (s, 2 H), 6.89 (t, J=2 Hz, 1 H), 7.07 (d, J=8.8 Hz, 2 H), 7.32-7.37 (m, 3 H), 7.38-7.41 (m, 2 H), 7.41-7.43 (m, 1 H), 7.52 (s, 1 H), 7.86 (d, J=8.8 Hz, 2 H), 9.94 (s, 1 H); UPLC Purity: 98.84%, Ret.time: 5.42 min.

Intermediate 12: Methyl 3-(benzyloxy)-5-hydroxybenzoate

Methyl-3,5-dihydroxy benzoate (20 g) [CAS No. 2150-44-9] in dry DMF was taken in a round bottomed flask with constant stirring. Under nitrogen atmosphere, potassium carbonate (24.9 g) followed by benzyl bromide (28.4 g) at room temperature were added. The reaction was stirred at the same temperature for 16 h. After completion, reaction mixture was diluted with water and extracted with EtOAc. All organic layers were combined and washed with water, brine, dried over anhydrous sodium sulphate, filtered and concentrated under vacuum to get crude thick liquid product. Crude product was purified by flash chromatography to furnish desired product. (10.2 g).
$^1$H NMR (CDCl$_3$, 400 MHz) δ ppm: 3.90 (s, 3 H), 5.07 (s, 2 H), 6.68 (t, J=2 Hz, 1 H), 7.14 (t, J=2 Hz, 1 H), 7.26 (s, 1 H), 7.44-7.31 (m, 5 H); UPLC Purity: 98.30%, Ret.time: 4.278 min.

Following examples (Example 14-67) were prepared by using similar procedure as that of example 1 with suitable modifications as are well within the scope of a skilled person

EXAMPLE 14

N-(Benzo[d] thiazol-2-yl)-3-(4-(5-methyl-1,3,4-oxadiazol-2-yl)phenoxy)-5-((1-methyl-2-oxopyrrolidin-3-yl)oxy)benzamide $^1$H NMR (DMSO-d$_6$, 400 MHz) δ ppm: 1.98-2.03 (m, 1 H), 2.56 (s, 3 H), 2.56-2.57 (m, 1 H), 2.79 (s, 3 H), 3.30-3.42 (m, 2 H), 5.17 (t, J=6 Hz, 1 H), 7.11 (t, J=2 Hz, 1H), 7.25 (d, J=7.2 Hz, 2 H), 7.34 (t, J=8 Hz 1 H), 7.43-7.47 (m, 2 H), 7.66 (s, 1 H), 7.80-7.81 (m, 1 H), 7.99 (d, J=8.8 Hz, 3 H); ESI MS m/z (relative intensities): 542.1 (M+H)$^+$ (100%); UPLC Purity: 95.78%, Ret.time: 4.310 min.

EXAMPLE 15

2-(3-(4-(5-Methyl-1,3,4-oxadiazol-2-yl)phenoxy)-5-((1-methyl-2-oxopyrrolidin-3-yl)oxy)benzamido) thiazole-5-carboxylic acid $^1$H NMR (DMSO-d$_6$, 400 MHz) δ ppm: 1.98-2.00 (m, 1 H), 2.61-2.65 (m, 4 H), 2.78 (s, 3 H), 3.36-3.43 (m, 2 H), 5.14 (t, J=7.6 Hz, 1 H), 7.11 (s, 1 H), 7.24 (d, J=8.8 Hz, 2 H), 7.37 (s, 1 H), 7.64 (s, 1 H), 8.01 (d, J=8.8 Hz, 2 H), 8.11 (s, 1 H), 13.16 (bs, 2 H); UPLC Purity: 96.46%, Ret.time: 3.317 min.

EXAMPLE 16

3((1-Isopropyl-2-oxopyrrolidin-3-yl)oxy)-5-(4-(5-methyl-1,3,4-oxadiazol-2-yl)phenoxy)-N-(4-methylthiazol-2-yl)benzamide $^1$H NMR (CDCl$_3$, 400 MHz) δ ppm: 1.17 (d, J=7.2 Hz, 3 H). 1.20 (d, J=6.8 Hz, 3 H), 2.07-2.16 (m, 1 H), 2.25 (s, 3 H), 2.53-2.59 (m, 1 H), 2.61 (s, 3 H), 3.28-3.34 (m, 1 H), 3.43-3.49 (m, 1 H), 4.36-4.44 (m, 1 H), 4.91 (t, J=7.2 Hz, 1 H), 6.55 (s, 1 H), 6.98 (t, J=2.4 Hz, 1 H), 7.11 (d, J=8.8 Hz, 2 H), 7.21 (s, 1 H), 7.43 (s, 1 H), 8.00 (d, J=8.8 Hz, 2 H); ESI MS m/z (relative intensities): 534.20 (M+H)$^+$ (55%), 556.13 (M+Na)$^+$ (100%); UPLC Purity: 99.48%, Ret.time: 4.196 min.

EXAMPLE 17

3((1-Isopropyl-2-oxopyrrolidin-3-yl)oxy)-5-(4-(5-methyl-1,3,4-oxadiazol-2-yl)phenoxy)-N-(5-methylthiazol-2-yl)benzamide $^1$H NMR (CDCl$_3$, 400 MHz): 1.17 (d, J=6.8 Hz, 3 H), 1.20 (d, J=6.8 Hz, 3 H), 2.10-2.16 (m, 1 H), 2.40 (s, 3 H), 2.56-2.60 (m, 1 H), 2.62 (s, 3 H), 3.29-3.35 (m, 1 H), 3.44-3.49 (m, 1 H), 4.37-4.42 (m, 1 H), 4.97 (t, J=6.8 Hz, 1 H), 6.99 (t, J=2.0 Hz, 1 H), 7.03 (s, 1 H), 7.12 (d, J=8.4 Hz, 2 H); 7.30 (t, J=1.6 Hz, 1 H), 7.47 (s, 1 H), 8.01 (d, J=8.8 Hz, 2 H); ESI MS m/z (relative intensities): 534.20 (M+H)$^+$ (52%), 556.13 (M+Na)$^+$ (100%) UPLC Purity: 96.76%, Ret.time: 4.197 min.

EXAMPLE 18

3((1-Isopropyl-2-oxopyrrolidin-3-yl)oxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 1.17 (d, J=6.8 Hz, 3 H), 1.20 (d, J=6.8 Hz, 3H), 2.11-2.16 (m, 1 H), 2.55-2.60 (m, 1 H), 2.62 (s, 3 H), 3.29-3.35 (m, 1 H), 3.44-3.50 (m, 1 H), 4.37-4.44 (m, 1 H), 4.96 (t, J=7.2 Hz, 1 H), 7.01-6.99 (m, 2 H), 7.12 (d, J=8.8 Hz, 2 H), 7.29 (t, J=2.0 Hz, 1 H), 7.38 (d, J=3.6 Hz, 1 H), 7.48 (s, 1 H), 8.01 (d, J=8.8 Hz, 2 H); ESI MS m/z (relative intensities): 520.13 (M+H)$^+$ (50%), 542.13 (M+Na)$^+$ (100%); UPLC Purity: 97.85%, Ret.time: 4.002 min.

EXAMPLE 19

3((1-Cyclopropyl-2-oxopyrrolidin-3-yl)oxy)-5-(4-(5-methyl-1,3,4-oxadiazol-2-yl)phenoxy)-N-(4-methylthiazol-2-yl)benzamide $^1$H NMR (CDCl$_3$, 400 MHz) δ ppm: 0.69-0.75 (m, 1 H), 0.78-0.89 (m, 3 H), 2.07-2.16 (m, 1 H), 2.29 (s, 3 H), 2.52-2.56 (m, 1 H), 2.61 (s, 3 H), 2.71-2.74 (m, 1 H), 3.28-3.34 (m, 1 H), 3.40-3.45 (m, 1 H), 4.91 (t, J=7.2 Hz, 1 H), 6.55 (s, 1 H), 6.98 (t, J=2.0 Hz, 1 H), 7.12 (d, J=8.4 Hz, 2 H), 7.24 (bs, 1 H), 7.44 (s, 1 H), 8.01 (d, J=8.4 Hz, 2 H); ESI MS m/z (relative intensities): 532.18 (M+H)$^+$ (55%), 554.11 (M+Na)$^+$, (100%); UPLC Purity: 97.44%, Ret.time: 4.049 min.

EXAMPLE 20

3((1-Cyclopropyl-2-oxopyrrolidin-3-yl)oxy)-5-(4-(5-methyl-1,3,4-oxadiazol-2-yl)phenoxy)-N-(5-methylthiazol-2-yl)benzamide $^1$H NMR (CDCl$_3$, 400 MHz) δ ppm: 0.70-0.73 (m, 1 H), 0.80-0.85 (m, 3 H), 2.10-2.14 (m, 1 H), 2.39 (s, 3 H), 2.52-2.56 (m, 1 H), 2.61 (s, 3 H), 2.70-2.74 (m, 1 H), 3.30-3.32 (m, 1 H), 3.39-3.42 (m, 1 H), 4.89 (t, J=7.6 Hz, 1 H), 6.98-7.01 (m, 2H), 7.11 (d, J=8.8 Hz, 2 H), 7.23 (s, 1 H), 7.40 (s, 1 H), 8.01 (d, J=8.8 Hz, 2 H); ESI MS m/z (relative intensities): 532.11 (M+H)$^+$, (43%), 554.11 (M+Na)$^+$, (100%); UPLC Purity: 99.01%, Ret.time: 4.052 min.

EXAMPLE 21

3((1-Cyclopropyl-2-oxopyrrolidin-3-yl)oxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 0.69-0.74 (m, 1 H), 0.77-0.89 (m, 3 H), 2.10-2.15 (m, 1 H), 2.52-2.59 (m, 1 H), 2.62 (s, 3 H), 2.71-2.74 (m, 1 H), 3.28-3.34 (m, 1 H), 3.40-3.45 (m, 1 H), 4.92 (t, J=7.2 Hz, 1 H), 6.9-7.00 (m, 2 H), 7.12 (d, J=8.8 Hz, 2 H), 7.28 (t, J=1.6 Hz, 1 H), 7.37 (d, J=3.6 Hz, 1 H), 7.46 (s, 1 H), 8.01 (d, J=8.8 Hz, 2 H); ESI MS m/z (relative intensities): 518.12 (M+H)$^+$, (100%), 540.12 (M+Na)$^+$, (50%); UPLC Purity: 97.19%, Ret.time: 3.857 min.

EXAMPLE 22

3-(4-(5-Methyl-1,2,4-oxadiazol-3-yl)phenoxy)-5-((1-methyl-2-oxopyrrolidin-3-yl)oxy)-N-(4-methylthiazol-2-yl)benzamide $^1$H NMR (CDCl$_3$, 400 MHz) δ ppm: 2.12-2.20 (m, 1 H), 2.28 (s, 3 H), 2.54-2.62 (m, 1 H), 2.65 (m, 3 H), 2.93 (s, 3 H), 3.36-3.42 (m, 1 H), 3.47-3.52 (m, 1 H), 4.88 (t, J=6.8 Hz, 1 H), 6.55 (d, J=0.8 Hz, 1 H), 6.97 (d, J=1.2 Hz, 1 H), 7.11 (d, J=8.8 Hz, 2 H), 7.17 (t, J=1.6 Hz, 1 H), 7.39 (s, 1 H), 8.06 (d, J=8.8 Hz, 2 H); ESI MS m/z (relative intensities): 506.14 (M+H)$^+$, (100%), 528.14 (M+Na)$^+$, (70%); UPLC Purity: 98.84%, Ret.time: 4.264 min.

EXAMPLE 23

3-(4-(5-Methyl-1,2,4-oxadiazol-3-yl)phenoxy)-5-((1-methyl-2-oxopyrrolidin-3-yl)oxy)-N-(5-methylthiazol-2-yl)benzamide $^1$H NMR (CDCl$_3$, 400 MHz) δ ppm: 2.12-2.20 (m, 1 H), 2.39 (s, 3 H), 2.54-2.62 (m, 1 H), 2.65 (s, 3 H), 2.93 (s, 3 H), 3.36-3.42 (m, 1 H), 3.47-3.52 (m, 1 H), 4.90 (t, J=6.2 Hz, 1 H), 6.96 (t, J=2.0 Hz, 1 H), 7.00 (d, J=1.2 Hz, 1 H), 7.11 (d, J=8.8 Hz, 2 H), 7.22 (d, J=1.6 Hz, 1 H), 7.52 (s, 1 H), 8.06 (d, J=8.8 Hz, 2 H); ESI MS m/z (relative intensities): 506.14 (M+H)$^+$, (100%), 528.14 (M+Na)$^+$ (70%); UPLC Purity: 98.67%, Ret.time: 4.269 min.

EXAMPLE 24

3-(4-(5-Methyl-1,2,4-oxadiazol-2-yl)phenoxy)-N-(5-methyl-1H-pyrazol-3-yl)-5-((1-methyl-2-oxopyrrolidin-3-yl)oxy)benzamide $^1$H NMR (DMSO-d$_6$, 400 MHz) δ ppm: 1.92-1.98 (m, 1 H), 2.20 (s, 3 H), 2.56 (s, 3 H), 2.57-2.61 (m, 1 H), 2.78 (s, 3 H), 3.32-3.43 (m, 2 H), 5.13 (t, J=7.6 Hz, 1 H), 6.36 (s, 1 H), 7.00 (s, 1 H), 7.21 (d, J=8.8 Hz, 2 H), 7.31 (s, 1 H), 7.51 (s, 1 H), 7.98 (d, J=2 Hz, 2 H), 10.72 (s, 1 H), 12.11 (s, 1 H); UPLC Purity: 96.6%, Ret.time: 3.09 min.

EXAMPLE 25

Ethyl 2-(3-(4-(5-methyl-1,3,4-oxadiazol-2-yl)phenoxy)-5-((1-methyl-2-oxopyrrolidin-3-yl)oxy)benzamido)thiazole-5-carboxylate $^1$H NMR (CDCl$_3$, 400 MHz) δ ppm: 1.30 (t, J=7.2 Hz, 3 H), 2.17-2.25 (m, 1 H), 2.56-2.62 (m, 1 H), 2.62 (s, 3 H), 2.78 (s, 3 H), 3.38-3.44 (m, 1 H), 3.50-3.56 (m, 1 H), 4.27 (q, J=7.2 Hz, 2 H), 5.14 (t, J=6.4 Hz, 1 H), 6.98 (t, J=2 Hz, 1 H), 7.12 (d, J=8.8 Hz, 2 H), 7.29 (s, 1 H), 7.48 (s, 1 H), 8.01 (d, J=8.8 Hz, 2 H), 8.10 (s, 1 H); ESI MS m/z (relative intensities): 564.14 (M+H)$^+$ (45%), 586.15 (M+Na)$^+$ (100%); UPLC Purity: 92.46%, Ret.time: 4.118 min.

EXAMPLE 26

Ethyl 2-(3-(4-(5-methyl-1,3,4-oxadiazol-2-yl)phenoxy)-5-((1-methyl-2-oxopyrrolidin-3-yl)oxy)benzamido)thiazole-4-carboxylate $^1$H NMR (CDCl$_3$, 400 MHz) δ ppm: 1.39 (t, J=7.2 Hz, 3 H) 2.15-2.24 (m, 1 H), 2.57-2.64 (m, 1 H), 2.63 (s, 3 H), 2.94 (s, 3 H), 3.39-3.45 (m, 1 H), 3.49-3.55 (m, 1 H), 4.39 (q, J=7

Hz, 2 H), 4.97 (t, J=6.8 Hz, 1 H), 7.01 (t, J=2 Hz, 1 H), 7.15 (d, J=8.8 Hz, 2 H), 7.17 (s, 1 H), 7.42 (s, 1 H), 7.86 (s, 1 H), 8.03 (d, J=8.8 Hz, 2 H); ESI MS m/z (relative intensities): 564.14 (M+H)$^+$ (30%), 586.15 (M+Na)$^+$ (100%); UPLC Purity: 95.78%, Ret.time: 4.027 min.

EXAMPLE 27

3-(4-(5-Ethyl-1,3,4-oxadiazol-2-yl)phenoxy)-5-((1-methyl-2-oxopyrrolidin-3-yl)oxy)-N-(4-methylthiazol-2-yl)benzamide $^1$H NMR (CDCl$_3$, 400 MHz) δ ppm: 1.44 (t, J=7.6 Hz, 3 H), 2.11-2.19 (m, 1 H), 2.27 (s, 3 H), 2.57-2.64 (m, 1 H), 2.93 (s, 3 H), 2.93-2.96 (m, 2 H), 3.36-3.43 (m, 1 H), 3.47-3.52 (m, 1 H), 4.94 (t, J=7.2 Hz, 1 H), 6.55 (s, 1 H), 6.98 (t, J=2 Hz, 1 H), 7.12 (d, J=8.4 Hz, 2 H), 7.27 (s, 1 H), 7.47 (s, 1 H), 8.02 (d, J=8.8 Hz, 2 H); UPLC Purity: 97.35%, Ret.time: 4.02 min.

EXAMPLE 28

3-(4-(5-Isobutyl-1,3,4-oxadiazol-2-yl)phenoxy)-5-((1-methyl-2-oxopyrrolidin-3-yl)oxy)-N-(thiazol-2-yl)benzamide $^1$H NMR (CDCl$_3$, 400 MHz) δ ppm: 0.97 (d, J=6.4 Hz, 6 H), 1.94-1.99 (m, 1 H), 2.11-2.15 (m, 1 H), 2.58-2.61 (m, 1 H), 2.79 (s, 3 H), 2.81 (d, J=7.2 Hz, 2 H), 3.35-3.42 (m, 2 H), 5.15 (t, J=7.2 Hz, 1 H), 7.08 (t, J=2 Hz, 1 H), 7.25 (d, J=8.8 Hz, 2 H), 7.28 (d, J=3.2 Hz, 1 H), 7.41 (s, 1 H), 7.55 (d, J=3.6 Hz, 1 H), 7.62 (s, 1 H), 8.01 (d, J=8.8 Hz, 2 H), 12.66 (bs, 1 H); ESI MS m/z (relative intensities): 534.2 (M+H)$^+$, (65%), 556.13 (M+Na)$^+$, (100%) UPLC Purity: 96.56%, Ret.time: 4.38 min.

EXAMPLE 29

3-(4-(5-Ethyl-1,3,4-oxadiazol-2-yl)phenoxy)-5-((1-methyl-2-oxopyrrolidin-3-yl)oxy)-N-(thiazol-2-yl)benzamide $^1$H NMR (DMSO-d$_6$, 400 MHz) δ ppm: 1.33 (t, J=7.6 Hz, 3 H), 1.93-2.02 (m, 1 H), 2.56-2.62 (m, 1 H), 2.79 (s, 3 H), 2.92 (q, J=7.6 Hz, 2 H), 3.35-3.43 (m, 2 H), 5.15 (t, J=7.2 Hz, 1 H), 7.08 (s, 1 H), 7.24 (d, J=8.8 Hz, 2 H), 7.28 (d, J=3.6 Hz, 1 H), 7.42 (s, 1 H), 7.54 (d, J=3.6 Hz, 1 H), 7.62 (s, 1 H), 8.01 (d, J=8.8 Hz, 2 H), 12.65 (bs, 1 H); UPLC Purity: 96.50%, Ret.time:=3.83 min.

EXAMPLE 30

3-(4-(5-Isobutyl-1,3,4-oxadiazol-2-yl)phenoxy)-5-((1-methyl-2-oxopyrrolidin-3-yl)oxy)-N-(4-methylthiazol-2-yl)benzamide $^1$H NMR (CDCl$_3$, 400 MHz) δ ppm: 1.06 (d, J=6.8 Hz, 6 H), 2.14-2.25 (m, 2 H), 2.27 (s, 3 H), 2.54-2.62 (m, 1 H), 2.82 (d, J=7.2 Hz, 2 H), 2.93 (s, 3 H), 3.36-3.43 (m, 1 H); 3.47-3.53 (m, 1 H), 4.87 (t, J=7.2 Hz, 1 H), 6.56 (s, 1 H), 6.98 (t, J=2 Hz, 1 H), 7.12 (d, J=8.8 Hz, 2 H), 7.18 (s, 1 H), 7.41 (s, 1 H), 8.03 (d, J=8.8 Hz, 2 H), 10.2 (bs, 1 H); UPLC Purity: 99.74%, Ret.time: 4.60 min.

EXAMPLE 31

3-((1-Methyl-2-oxopyrrolidin-3-yl)oxy)-N-(4-methylthiazol-2-yl)-5-(4-(5-phenyl-1,3,4-oxadiazol-2-yl)phenoxy)benzamide $^1$H NMR (CDCl$_3$, 400 MHz) δ ppm: 2.13-2.21 (m, 1 H), 2.28 (s, 3 H), 2.55-2.64 (m, 1 H), 2.94 (s, 3 H), 3.37-3.43 (m, 1 H), 3.47-3.53 (m, 1 H), 4.93 (t, J=7.2 Hz, 1 H), 6.56 (s, 1 H), 7.01 (t, J=2 Hz, 1 H), 7.15 (d, J=8.8 Hz, 2 H), 7.21 (s, 1 H), 7.43 (s, 1 H), 7.52-7.56 (m, 3 H), 8.13-8.16 (m, 4 H); ESI MS m/z (relative intensities): 568.67 (M+H)$^+$ (100%); UPLC Purity: 98.51%, Ret.time:=4.69 min.

EXAMPLE 32

3-(4-(5-Cyclopropyl-1,3,4-oxadiazol-2-yl)phenoxy)-5-((1-methyl-2-oxopyrrolidin-3-yl)oxy)-N-(thiazol-2-yl)benzamide $^1$H NMR (CDCl$_3$, 400 MHz) δ ppm: 1.22-1.39 (m, 4 H), 2.13-2.26 (m, 2 H), 2.55-2.63 (m, 1 H), 2.96 (s, 3 H), 3.37-3.43 (m, 1 H), 3.47-3.53 (m, 1 H), 4.92 (t, J=7.2 Hz, 1H), 6.99-7.01 (m, 2 H), 7.11 (d, J=8.8 Hz, 2 H), 7.25 (s, 1 H), 7.35 (d, J=3.6 Hz, 1H), 7.44 (d, J=2 Hz, 1 H), 7.99 (d, J=8.8 Hz, 2 H); ESI MS m/z (relative intensities): 518.67 (M+H)$^+$, (65%) 540.67 (M+Na)$^+$, (100%); UPLC Purity: 97.98%, Ret.time: 3.92 min.

EXAMPLE 33

3-(4-(5-Cyclopropyl-1,3,4-oxadiazol-2-yl)phenoxy)-5-((1-methyl-2-oxopyrrolidin-3-yl)oxy)-N-(4-methylthiazol-2-yl)benzamide $^1$H NMR (CDCl$_3$, 400 MHz) δ ppm: 1.18-1.25 (m, 4 H), 2.17-2.25 (m, 2 H), 2.30 (s, 3H), 2.57-2.61 (m, 1 H), 2.94 (s, 3 H), 3.39-3.43 (m, 1 H), 3.47-3.53 (m, 1 H), 4.91 (t, J=7.2 Hz, 1 H), 6.56 (s, 1 H), 6.99 (t, J=2 Hz, 1 H), 7.11 (d, J=8.8 Hz, 2 H), 7.17 (s, 1H), 7.41 (s, 1 H), 7.99 (d, J=8.8 Hz, 2 H); ESI MS m/z (relative intensities): 532.53 (M+H)$^+$, (75%), 554.6 (M+Na)$^+$, (100%) UPLC Purity: 98.06%, Ret.time: 4.09 min.

EXAMPLE 34

3((1-Methyl-2-oxopyrrolidin-3-yl)oxy)-5-(4-(5-phenyl-1,3,4-oxadiazol-2-yl)phenoxy)-N-(thiazol-2-yl)benzamide $^1$H NMR (CDCl$_3$, 400 MHz) δ ppm: 2.06-2.22 (m, 1 H), 2.58-2.62 (m, 1 H), 2.94 (s, 3 H), 3.37-3.43 (m, 1 H), 3.49-3.54 (m, 1 H), 4.95 (t, J=7.2 Hz, 1 H), 7.00-7.03 (m, 2 H), 7.16 (d, J=8.8 Hz, 2 H), 7.30 (s, 1 H), 7.38 (d, J=3.3 Hz, 1 H), 7.39 (s, 1 H), 7.52-7.56 (m, 3 H), 8.13-8.16 (m, 4 H); ESI MS m/z (relative intensities): 554.60 (M+H)$^+$, (100%) 576.61 (M+Na)$^+$, (90%); UPLC Purity: 98.63%, Ret.time: 4.52 min.

EXAMPLE 35

3((1-Ethyl-2-oxopyrrolidin-3-yl)oxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 1.15 (t, J=7.2 Hz 3 H), 2.12-2.19 (m, 1 H), 2.59-2.63 (m, 1 H), 2.61 (s, 3 H); 3.36-3.44 (m, 3 H), 3.47-3.52 (m, 1 H), 4.97 (t, J=7.6 Hz, 1 H), 7.01-6.99 (m, 2 H), 7.13 (d, J=8.8 Hz, 2 H), 7.32 (s, 1 H), 7.38

(d, J=3.6 Hz, 1H), 7.48 (s, 1 H), 8.02 (d, J=8.8 Hz, 2 H); ESI MS m/z (relative intensities): 506.1 (M+H)$^+$, (50%), 528.2 (M+Na)$^+$, (100%); UPLC Purity: 95.93%, Ret.time: 3.784 min.

EXAMPLE 36

3((1-Cyclohexyl-2-oxopyrrolidin-3-yl)oxy)-5-(4-(5-methyl-1,3,4-oxadiazol-2-yl)phenoxy)-N-(thiazol-2-yl)benzamide $^1$H NMR (CDCl$_3$, 400 MHz) δ ppm: 1.31-1.43 (m, 4 H), 1.67-1.82 (m, 6 H), 2.08-2.14 (m, 1 H), 2.55-2.60 (m, 1 H), 2.61 (s, 3 H), 3.31-3.35 (m, 1 H), 3.44-3.49 (m, 1 H), 3.91-3.97 (m, 1 H), 4.93 (t, J=7.6 Hz 1 H), 6.98 (d, J=3.6 Hz, 1 H), 7.00 (t, J=2.0 Hz, 1 H), 7.11 (d, J=8.8 Hz, 2 H), 7.28 (s, 1 H), 7.30 (d, J=3.6 Hz 1 H), 7.46 (s, 1 H), 8.01 (d, J=8.8 Hz, 2 H); ESI MS m/z (relative intensities): 560.1 (M+H)$^+$, (90%), 582.3 (M+Na)$^+$, (60%); UPLC Purity: 96.63% Ret.time: 4.567 min.

EXAMPLE 37

3-(4-(5-Methyl-1,3,4-oxadiazol-2-yl)phenoxy)-5-((1-methyl-2-oxopyrrolidin-3-yl)oxy)-N-(4-phenylthiazol-2-yl)benzamide $^1$H NMR (CDCl$_3$, 400 MHz) δ ppm: 1.95-2.01 (m, 1 H), 2.56 (s, 3 H), 2.59-2.63 (m, 1 H), 2.79 (s, 3 H), 3.35-3.42 (m, 2 H), 5.17 (t, J=7.2 Hz, 1 H), 7.10 (s, 1 H), 7.24-7.44 (m, 5 H), 7.46 (t, J=2 Hz, 1 H); 7.66 (t, J=2 Hz, 1 H), 7.69 (s, 1 H), 7.92 (d, J=7.2 Hz, 2 H), 8.0 (d, J=8.4 Hz, 2 H), 12.81 (s, 1 H); ESI MS m/z (relative intensities): 568.1 (M+H)$^+$ (100%); UPLC Purity: 92.08%, Ret.time: 4.58 min.

EXAMPLE 38

N-(5-Bromothiazol-2-yl)-3-(4-(5-methyl-1,3,4-oxadiazol-2-yl)phenoxy)-5-((1-methyl-2-oxopyrrolidin-3-yl)oxy)benzamide $^1$H NMR (DMSO-d$_6$, 400 MHz) δ ppm: 1.95-1.99 (m, 1 H), 2.56 (s, 3 H), 2.57-2.61 (m, 1 H), 2.78 (s, 3 H), 3.29-3.35 (m, 1 H), 3.38-3.44 (m, 1 H), 5.14 (t, J=7.2 Hz, 1H), 7.10 (t, J=2 Hz, 1 H), 7.22-7.25 (m, 2 H), 7.41 (t, J=2 Hz, 1 H), 7.61 (t, J=2 Hz, 1 H), 7.65 (s, 1 H), 8.01 (d, J=8.8 Hz, 2 H), 12.94 (bs, 1 H); ESI MS m/z (relative intensities): 571.9 (M+H)$^+$ (100%); UPLC Purity: 98.5%, Ret.time: 4.28 min.

EXAMPLE 39

N-(3-hydroxypyridin-2-yl)-3-(4-(5-methyl-1,3,4-oxadiazol-2-yl)phenoxy)-5-((1-methyl-2-oxopyrrolidin-3-yl)oxy)benzamide $^1$H NMR (DMSO-d$_6$, 400 MHz) δ ppm: 1.96-1.99 (m, 1 H), 2.56 (s, 3 H), 2.60-2.66 (m, 1 H), 2.78 (s, 3 H); 3.35-3.40 (m, 2 H), 5.13 (t, J=7.2 Hz, 1 H), 7.07 (s, 1 H), 7.17-7.24 (m, 5 H), 7.52 (s, 1 H), 7.92 (d, J=7 Hz, 1 H), 7.99 (d, J=6.8 Hz, 2 H), 9.77 (s, 1 H), 10.50 (s, 1 H). ESI MS m/z (relative intensities): 501.9 (M+H)$^+$ (100%); UPLC Purity: 93.5%, Ret.time: 2.86 min.

EXAMPLE 40

3-(4-(5-Methyl-1,3,4-oxadiazol-2-yl)phenoxy)-5-((1-methyl-2-oxopyrrolidin-3-yl)oxy)-N-(4-(p-tolyl)thiazol-2-yl)benzamide $^1$H NMR (DMSO-d$_6$, 400 MHz) δ ppm: 1.90-2.05 (m, 1 H), 2.31 (s, 3 H), 2.56 (s, 3 H), 2.54-2.61 (m, 1 H), 2.89 (s; 3 H), 3.35-3.43 (m, 2 H), 5.17 (t, J=7.2 Hz, 1 H), 7.09 (s, 1 H), 7.13-7.26 (m, 4 H), 7.45 (s, 1 H), 7.59 (s, 1 H), 7.61 (s, 1 H), 7.81 (d, J=7.6 Hz, 2 H), 8.01 (d, J=8.4 Hz, 2 H), 12.77 (s, 1 H); ESI MS m/z (relative intensities): 582.1 (M+H)$^+$ (80%); UPLC Purity: 97.4%, Ret.time: 4.82 min.

EXAMPLE 41

N-(5-Cyanothiazol-2-yl)-3-(4-(5-methyl-1,3,4-oxadiazol-2-yl)phenoxy)-5-((1-methyl-2-oxopyrrolidin-3-yl)oxy)benzamide $^1$H NMR (DMSO-d$_6$, 400 MHz) δ ppm: 1.95-2.02 (m, 1 H), 2.56 (s, 3 H), 2.56-2.64 (m, 1 H), 2.79 (s, 3 H), 3.34-3.41 (m, 2 H), 5.15 (t, J=7.6 Hz, 1 H), 7.14 (t, J=2 Hz, 1H), 7.25 (d, J=8.8 Hz, 2 H), 7.46 (t, J=1.6 Hz, 1 H), 7.64 (t, J=2 Hz, 1 H), 8.00 (d, J=8.8 Hz, 2 H), 8.45 (s, 1 H), 13.46 (bs, 1 H); UPLC Purity: 98.93%, Ret.time: 3.88 min.

EXAMPLE 42

Ethyl-4-(tert-butoxymethyl)-2-(3-(4-(5-methyl-1,3,4-oxadiazol-2-yl)phenoxy)-5-((1-methyl-2-oxopyrrolidin-3-yl)oxy)benzamido)thiazole-5-carboxylate $^1$H NMR (DMSO-d$_6$, 400 MHz) δ ppm: 1.17 (s, 9 H), 1.28 (t, J=7.2 Hz, 3 H), 1.94-2.00 (m, 1 H), 2.56 (s, 3 H), 2.57-2.61 (m, 1 H), 2.79 (s, 3 H), 3.32-3.38 (m, 1 H), 3.39-3.45 (m, 1 H), 4.27 (q, J=7.2 Hz, 2 H), 4.70 (s, 2 H), 5.17 (t, J=6.4 Hz, 1 H), 7.11 (t, J=2 Hz, 1 H), 7.24 (d, J=8.8 Hz, 2 H), 7.45 (t, J=1.6 Hz, 1 H), 7.65 (t, J=2.4 Hz, 1H), 8.01 (d, J=8.8 Hz, 2 H), 13.15 (bs, 1 H); ESI MS m/z (relative intensities): 650.2 (M+H)$^+$, (100%), 672.0 (M+Na)$^+$, (70%); UPLC Purity: 96.23%, Ret.time: 4.756 min.

EXAMPLE 43

4-(tert-Butoxymethyl)-2-(3-(4-(5-methyl-1,3,4-oxadiazol-2-yl)phenoxy)-5-((1-methyl-2-oxopyrrolidin-3-yl)oxy)benzamido)thiazole-5-carboxylic acid $^1$H NMR (DMSO-d$_6$, 400 MHz) δ ppm: 1.17 (s, 9 H), 1.92-1.97 (m, 1 H), 2.48 (s, 3 H), 2.57-2.61 (m, 1 H), 2.79 (s, 3 H), 3.30-3.42 (m, 2 H), 4.70 (s, 2 H), 5.15 (t, J=6.4 Hz, to 1 H), 7.10 (t, J=4.4 Hz, 1 H), 7.25 (d, J=8 Hz, 2 H), 7.45 (t, J=2 Hz, 1 H), 7.65 (t, J=1.6 Hz, 1 H), 7.99 (d, J=8 Hz, 2 H), 13.15 (s, 2 H); ESI MS m/z (relative intensities): 622.1 (M+H)$^+$, (100%), UPLC Purity: 95.36%, Ret.time: 3.746 min.

EXAMPLE 44

4-(tert-Butoxymethyl)-2-(3-(4-(5-methyl-1,3,4-oxadiazol-2-yl)phenoxy)-5-((1-methyl-2-oxopyrrolidin-3-yl)oxy)benzamido)thiazole-5-carboxamide $^1$H NMR (CDCl$_3$, 400 MHz) δ ppm: 1.28 (s, 9 H), 2.16-2.22 (m, 1 H), 2.60 (s, 3 H), 2.59-2.63 (m, 1 H), 2.93 (s, 3 H), 3.38-3.42 (m, 1 H), 3.49-3.53 (m, 1 H), 4.66 (s, 2 H), 4.96 (t, J=6.4 Hz, 1 H), 7.99 (t, J=2 Hz, 1 H), 7.13 (d, J=6.8 Hz, 2 H), 7.24 (s, 1 H), 7.46 (t, J=2.0 Hz, 1 H), 7.13 (d, J=6.8 Hz, 2 H); ESI MS m/z (relative intensities): 621.0 (M+H)$^+$, (100%), 643.2 (M+Na)$^+$, (70%); UPLC Purity: 97.90%, Ret.time: 3.649 min.

EXAMPLE 45

3-(4-(5-Methyl-1,3,4-oxadiazol-2-yl)phenoxy)-5-((1-methyl-2-oxopyrrolidin-3-yl)oxy)-N-(4-methylpyridin-2-yl)benzamide $^1$H NMR (DMSO-d$_6$, 400 MHz) δ ppm: 1.95-1.99 (m, 1 H), 2.33 (s, 3 H), 2.57-2.61 (m, 1 H), 2.56 (s, 3 H), 2.78 (s, 3 H), 3.31-3.37 (m, 1H), 3.39-3.43 (m, 1 H), 5.16 (t, J=7.2 Hz, 1 H), 6.99 (d, J=4.4 Hz, 1 H), 7.04 (t, J=2.4 Hz, 1 H), 7.22 (d, J=8.8 Hz, 2 H), 7.34 (t, J=1.6 Hz, 1 H), 7.54 (t, J=1.6 Hz, 1 H), 7.98 (d, J=8.8 Hz, 2 H), 8.01 (s, 1 H), 8.21 (d, J=4.8 Hz, 1 H), 10.75 (bs, 1 H); ESI MS m/z (relative intensities): 500.1 (M+H)$^+$ (100%); UPLC Purity: 98.1%, Ret.time: 2.97 min.

EXAMPLE 46

N-(5-Chloropyridin-2-yl)-3-(4-(5-methyl-1,3,4-oxadiazol-2-yl)phenoxy)-5-((1-methyl-2-oxo pyrrolidin-3-yl)oxy)benzamide $^1$H NMR (DMSO-d$_6$, 400 MHz) δ ppm: 1.93-1.99 (m, 1 H), 2.56 (s, 3 H), 2.57-2.61 (m, 1 H), 2.78 (s, 3 H), 3.33-3.43 (m, 2 H), 5.16 (t, J=7.6 Hz, 1 H), 7.05 (t, J=2.4 Hz, 1H), 7.20 (d, J=8.8 Hz, 2 H), 7.34 (t, J=1.2 Hz, 1 H), 7.54 (d, J=1.6 Hz, 1 H), 7.94 (d, J=2.8, 1H), 7.96-8.00 (m, 2 H), 8.17 (d, J=8.8 Hz, 1 H), 8.42 (d, J=2.8 Hz, 1 H), 11.04 (s; 1 H); ESI MS m/z (relative intensities): 520 (M)$^+$ (100%), 521 (M+H)$^+$ (30%); UPLC Purity: 99.2%, Ret.time: 4.10 min.

EXAMPLE 47

3-(4-(5-Methyl-1,3,4-oxadiazol-2-yl)phenoxy)-5-((1-methyl-2-oxopyrrolidin-3-yl)oxy)-N-(5-methylpyridin-2-yl)benzamide $^1$H NMR (DMSO-d$_6$, 400 MHz) δ ppm: 1.93-1.99 (m, 1 H), 2.31 (s, 3 H), 2.57-2.61 (m, 1 H), 2.56 (s, 3 H), 2.77 (s, 3 H), 3.30-3.37 (m, 1 H), 3.39-3.42 (m, 1 H), 5.16 (t, J=7.2 Hz, 1 H), 7.03 (t, J=2.4 Hz, 1 H), 7.22 (d, J=8.8 Hz, 2 H), 7.34 (t, J=1.6 Hz, 1 H), 7.55 (t, J=1.6 Hz, 1 H), 7.64 (dd, J=2.4, 8.8 Hz, 1 H), 7.97 (d, J=8.8 Hz, 2 H), 8.01-8.04 (m, 1 H), 8.20 (d, J=4.8 Hz, 1 H), 10.75 (s, 1 H); ESI MS m/z (relative intensities): 499.9 (M+H)$^+$ (100%); UPLC Purity: 94.01%, Ret.time: 3.11 min.

EXAMPLE 48

Methyl 6-(3-(4-(5-methyl-1,3,4-oxadiazol-2-yl)phenoxy)-5-((1-methyl-2-oxopyrrolidin-3-yl)oxy)benzamido)nicotinate $^1$H NMR (DMSO-d$_6$, 400 MHz) δ ppm: 1.91-2.01 (m, 1 H), 2.56 (s, 3 H), 2.57-2.60 (m, 1 H), 2.78 (s, 3 H), 3.33-3.37 (m, 1 H), 3.39-3.42 (m, 1 H), 3.86 (s, 3 H), 5.17 (t, J=7.2 Hz, 1 H), 7.06 (t, J=2 Hz, 1 H), 7.23 (d, J=8.8 Hz, 2 H), 7.36 (t, J=1.6 Hz, 1 H), 7.56 (t, J=1.6 Hz, 1 H), 7.98 (d, J=8.8 Hz, 2 H), 8.28-8.35 (m, 2 H), 8.89 (t, J=0.8 Hz, 1 H), 11.27 (s, 1 H); ESI MS m/z (relative intensities): 543.9 (M+H)$^+$ (100%); UPLC Purity: 98.9%, Ret.time: 3.83 min.

EXAMPLE 49

N-(4-(Hydroxymethyl)thiazol-2-yl)-3-(4-(5-methyl-1,3,4-oxadiazol-2-yl)phenoxy)-5-((1-methyl-2-oxopyrrolidin-3-yl)oxy)benzamide $^1$H NMR (DMSO-d$_6$, 400 MHz) δ ppm: 1.99-2.10 (m, 1 H), 2.56 (s, 3 H), 2.60-2.70 (m, 1 H), 2.79 (s, 3 H), 3.34-3.41 (m, 2 H), 4.48 (d, J=5.6 Hz, 2 H), 5.14 (t, J=7.6 Hz, 1H), 5.22 (t, J=5.6 Hz, 1 H), 6.98 (s, 1 H), 7.07 (t, J=2.4 Hz, 1 H), 7.24 (d, J=7.8 Hz, 2 H), 7.41 (t, J=1.6 Hz, 1 H), 7.61 (d, J=1.6 Hz, 1 H), 8.00 (d, J=7.8 Hz, 2 H), 12.36 (bs, 1 H); ESI MS m/z (relative intensities): 521.8 (M+H)$^+$ (100%); UPLC Purity: 97.2%, Ret.time: 3.18 min.

EXAMPLE 50

2-(3-(4-(5-Methyl-1,3,4-oxadiazol-2-yl)phenoxy)-5-((1-methyl-2-oxopyrrolidin-3-yl)oxy)benzamido)thiazole-4-carboxamide $^1$H NMR (DMSO-d$_6$, 400 MHz) δ ppm: 1.96-1.98 (m, 1 H), 2.48 (s, 3 H), 2.52 (s, 3 H), 2.53-2.56 (m, 1 H), 2.78 (s, 3 H), 3.39-3.44 (m, 1 H), 3.47-3.51 (m, 1 H), 5.14 (t, J=1.6 Hz, 1 H), 7.07 (t, J=2 Hz, 1 H), 7.23 (d, J=8.4 Hz, 2 H), 7.40 (t, J=1.6 Hz, 1 H), 7.59 (t, J=2 Hz, 1 H), 7.99 (d, J=8.4 Hz, 2 H), 12.45 (bs, 1 H); ESI MS m/z (relative intensities): 535.1 (M+H)$^+$ (100%), 556.9 (M+Na)$^+$ (25%); UPLC Purity: 95.08 Ret.time: 3.19 min

EXAMPLE 51

N-(4-Formylthiazol-2-yl)-3-(4-(5-methyl-1,3,4-oxadiazol-2-yl)phenoxy)-5-((1-methyl-2-oxopyrrolidin-3-yl)oxy)benzamide $^1$H NMR (DMSO-d$_6$, 400 MHz) δ ppm: 1.91-2.00 (m, 1 H), 2.45-2.55 (m, 1 H), 2.56 (s, 3 H), 2.79 (s, 3 H), 3.25-3.50 (m, 2 H), 5.15 (t, J=7.2 Hz, 1 H), 7.11 (d, J=2.4 Hz, 1H), 7.25 (d, J=8.8 Hz, 2 H), 7.44 (d, J=1.6 Hz, 1 H), 7.65 (s, 1 H), 8.01 (d, J=8.8 Hz, 2 H), 8.38 (s, 1 H), 9.82 (s, 1 H), 13.05 (s, 1 H); ESI MS m/z (relative intensities): 520.0 (M+H)$^+$ (100%); UPLC Purity: 95.57%, Ret.time: 3.51 min.

EXAMPLE 52

Ethyl 2-(3-((1-cyclopropyl-2-oxopyrrolidin-3-yl)oxy)-5-(4-(5-methyl-1,3,4-oxadiazol-2-yl)phenoxy)benzamido)thiazole-5-carboxylate $^1$H NMR (DMSO-d$_6$, 400 MHz) δ ppm: 0.65-0.73 (m, 4 H), 0.8-0.85 (m, 1 H), 1.28 (t, J=7.2 Hz, 3 H), 1.9-1.95 (m, 1 H), 2.56 (s, 3 H), 2.71-2.80 (m, 1 H), 3.22-3.33 (m, 2 H), 4.28 (q, J=7.2 Hz, 2 H), 5.15 (t, J=7.2 Hz, 1 H), 7.11 (t, J=2 Hz, 1 H), 7.24 (d, J=7.2 Hz, 2 H), 7.43 (t, J=2 Hz, 1 H), 7.62 (t, J=1.6 Hz, 1 H), 8.01 (d, J=7.2 Hz, 2 H), 8.21 (s, 1 H), 13.11 (s, 1 H); ESI MS m/z (relative intensities): 589.9 (M+H)$^+$ (20%), 611.8 (M+Na)$^+$ (100%); UPLC Purity: 91.8%, Ret.time: 4.32 min.

EXAMPLE 53

Ethyl 2-(3-((1-isopropyl-2-oxopyrrolidin-3-yl)oxy)-5-(4-(5-methyl-1,3,4-oxadiazol-2-yl)phenoxy)benzamido)thiazole-4-carboxylate $^1$H NMR (DMSO-d$_6$, 400 MHz) δ ppm: 1.17 (d, J=7.2 Hz, 3 H), 1.21 (d, J=6.8 Hz, 3H), 1.3 (t, J=7.2 Hz, 3 H), 1.91-2.00

(m, 1 H), 2.56 (s, 3 H), 2.60-2.72 (m, 1 H), 3.25-3.3.36 (m, 1 H), 3.38-3.42 (m, 1 H), 4.13-4.16 (m, 1 H), 4.27 (q, J=7.2 Hz, 2 H), 5.17 (t, J=8 Hz, 1 H), 7.09 (t, J=2 Hz, 1 H), 7.25 (d, J=6.8 Hz, 2 H), 7.44 (t, J=1.6 Hz, 1 H), 7.66 (s, 1 H), 8.01 (d, J=6.8 Hz, 2 H), 8.12 (s, 1 H), 13.04 (bs, 1 H); ESI MS m/z (relative intensities): 592 (M+H)$^+$ (100%); UPLC Purity: 98.9%, Ret.time: 4.36 min.

EXAMPLE 54

Ethyl 2-(3((1-isopropyl-2-oxopyrrolidin-3-yl)oxy)-5-(4-(5-methyl-1,3,4-oxadiazol-2-yl)phenoxy)benzamido)thiazole-5-carboxylate $^1$H NMR (DMSO-d$_6$, 400 MHz) δ ppm: 1.17 (d, J=7.2 Hz, 3 H), 1.20 (d, J=6.8 Hz, 3 H), 1.31 (t, J=7.2 Hz, 3 H), 1.91-2.00 (m, 1 H), 2.56 (s, 3 H), 2.61-2.70 (m, 1 H), 3.21-3.35 (m, 1 H), 3.39-3.50 (m, 1 H), 4.11-4.16 (m, 1 H), 4.28 (q, J=7.2 Hz, 2 H), 5.17 (t, J=6.8 Hz, 1 H), 7.12 (t, J=2 Hz, 1 H), 7.24 (d, J=8.8 Hz, 2 H), 7.43 (t, J=1.6 Hz, 1 H), 7.63 (s, 1 H), 7.99 (d, J=8.8 Hz, 2 H), 8.21 (s, 1 H), 13.11 (s, 1 H); ESI MS m/z (relative intensities): 592.1 (M+H)$^+$ (100%); UPLC Purity: 90.16%, Ret.time: 4.46 min.

EXAMPLE 55

Ethyl 2-(3-(4-(5-cyclopentyl-1,3,4-oxadiazol-2-yl)phenoxy)-5-((1-methyl-2-oxopyrrolidin-3-yl)oxy)benzamido)thiazole-4-carboxylate $^1$H NMR (DMSO-d$_6$, 400 MHz) δ ppm: 1.28 (t, J=7.2 Hz, 3 H), 1.66-1.73 (m, 4 H), 1.91-2.00 (m, 2 H), 1.95-2.05 (m, 1 H), 2.05-2.1 (m, 2 H), 2.55-2.65 (m, 1 H), 2.79 (s, 3 H), 3.31-3.40 (m, 1 H), 3.41-3.43 (m, 2 H), 4.28 (q, J=7.2 Hz, 2 H), 5.15 (t, J=7.2 Hz, 1 H), 7.09 (t, J=1.6 Hz, 1 H), 7.25 (d, J=8.8 Hz, 2 H), 7.43 (s, 1 H), 7.65 (s, 1 H), 8.01 (d, J=8.8 Hz, 2 H), 8.11 (s, 1 H) 13.04 (bs, 1 H); ESI MS m/z relative intensities: 617.8 (M+H)$^+$ (100%); UPLC Purity: 98.6%, Ret.time: 4.84 min.

EXAMPLE 56

Ethyl 5-chloro-2-(3-(4-(5-cyclopentyl-1,3,4-oxadiazol-2-yl)phenoxy)-5-((1-methyl-2-oxo pyrrolidin-3-yl)oxy)benzamido)thiazole-4-carboxylate $^1$H NMR (DMSO-d$_6$, 400 MHz) δ ppm: 1.28 (t, J=7.2 Hz, 3 H), 1.66-1.73 (m, 4 H), 1.85-1.89 (m, 2 H), 1.91-2.01 (m, 1 H), 2.05-2.11 (m, 2 H), 2.61-2.71 (m, 1 H), 2.78 (s, 3 H), 3.30-3.40 (m, 1 H), 3.40-3.43 (m, 2 H), 4.29 (q, J=7.2 Hz, 2 H), 5.14 (t, J=7.2 Hz, 1 H), 7.10 (t, J=2.4 Hz, 1 H), 7.25 (d, J=6.8 Hz, 2 H), 7.42 (t, J=2 Hz, 1 H), 7.64 (s, 1H), 8.01 (d, J=6.8 Hz, 2 H), 13.27 (bs, 1 H); ESI MS m/z (relative intensities): 652.1 (M+H)$^+$ (100%); UPLC Purity: 98.8%, Ret.time: 5.39 min.

EXAMPLE 57

Ethyl 2-(3-(4-(5-isobutyl-1,3,4-oxadiazol-2-yl)phenoxy)-5-((1-methyl-2-oxopyrrolidin-3-yl)oxy)benzamido)thiazole-4-carboxylate $^1$H NMR (DMSO-d$_6$, 400 MHz) δ ppm: 0.81 (d, J=7.2 Hz, 3 H), 0.84 (d, J=6.4 Hz, 3 H), 1.28 (t, J=7.2 Hz, 3 H), 1.91-2.00 (m, 1 H), 2.11-2.21 (m, 1 H), 2.60-2.70 (m, 1 H), 2.79 (s, 3 H), 2.81 (d, J=7.2 Hz, 2 H), 3.40-3.50 (m, 1 H), 4.27 (q, J=7.2 Hz, 2H), 5.15 (t, J=7.2 Hz, 1 H), 7.09 (t, J=2.0 Hz, 1 H), 7.25 (d, J=6.8 Hz, 2 H), 7.43 (d, J=1.6 Hz, 1 H), 7.65 (s, 1 H), 8.01 (d, J=6.8 Hz, 2 H), 8.11 (s, 1 H) 13.04 (bs, 1 H); ESI MS m/z (relative intensities): 606.1 (M+H)$^+$ (50%); UPLC Purity: 95.6%, Ret.time: 4.75 min.

EXAMPLE 58

Ethyl 5-chloro-2-(3-(4-(5-isobutyl-1,3,4-oxadiazol-2-yl)phenoxy)-5-((1-methyl-2-oxopyrrolidin-3-yl)oxy)benzamido)thiazole-4-carboxylate $^1$H NMR (DMSO-d$_6$, 400 MHz) δ ppm: 0.95 (d, J=7.2 Hz, 3 H), 0.98 (d, J=7.2 Hz, 3 H), 1.26 (t, J=7.2 Hz, 3 H), 1.91-2.0 (m, 1 H), 2.10-2.21 (m, 1 H), 2.61-2.70 (m, 1 H), 2.78 (s, 3 H), 2.80 (d, J=6.8 Hz, 2 H), 3.41-3.40 (m, 2 H), 4.29 (q, J=7.2 Hz, 2H), 5.14 (t, J=7.2 Hz, 1 H), 7.10 (t, J=2.0 Hz, 1 H), 7.25 (d, J=7.2 Hz, 2 H), 7.43 (d, J=1.6 Hz, 1 H), 7.63 (t, J=2 Hz, 1 H), 8.01 (d, J=7.2 Hz, 2 H), 13.27 (bs, 1 H); ESI MS m/z (relative intensities): 640.1 (M+H)$^+$ (100%); UPLC Purity: 98.8%, Ret.time: 5.29 min.

EXAMPLE 59

3((1-Ethyl-2-oxopyrrolidin-3-yl)oxy)-5-(4-(5-methyl-1,3,4-oxadiazol-2-yl)phenoxy)-N-(4-methylthiazol-2-yl)benzamide $^1$H NMR (DMSO-d$_6$, 400 MHz) δ ppm: 1.05 (t, J=7.2 Hz, 3 H), 1.87-2.01 (m, 1 H), 2.28 (s, 3 H), 2.56 (s, 3 H), 2.55-2.68 (m, 1 H), 3.23-3.28 (m, 2 H), 3.24-3.50 (m, 1 H), 3.40-3.42 (m, 1 H), 5.15 (t, J=7.6 Hz, 1 H), 6.81 (s, 1H), 7.07 (t, J=1.6 Hz, 1 H), 7.24 (d, J=8.4 Hz, 2 H), 7.40 (t, J=1.6 Hz, 1 H), 7.61 (t, J=2.0 Hz, 1 H), 7.99 (d, J=8.4 Hz, 2 H), 12.59 (bs, 1 H); ESI MS m/z (relative intensities): 520.1 (M+H)$^+$ (100%); UPLC Purity: 94.66%, Ret.time: 3.943 min.

EXAMPLE 60

3((1-Ethyl-2-oxopyrrolidin-3-yl)oxy)-5-(4-(5-methyl-1,3,4-oxadiazol-2-yl)phenoxy)-N-(5-methylthiazol-2-yl)benzamide $^1$H NMR (DMSO-d$_6$, 400 MHz) δ ppm: 1.05 (t, J=7.8 Hz, 3 H), 1.93-1.98 (m, 1 H), 2.35 (s, 3 H), 2.56 (s, 3 H), 2.60-2.62 (m, 1 H), 3.23-3.28 (m, 2 H), 3.30-3.36 (m, 1 H), 3.39-3.44 (m, 1 H), 5.16 (t, J=7.6 Hz, 1 H), 7.07 (s, 1 H), 7.20 (s, 1 H), 7.23 (d, J=8.4 Hz, 2 H), 7.40 (s, 1 H), 7.60 (s, 1 H), 7.99 (d, J=8.4 Hz, 2 H), 12.40 (bs, 1 H); ESI MS m/z (relative intensities): 519.9 (M+H)$^+$ (100%); 533.9 (M+Na)$^+$ (20%); UPLC Purity: 95.26%, Ret.time: 3.947 min.

EXAMPLE 61

N,N-Dimethyl-2-(3-(4-(5-methyl-1,3,4-oxadiazol-2-yl)phenoxy)-5-((1-methyl-2-oxopyrrolidin-3-yl)oxy)benzamido)thiazole-5-carboxamide $^1$H NMR (DMSO-d$_6$, 400 MHz) δ ppm: 2.15-2.23 (m, 1 H), 2.46-2.56 (m, 1 H), 2.62 (s, 3 H), 2.93 (s, 3 H), 3.19 (bs, 6 H), 3.37-3.43 (m, 1 H), 3.49-3.54 (m, 1 H), 4.94 (t, J=7.6 Hz, 1 H), 6.98 (t, J=2 Hz, 1 H), 7.11 (d, J=6.8 Hz, 2 H), 7.24 (s, 1 H), 7.46 (t, J=1.6 Hz, 1 H), 7.69 (s, 1 H), 8.01 (d, J=6.8 Hz, 2 H), 12.85 (bs, 1 H); ESI MS m/z (relative intensities): 563.1 (M+H)$^+$ (100%), 584.8 (M+Na)+ (10%); UPLC Purity: 98.37%, Ret.time: 3.29 min

EXAMPLE 62

N,N-Dimethyl-2-(3-(4-(5-methyl-1,3,4-oxadiazol-2-yl)phenoxy)-5-((1-methyl-2-oxopyrro-lidin-3-yl)oxy)benzamido)thiazole-4-carboxamide $^1$H NMR (DMSO-d$_6$, 400 MHz) δ ppm: 1.96-2.00 (m, 1 H), 2.59-2.62 (m, 4 H), 2.79 (s, 3 H), 2.96 (s, 3 H), 3.09 (s, 3 H), 3.34-3.41 (m, 2 H), 5.15 (t, J=7.2 Hz, 1 H), 7.10 (t, J=2 Hz, 1 H), 7.24 (d, J=8.8 Hz, 2 H), 7.41-7.44 (m, 1 H), 7.57-7.59 (m, 1 H), 7.63 (t, J=1.6 Hz, 1 H), 8.00 (d, J=8.8 Hz, 2 H), 12.79 (s, 1 H); ESI MS m/z (relative intensities): 563.0 (M+H)$^+$; (100%), 584.9 (M+Na)$^+$ (20%); UPLC Purity: 93.93%, Ret.time: 3.32 min.

EXAMPLE 63

2-(3-(4-(5-Methyl-1,3,4-oxadiazol-2-yl)phenoxy)-5-((1-methyl-2-oxopyrrolidin-3-yl)oxy)benzamido)thiazole-5-carboxamide $^1$H NMR (DMSO-d$_6$, 400 MHz) δ ppm: 1.98-2.10 (m, 1 H), 2.56 (s, 3 H), 2.56-2.60 (m, 1 H), 2.78 (s, 3 H), 3.29-3.44 (m, 2 H), 5.15 (t, J=1.6 Hz, 1 H), 7.10 (t, J=2 Hz, 1 H), 7.23 (d, J=7.2 Hz, 2 H), 7.42-7.43 (m, 2 H), 7.61 (t, J=2 Hz, 1 H), 7.98 (s, 1 H), 8.01 (d, J=7.2 Hz, 2 H), 8.29 (s, 1 H) 12.85 (bs, 1 H); ESI MS m/z (relative intensities): 534.9 (M+H)$^+$ (100%), 546.8 (M+Na)$^+$ (25%); UPLC Purity: 96.98%, Ret.time: 3.01 min.

EXAMPLE 64

2-(3((1-Methoxypropan-2-yl)oxy)-5-(4-(5-methyl-1,3,4-oxadiazol-2-yl)phenoxy)benzamido)thiazole-5-carboxamide $^1$H NMR (CDCl$_3$, 400 MHz) δ ppm: 1.24 (d, J=6 Hz, 3 H), 2.56 (s, 3 H), 3.30 (s, 3H), 3.45-3.50 (m, 2 H), 4.75-4.85 (m, 1 H), 6.97 (t, J=2 Hz, 1 H), 7.22 (d, J=6.8 Hz, 2 H), 7.35 (t, J=1.6 Hz, 1 H), 7.45 (bs, 1 H), 7.55 (s, 1 H), 7.97 (bs, 1 H), 8.00 (d, J=6.8 Hz, 2 H), 8.11 (s, 1 H), 12.8 (bs, 1 H); ESI MS m/z (relative intensities): 509.9 (M+H)$^+$ (100%), 531.6 (M+Na)$^+$ (20%); UPLC Purity: 97.24%, Ret.time: 3.569 min.

EXAMPLE 65

3-(4-(5-Cyclopentyl-1,3,4-oxadiazol-2-yl)phenoxy)-5-((1-methyl-2-oxopyrrolidin-3-yl)oxy)-N-(thiazol-2-yl)benzamide $^1$H NMR (CDCl$_3$, 400 MHz) δ ppm: 1.68-1.73 (m, 4 H), 1.80-1.94 (m, 2 H), 1.95-2.20 (m, 3 H), 2.55-2.65 (m, 1 H), 2.79 (s, 3 H), 3.23-3.41 (m, 3 H), 5.14 (t, J=7.6 Hz, 1H), 7.07 (t, J=2 Hz, 1 H), 7.23-7.26 (m, 3 H), 7.40 (t, J=2 Hz, 1 H), 7.54 (d, J=3.6 Hz, 1 H), 7.62 (t, J=2 Hz, 1 H), 8.01 (d, J=8.8 Hz, 2 H), 12.65 (bs, 1 H); ESI MS m/z (relative intensities): 545.9 (M+H)$^+$ (100%); UPLC Purity: 98.43%, Ret.time: 4.43 min.

EXAMPLE 66

Ethyl 5-chloro-2-(3((1-cyclopropyl-2-oxopyrrolidin-3-yl)oxy)-5-(4-(5-methyl-1,3,4-oxa-diazol-2-yl)phenoxy)benzamido)thiazole-4-carboxylate $^1$H NMR (DMSO-d$_6$, 400 MHz) δ ppm: 0.72-0.84 (m, 4 H), 1.28 (t, J=7.2 Hz, 3 H), 1.89-1.95 (m, 1 H), 2.54-2.56 (m, 4 H), 2.71-2.73 (m, 1 H), 3.23-3.26 (m, 2 H), 4.29 (q, J=7.2 Hz, 2 H), 5.14 (t, J=7.6 Hz, 1 H), 7.10 (s, 1H), 7.24 (d, J=8.8 Hz, 2 H), 7.44 (s, 1 H), 7.63 (s, 1 H), 8.00 (d, J=8.8.1-1 z, 2 H), 13.27 (bs, 1 H); ESI MS m/z (relative intensities): 623.9 (M)$^+$, (100%); UPLC Purity: 95.02%, Ret.time: 4.77 min.

EXAMPLE 67

3-(4-(5-Cyclopentyl-1,3,4-oxadiazol-2-yl)phenoxy)-5-((1-methyl-2-oxopyrrolidin-3-yl)oxy)-N-(5-methylthiazol-2-yl)benzamide $^1$H NMR (DMSO-d$_6$, 400 MHz) δ ppm: 1.67-1.73 (m, 4 H), 1.70-1.89 (m, 2 H), 1.90-2.10 (m, 3 H), 2.35 (s, 3 H), 2.50-2.65 (m, 1 H), 2.78 (s, 3 H), 3.39-3.41 (m, 3 H), 5.13 (t, J=7.6 Hz, 1 H), 7.06 (t, J=2 Hz, 1 H), 7.20 (s, 1 H), 7.24 (d, J=8.8 Hz, 2 H), 7.38 (t, J=1.6 Hz, 1 H), 7.59 (s, 1 H), 8.00 (d, J=8.4 Hz, 2 H), 12.5 (bs, 1 H); ESI MS m/z (relative intensities): 559.9 (M+H)$^+$ (100%); UPPLC Purity: 98.04%, Ret.time: 4.64 min.

EXAMPLE 68

(S)-3-(4-(5-Methyl-1,3,4-oxadiazol-2-yl)phenoxy)-5-((1-methyl-2-oxopyrrolidin-3-yl)oxy)-N-(thiazol-2-yl)benzamide To a stirring solution of S-(+3-[4-(5-Methyl-1,3,4-oxadiazol-2-yl)phenoxy]-5-[(1-methyl-2-oxo-pyrrolidin-3-yl)oxy]benzoic acid (3.5 g) (Intermediate 13) in dry DCM in single necked round bottomed flask fitted with stop cock with N$_{2(g)}$ balloon, 4-(dimethylamino)pyridine (2.24 g) followed by N-(3-Dimethylaminopropyl)-N'-ethylcarbodiimide hydrochloride (EDCI. HCl) (3.3 g) were added at room temperature. After stirring at the same temperature for 15 min, 2-aminothiazole (0.94 g) was added and stirring was continued for 16 h. Progress of reaction was monitored by TLC. After completion, reaction mixture was diluted with DCM (200 mL), washed with dil HCl (20 mL, 0.05 N), saturated sodium bicarbonate solution, water and brine, dried over anhydrous sodium sulphate, filtered and concentrated under vacuum to get crude brown solid (3.5 g). The crude brown solid was purified by solvent trituration.

$^1$H NMR (CDCl$_3$, 400 MHz) δ ppm: 2.13-2.22 (m, 1 H), 2.62 (s, 3 H), 2.56-2.64 (m, 1H), 2.93 (s, 3 H), 3.39-3.43 (m, 1 H), 3.48-3.53 (m, 1 H), 4.92 (t, J=7.2 Hz, 1 H), 7.01 (s, 1 H), 7.04 (t, J=2 Hz, 1 H), 7.21 (d, J=8.8 Hz, 2 H), 7.26 (s, 1 H), 7.36 (s, 1 H), 7.44 (s, 1 H), 7.99 (d, J=8.8 Hz, 2 H); ESI MS m/z (relative intensities): 492.1 (M+H)$^+$ (100%), 513.8 (M+Na)$^+$ (10%); UPLC Purity: 98.13%, Ret. time: 3.577 min. Chiral Purity by HPLC: 97.31%, Ret. time: 22.93 min. % ee: 94.62%

Intermediate 13

S-(−)-3-[4-(5-Methyl-1,3,4-oxadiazol-2-yl)phenoxy]-5-[(1-methyl-2-oxo-pyrro-lidin-3-yl)oxy]benzoic acid Sodium hydroxide (pallets, 1.5 g) was added to a stirring mixture of (S)-(−)-Methyl 3-[4-(5-methyl-1,3,4-oxadiazol-2-yl)phenoxy]-5-[(1-methyl-2-oxo-pyrrolidin-3-yl)oxy]benzoate (5.3 g) (Intermediate 14) in MeOH:H$_2$O (1:1) at room temperature. The reaction was monitored by TLC. After completion, methanol was evaporated from the reaction mixture and water was added. The aqueous layer was washed with EtOAc, acidified with dil. HCl (0.05 N) to obtain solid.

The solid obtained was filtered, washed with water, dried under suction or vacuum to get pure white solid (3.5 g).

$^1$H NMR (CDCl$_3$, 400 MHz) δ ppm: 2.17-2.22 (m, 1 H), 2.62 (s, 3 H), 2.58-2.66 (m, 1H), 2.93 (s, 3 H), 3.39-3.43 (m, 1 H), 3.48-3.53 (m, 1 H), 4.99 (t, J=7.2 Hz, 1 H), 6.89 (t, J=2.4 Hz, 1 H), 7.07 (d, J=8.8 Hz, 2 H), 7.28 (s, 1 H), 7.53 (s, 1 H), 7.95 (d, J=8.8 Hz, 2 H); ESI MS m/z (relative intensities): 410 (M+H)$^+$ (100%); UPLC Purity: 97.85%, Ret. time: 3.136 min. Chiral Purity by HPLC: 99.59%, Ret. Time: 57.46 min. % ee: 99.18%

Intermediate 14

(S)-(−)-Methyl 3-[4-(5-methyl-1,3,4-oxadiazol-2-yl) phenoxy]-5-[(1-methyl-2-oxo-pyrrolidin-3-yl)oxy] benzoate Sodium hydride suspension (0.71 g, 50%) was added to a stirring solution of (S)-(−)-methyl 3-(4-(5-methyl-1,3,4-oxadiazol-2-yl)phenoxy)-5-((2-oxopyrrolidin-3-yl)oxy)benzoate (5.5 g) (Intermediate 15) in dry DMF taken in a round bottomed flask fitted with anhydrous CaCl$_2$ guard tube at room temperature. The reaction mixture was stirred at the same temperature for 15 min. Methyl iodide (0.91 mL) was added and stirred till the reaction completion. The reaction mixture was quenched with ice-water, extracted with DCM. All organic layers were combined, washed with water, brine, dried over sodium sulphate, filtered and concentrated in vaccuo to get the thick liquid product. The liquid was triturated with EtOAc:hexane to get the white solid product (5.3 g).

$^1$H NMR (CDCl$_3$, 400 MHz) δ ppm: 2.14-2.21 (m, 1 H), 2.58-2.63 (m, 1 H), 2.64 (s, 3 H), 2.93 (s, 3 H), 3.39-3.43 (m, 1 H), 3.48-3.53 (m, 1 H), 3.89 (s, 3 H), 4.99 (t, J=7.2 Hz, 1 H), 6.99 (t, J=2 Hz, 1 H), 7.07 (d, J=8.8 Hz, 2 H), 7.35 (s, 1 H), 7.53 (s, 1 H), 7.99 (d, J=8.8 Hz, 2 H); ESI MS m/z (relative intensities): 424.1 (M+H)$^+$ (100%); UPLC Purity: 96.11%, Ret. time: 3.68 min. Chiral Purity by HPLC: 92.05%, Ret. Time: 39.33 min.

Intermediate 15

(S)-(−)-Methyl 3-(4-(5-methyl-1,3,4-oxadiazol-2-yl) phenoxy)-5-((2-oxo pyrrolidin-3-yl)oxy)benzoate To a stirring mixture of Methyl 3-hydroxy-5-[4-(5-methyl-1,3,4-oxadiazol-2-yl)phenoxy]benzoate (7 g) (Intermediate 7) and (R)-(+)-3-hydroxy-2-pyrrolidinone (Intermediate 16) (2.4 g) in dry THF (200 mL) taken in round bottomed flask fitted with anhydrous CaCl$_2$ guard tube, triphenyl phosphine (11.3 g) was added. Diisopropyl azodicarboxylate (DIAD) (6.2 mL) in dry THF (10 mL) was added drop wise to the above reaction mixture. The reaction was stirred at room temperature. Reaction was monitored by TLC for completion. After completion, reaction mixture was concentrated under vacuum to remove the solvents. Diluted with DCM and coated over silica gel and chromatographed to furnish the product as white solid (6 g).

$^1$H NMR (CDCl$_3$, 400 MHz) δ ppm: 2.26-2.33 (m, 1 H), 2.62 (s, 3 H), 2.64-2.71 (m, 1H), 3.40-3.47 (m, 1 H), 3.51-3.55 (m, 1 H), 3.89 (s, 3 H), 4.89 (t, J=7.6 Hz, 1 H), 6.07 (bs, 1 H), 6.99 (t, J=2.4 Hz, 1 H), 7.11 (d, J=8.8 Hz, 2 H), 7.36 (s, 1 H), 7.51 (s, 1 H), 8.03 (d, J=8.8 Hz, 2 H); ESI MS m/z (relative intensities): 410.1 (M+H)$^+$ (100%); UPLC Purity: 98.35%, Ret. time: 3.47 min. Chiral Purity by HPLC: 95.31%, Ret. Time: 47.97 min. ee: 90.62%.

Intermediate 16

(R)-(+)-3-Hydroxy-2-pyrrolidinone

To a stirring mixture of 4-Nitrobenzoic acid (21.5 g) and (S)-(−)-3-hydroxy-2-pyrrolidinone (11.8 g) (Intermediate 17) in dry THF (360 mL) taken in a round bottomed flask fitted with anhydrous CaCl$_2$ guard tube, triphenyl phosphine (61.2 g) was added. To this reaction mixture, diisopropyl diazodicarboxylate (DIAD) (34 mL) was added drop wise in three portions at room temperature. The reaction was stirred at room temperature. The progress of the reaction was monitored by TLC (developing agents: UV, I$_2$, as well as aqueous acidic KMnO$_4$). After completion, reaction mixture was concentrated under vacuum to obtain residue. Methanol (360 mL) was added to the residue followed by potassium carbonate (10 g) at room temperature. The reaction was stirred at room temperature. The progress of the reaction was monitored by TLC (developing agents: UV, I$_2$, as well as aqueous acidic KMnO$_4$). After completion, reaction mixture was diluted with CHCl$_3$ and filtered through celite. Celite bed was successively washed with 1% MeOH:CHCl$_3$. The filtrates were combined and concentrated to dryness to remove solvents. The residues were partitioned between EtOAc: dil. HCl (200 mL, 9:1) and stirred for 15 min. Layers were separated, aq. layer was washed with EtOAc thrice until all organic impurities were washed out. The aq. Layer was concentrated to dryness to remove the water and solid residues were obtained. The residues obtained were washed with 1-2% MeOH: CHCl$_3$ (3×100 mL), dried over sodium sulfate, filtered trough cotton, concentrated to get brown thick liquid product.

$^1$H NMR (CDCl$_3$, 400 MHz) δ ppm: 2.03-2.13 (m, 1 H), 2.46-2.54 (m, 1 H), 3.28-3.35 (m, 1 H), 3.38-3.48 (m, 1 H), 4.50 (t, J=8.4 Hz, 1 H), 4.55 (bs, 1 H), 7.02 (bs, 1 H); [α]$_D^{25}$: +68, c=1, CHCl$_3$ Intermediate 17

(S)-(−)-3-hydroxy-2-pyrrolidinone

Conc. H$_2$SO$_4$ (14.8 g, 8 mL) was added drop wise over 5 min to the stirring solution of (S)-(−)-4-Amino-2-hydroxybutyric acid (15 g) [CAS No. 40371-51-5] in MeOH (95 mL) under dry conditions using anhydrous CaCl$_2$ guard tube. After refluxing for 4 h, the reaction mixture was allowed to cool to room temperature and diluted with water (15 mL). Potassium carbonate (24 g) was added in portions to the reaction mixture and stirred overnight (20 h). Reaction mixture was diluted with CHCl$_3$, filtered through celite. Celite bed was thoroughly washed with 1% MeOH:CHCl$_3$. The filtrates were combined and evaporated to dryness to obtain thick liquid residue. The residue was subjected to aging using 1-2% MeOH:CHCl$_3$ and then filtered. Organic layers were combined, dried over anhydrous sodium sulphate, filtered and concentrated to obtain the white solid. (11.8 g)

$^1$H NMR (CDCl$_3$, 400 MHz) δ ppm: 2.03-2.13 (m, 1 H), 2.48-2.55 (m, 1 H), 3.30=3.35 (m, 1 H), 3.36-3.50 (m, 1 H), 4.34 (t, J=8.4 Hz, 1 H), 6.51 (bs, 1 H); [α]$_D^{25}$: +98, c=1, CHCl$_3$ Following examples (Example 70-76) were prepared by using similar procedure as that of example 1 with suitable modifications as are well within the scope of a skilled person

EXAMPLE 69

(S)-(5-cyanothiazol-2-yl)-3-(4-(5-methyl-1,3,4-oxadiazol-2-yl)phenoxy)-5-((1-methyl-2-oxopyrrolidin-3-yl)oxy)benzamide $^1$H NMR (DMSO-d$_6$, 400 MHz) δ ppm: 1.98-2.02 (m, 1 H), 2.56 (s, 3 H); 2.56-2.64 (m, 1 H), 2.79 (s, 3 H), 3.30-3.44 (m, 2 H), 5.15 (t, J=7.6 Hz, 1 H), 7.14 (t, J=2 Hz, 1H), 7.24 (d, J=8.8 Hz, 2 H), 7.46 (t, J=2 Hz, 1 H), 7.64 (t, J=2 Hz, 1 H), 7.94 (d, J=8.8 Hz, 2 H), 8.45 (s, 1 H), 13.47 (bs, 1 H). UPLC Purity: 99.01%, Ret.time: 3.87 min.

EXAMPLE 70

(S)-3-(4-(5-methyl-1,3,4-oxadiazol-2-yl)phenoxy)-5-((2-oxopyrrolidin-3-yl)oxy)-N-(thiazol-2-yl)benzamide $^1$H NMR (DMSO-d$_6$, 400 MHz) δ ppm: 1.98-2.02 (m, 1 H), 2.56 (s, 3 H), 2.56-2.64 (m, 1 H), 3.45-3.49 (m, 1 H), 3.54-3.58 (m, 1 H), 5.07 (t, J=7.2 Hz, 1 H), 7.08 (t, J=2 Hz, 1 H), 7.25 (d, J=8.8 Hz, 2 H), 7.28 (s 1 H), 7.41 (s, 1 H), 7.53 (s, 1 H), 7.63 (s, 1 H), 8.01 (d, J=8.8 Hz, 2 H), 8.10 (s, 1 H), 12.66 (bs, 1 H), ESI MS m/z (relative intensities): 492.1 (M+H)$^+$ (100%), 513.8 (M+Na)$^+$ (10%); UPLC Purity: 92.12%, Ret.time: 3.357 min

EXAMPLE 71

(S)-Ethyl 2-(3-(4-(5-methyl-1,3,4-oxadiazol-2-yl)phenoxy)-5-((1-methyl-2-oxopyrrolidin-3-yl)oxy)benzamido)thiazole-4-carboxylate $^1$H NMR (DMSO-d$_6$, 400 MHz) δ ppm: 1.28 (t, J=7.2 Hz, 3 H), 1.91-2.00 (m, 1 H), 2.60 (s, 3 H), 2.61-2.79 (m, 1 H), 2.80 (s, 3 H), 3.31-3.50 (m, 2 H), 4.29 (q, J=7.2 Hz, 2 H), 5.15 (t, J=7.6 Hz, 1 H), 7.09 (t, J=2 Hz, 1 H), 7.25 (d, J=8.8 Hz, 2 H), 7.45 (t, J=1.6 Hz, 1 H), 7.65 (t, J=1.6 Hz, 1 H), 8.00 (d, J=8.8 Hz, 2 H), 8.12 (s, 1 H), 13.05 (bs, 1 H); ESI MS m/z (relative intensities): 563.9 (M+H)$^+$ (100%); UPLC Purity: 97.4%, Ret.time: 3.99 min.

EXAMPLE 72

(S)-Ethyl 2-(3-(4-(5-methyl-1,3,4-oxadiazol-2-yl)phenoxy)-5-((1-methyl-2-oxopyrrolidin-3-yl)oxy)benzamido)thiazole-5-carboxylate $^1$H NMR (DMSO-d$_6$, 400 MHz) δ ppm: 1.29 (t, J=7.2 Hz, 3 H), 1.91-2.00 (m, 1 H), 2.58 (s, 3 H), 2.61-2.70 (m, 1 H), 2.78 (s, 3 H), 3.32-3.43 (m, 2 H), 4.28 (q, J=7.2 Hz, 2 H), 5.15 (t, J=7.6 Hz, 1 H), 7.12 (t, J=2 Hz, 1 H), 7.25 (d, J=8.8 Hz, 2 H), 7.44 (t, J=1.6 Hz, 1 H), 7.63 (t, J=1.2 Hz, 1 H), 8.01 (d, J=8.8 Hz, 2 H), 8.21 (s, 1 H), 13.12 (bs, 1 H); ESI MS m/z (relative intensities): 564.1 (M+H)$^+$ (100%); UPLC Purity: 94.7%, Ret.time: 4.09 min.

EXAMPLE 73

(S)-3-(4-(5-methyl-1,3,4-oxadiazol-2-yl)phenoxy)-5-((1-methyl-2-oxopyrrolidin-3-yl)oxy)-N-(4-methylthiazol-2-yl)benzamide $^1$H NMR (DMSO-d$_6$, 400 MHz) δ ppm: 2.10-2.19 (m, 1 H), 2.32 (s, 3 H), 2.52-2.60 (m, 1 H), 2.61 (s, 3 H), 2.92 (s, 3 H), 3.35-3.41 (m, 1 H), 3.46-3.52 (m, 1 H), 4.86 (t, J=7.2 Hz, 1 H), 6.55 (d, J=0.8 Hz, 1 H), 6.99 (t, J=2.4 Hz, 1 H), 7.10 (d, J=8.8 Hz, 2 H), 7.15 (t, J=1.6 Hz, 1 H), 7.40 (t, J=1.6 Hz, 1 H), 8.01 (d, J=8.8 Hz, 2 H), 10.35 (s, 1 H); ESI MS m/z (relative intensities): 506.00 (M+H)$^+$ (100%), 527.80 (M+Na)$^+$ (25%); UPLC Purity: 93.98%, Ret.time: 3.74 min.

EXAMPLE 74

(S)-3-(4-(5-methyl-1,3,4-oxadiazol-2-yl)phenoxy)-5-((1-methyl-2-oxopyrrolidin-3-yl)oxy)-N-(5-methylthiazol-2-yl)benzamide $^1$H NMR (DMSO-d$_6$, 400 MHz) δ ppm: 1.96-1.98 (m, 1 H), 2.48 (s, 3 H), 2.52 (s, 3 H), 2.53-2.56 (m, 1 H), 2.78 (s, 3 H), 3.39-3.51 (m, 1 H), 3.50-3.60 (m, 1 H), 5.14 (t, J=5.6 Hz, 1 H), 7.07 (t, J=2 Hz, 1 H), 7.20-7.22 (m, 1 H), 7.23-7.24 (d, J=8.4 Hz, 2 H), 7.40 (t, J=1.6 Hz, 1 H), 7.59 (t, J=2 Hz, 1 H), 7.99 (d, J=8.4 Hz, 2 H), 12.45 (bs, 1 H); ESI MS m/z (relative intensities): 506.00 (M+H)$^+$ (100%), 527.8 (M+Na)$^+$ (25%); UPLC Purity: 98.56% Ret.time: 3.75 min.

EXAMPLE 75

(S)—N-(4,5-dihydrothiazol-2-yl)-3-(4-(5-methyl-1,3,4-oxadiazol-2-yl)phenoxy)-5-((1-methyl-2-oxopyrrolidin-3-yl)oxy)benzamide $^1$H NMR (DMSO-d$_6$, 400 MHz) δ ppm: 2.11.2.18 (m, 1 H), 2.57-2.64 (m, 1 H), 2.61 (s, 3 H), 2.93 (s, 3 H), 3.31 (t, J=8.0 Hz, 2 H), 3.35-3.41 (m, 1 H), 3.45-3.51 (m, 1 H), 3.82 (t, J=8.0 Hz, 2 H), 4.94 (t, J=7.6 Hz, 1 H), 6.92 (t, J=2.0 Hz, 1 H), 7.09 (d, J=8.8 Hz, 2 H), 7.52 (s, 1 H), 7.63 (s, 1 H), 7.98 (d, J=8.8 Hz, 2 H); ESI MS m/z (relative intensities): 494.1 (M+H)$^+$ (100%), 516 (M+Na)$^+$, (10%); UPLC Purity: 90.12%, Ret.time: 2.985 min.

EXAMPLE 76

(S)-Ethyl 5-chloro-2-(3-(4-(5-methyl-1,3,4-oxadiazol-2-yl)phenoxy)-5-((1-methyl-2-oxo pyrrolidin-3-yl)oxy)benzamido)thiazole-4-carboxylate $^1$H NMR (DMSO-d$_6$, 400 MHz) δ ppm: 1.28 (t, J=7.2 Hz, 3 H), 1.96-1.99 (m, 1 H), 2.56 (s, 3 H), 2.58-2.59 (m, 1 H), 2.79 (s, 3 H), 3.32-3.43 (m, 2 H), 4.29 (q, J=7.2 Hz, 2 H), 5.14 (t, J=7.2 Hz, 1 H), 7.11 (t, J=2.4 Hz, 1 H), 7.25 (d, J=6.8 Hz, 2 H), 7.44 (t, J=1.6 Hz, 1 H), 7.64 (t, J=1.6 Hz, 1 H), 7.99 (d, J=6.8 Hz, 2 H), 13.28 (bs, 1 H); ESI MS m/z (relative intensities): 597.9 (M+H)$^+$ (100%); UPLC Purity: 97.3%, Ret.time: 4.52 min.

EXAMPLE 77

(R)-3-(4-(5-methyl-1,3,4-oxadiazol-2-yl)phenoxy)-5-((1-methyl-2-oxopyrrolidin-3-yl)oxy)-N-(thiazol-2-yl)benzamide To a stirring solution of (R)-(+)-3-[4-(5-Methyl-1,3,4-oxadiazol-2-yl)phenoxy]-5-[(1-methyl-2-oxo-pyrrolidin-3-yl)oxy]benzoic acid (0.2 g) (Intermediate 18) in dry DCM in single necked round bottomed flask fitted with stop cock with N$_{2(g)}$ balloon, N,N'-dimethylamino pyridine (0.060 g) followed by EDCI. HCl (0.23 g) were added at room temperature. After stirring at the same temperature for 15 min, 2-aminothiazole (0.054 g) was added and stirring was continued for 16 h. Progress of reaction was monitored by TLC. After completion, reaction mixture was diluted with DCM (20 mL), washed with dil HCl (5 mL, 0.05 N), saturated sodium bicarbonate solution, water and brine, dried over anhydrous sodium sulphate, filtered and concentrated under vacuum to get crude brown solid (0.080 g). The crude brown solid was purified by solvent trituration.

$^1$H NMR (CDCl$_3$, 400 MHz) δ ppm: 2.15-2.20 (m, 1 H), 2.55-2.60 (m, 1 H), 2.62 (s, 3 H), 2.93 (s, 3 H), 3.38-3.43 (m, 1 H), 3.47-3.53 (m, 1 H), 4.91 (t, J=6.8 Hz, 1 H), 6.99 (d, J=8.8 Hz, 2 H), 7.10-7.14 (m, 2 H), 7.23-7.26 (m, 1 H), 7.36 (s, 1 H), 7.43 (s, 1 H), 8.03 (d, J=8.8 Hz, 2 H), 10.75 (bs, 1 H); ESI MS m/z (relative intensities): 492.1 (M+H)$^+$ (100%), 514.0 (M+Na)$^+$ (20%); UPLC Purity: 95.25%, Ret.time: 3.578 min. Chiral Purity by HPLC: 95.93%, Ret.time: 14.17 min. % ee: 91.86%

Intermediate 18

(R)-(+)-3-[4-(5-Methyl-1,3,4-oxadiazol-2-yl)phenoxy]-5-[(1-methyl-2-oxo-pyrrolidin-3-yl)oxy]benzoic acid Sodium hydroxide (pallets, 0.35 g) was added To a stirring mixture of (R)-(+)-Methyl 3-[4-(5-methyl-1,3,4-oxadiazol-2-yl)phenoxy]-5-[(1-methyl-2-oxo-pyrrolidin-3-yl) oxy] benzoate (1.1 g) (Intermediate 19) in MeOH:H$_2$O (1:1) at room temperature. The reaction was monitored by TLC. After completion, methanol was evaporated from the reaction mixture and water was added. The aqueous layer was washed with EtOAc, acidified with dil. HCl (0.05 N) to obtain solid. The solid obtained was filtered, washed with water, dried under suction or vacuum to get pure white solid (0.76 g).

$^1$H NMR (DMSO-d$_6$, 400 MHz) δ ppm: 1.92-1.99 (m, 1 H), 2.62 (s, 3 H), 2.58-2.66 (m, 1 H), 3.31 (s, 3 H), 3.32-3.40 (m, 2 H), 5.12 (t, J=7.2 Hz, 1 H), 7.08 (s, 1 H), 7.14 (s, 1 H), 7.23 (d, J=8.8 Hz, 2 H), 7.40 (s, 1 H), 7.99 (d, J=8.8 Hz, 2 H); ESI MS m/z (relative intensities): 410.1 (M+H)$^+$ (65%), 410.1 (M+H)$^+$ (100%); UPLC Purity: 96.95%, Ret. time: 3.12 min. Chiral Purity by HPLC: 89.04%, Ret. Time: 48.15 min.

Intermediate 19

(R)-(+)-Methyl 3-[4-(5-methyl-1,3,4-oxadiazol-2-yl) phenoxy]-5-[(1-methyl-2-oxo-pyrrolidin-3-yl)oxy] benzoate Sodium hydride suspension (0.16 g, 50%) was added to a stirring solution of (R)-(+)-Methyl 3-(4-(5-methyl-1,3,4-oxadiazol-2-yl)phenoxy)-5-((2-oxopyrrolidin-3-yl)oxy)benzoate (1.5 g) (Intermediate 20) in dry DMF taken in a round bottomed flask fitted with anhydrous CaCl$_2$ guard tube, at room temperature. The reaction mixture was stirred at the same temperature for 15 min. Methyl iodide (0.20 mL) was added and stirred till the reaction completed. The reaction mixture was quenched with ice-water, extracted with DCM. All organic layers were combined, washed with water, brine, dried over sodium sulphate, filtered and concentrated in vacuum to get the thick liquid product. The liquid was triturated with EtOAc:hexane to get the white solid product (1.2 g).

$^1$H NMR (DMSO-d$_6$, 400 MHz) δ ppm: 1.95-1.98 (m, 1 H), 2.51-2.55 (m, 1 H), 2.56 (s, 3 H), 2.88 (s, 3 H), 3.29-3.34 (m, 1 H), 3.37-3.40 (m, 1 H), 3.81 (s, 3 H), 5.12 (t, J=7.2 Hz, 1 H), 7.13-7.17 (m, 2 H), 7.24 (d, J=8.8 Hz, 2H), 7.41 (s, 1 H), 7.99 (d, J=8.8 Hz, 2 H); ESI MS m/z (relative intensities): 423.9 (M+H)$^+$ (100%); UPLC Purity: 90.38%, Ret. time: 3.68 min.

Intermediate 20

(R)-(+)-Methyl 3-(4-(5-methyl-1,3,4-oxadiazol-2-yl) phenoxy)-5-((2-oxopyrrolidin-3-yl)oxy)benzoate To a stirring mixture of Methyl 3-hydroxy-5-[4-(5-methyl-1,3,4-oxadiazol-2-yl)phenoxy]benzoate (2.5 g) (Intermediate 7) and (S)-(−)-3-hydroxy-2-pyrrolidinone (Intermediate 17) (0.8 g) in dry THF (70 mL) taken in round bottomed flask fitted with anhydrous CaCl$_2$ guard tube, triphenyl phosphine (3.77 g) was added. Diisopropyl azodicarboxylate (DIAD) (2.1 mL) in dry THF (2 mL) was added drop wise to the above reaction mixture. The reaction was stirred at room temperature. Reaction was monitored by TLC for completion. After completion, reaction mixture was concentrated under vacuum to remove the solvents. Diluted with DCM and coated over silica gel and chromatographed to furnish the product as white solid (2 g).

$^1$H NMR (CDCl$_3$, 400 MHz) δ ppm: 2.23-2.30 (m, 1 H); 2.62 (s, 3 H), 2.64-2.71 (m, 1H), 3.40-3.46 (m, 1 H), 3.50-3.55 (m, 1 H), 3.89 (s, 3 H), 4.89 (t, J=7.6 Hz, 1 H), 6.99 (t, J=2.4 Hz, 1 H), 7.11 (d, J=8.8 Hz, 2 H), 7.36 (s, 1 H), 7.51 (s, 1 H), 8.03 (d, J=8.8 Hz, 2 H); ESI MS m/z (relative intensities): 410.1 (M+H)$^+$ (45%); UPLC Purity: 96.40%, Ret. time: 3.48 min. Chiral Purity by HPLC: 90.92%, Ret. Time: 48.36 min.

EXAMPLE 78

(R)-Ethyl 2-(3-(4-(5-methyl-1,3,4-oxadiazol-2-yl) phenoxy)-5-((1-methyl-2-oxopyrrolidin-3-yl)oxy) benzamido)thiazole-5-carboxylate $^1$H NMR (DMSO-d$_6$, 400 MHz) δ ppm: 1.28 (t, J=7.2 Hz, 3 H), 1.91-2.01 (m, 1 H), 2.56 (s, 3 H), 2.60-2.71 (m, 1 H), 2.78 (s, 3 H), 3.31-3.40 (m, 2 H), 4.28 (q, J=7.2 Hz, 2 H), 5.15 (t, J=7.6 Hz, 1 H) 7.12 (t, J=2 Hz, 1 H), 7.25 (d, J=7.2 Hz, 2 H), 7.44 (t, J=2.0 Hz, 1 H), 7.63 (s, 1 H), 8.01 (d, J=7.2 Hz, 2 H), 8.21 (s, 1 H), 13.13 (s, 1 H); ESI MS m/z (relative intensities): 563.9 (M+H)$^+$ (100%); UPLC Purity: 91.6%, Ret.time: 4.08 min.

EXAMPLE 79

(R)-Ethyl 2-(3-(4-(5-methyl-1,3,4-oxadiazol-2-yl) phenoxy)-5-((1-methyl-2-oxopyrrolidin-3-yl)oxy) benzamido)thiazole-4-carboxylate $^1$H NMR (DMSO-d$_6$, 400 MHz) δ ppm: 1.28 (t, J=7.2 Hz, 3 H), 1.91-2.01 (m, 1 H), 2.56 (s, 3 H), 2.60-2.66 (m, 1 H), 2.79 (s, 3 H), 3.31-3.41 (m, 2 H), 4.27 (q, J=7.2 Hz, 2 H), 5.15 (t, J=7.6 Hz, 1 H), 7.09 (t, J=2 Hz, 1 H), 7.25 (d, J=8.4 Hz, 2 H), 7.44 (t, J=1.6 Hz, 1 H), 7.65 (s, 1 H), 8.01 (d, J=8.8 Hz, 2 H), 8.12 (s, 1 H), 13.05 (bs, 1 H); ESI MS m/z (relative intensities): 563.9 (M+H)$^+$ (100%); UPLC Purity: 98.0%, Ret.time: 3.99 min.

EXAMPLE 80

(R)-Eethyl 5-chloro-2-(3-(4-(5-methyl-1,3,4-oxadiazol-2-yl)phenoxy)-5-((1-methyl-2-oxo-pyrrolidin-3-yl)oxy)benzamido)thiazole-4-carboxylate $^1$H NMR (DMSO-d$_6$, 400 MHz) δ ppm: 1.28 (t, J=7.2 Hz, 3 H), 1.96-1.99 (m, 1 H), 2.56 (s, 3 H), 2.58-2.59 (m, 1 H), 2.79 (s, 3 H), 3.32-3.43 (m, 2 H), 4.29 (q, J=7.2 Hz, 2 H), 5.14 (t, J=7.2 Hz, 1 H), 7.11 (t, J=2.4 Hz, 1 H), 7.25 (d, J=8.8 Hz, 2 H), 7.44 (t, J=1.6 Hz, 1 H), 7.64 (t, J=1.6 Hz, 1 H), 7.99 (d, J=8.8 Hz, 2 H), 13.28 (s, 1 H); ESI MS m/z (relative intensities): 598.0 (M+H)+ (100%); UPLC Purity: 96.7%, Ret.time: 4.53 min.

EXAMPLE 81

(R)-3-(4-(5-Methyl-1,3,4-oxadiazol-2-yl)phenoxy)-5-((1-methyl-2-oxopyrrolidin-3-yl)oxy)-N-(4-methylthiazol-2-yl)benzamide $^1$H NMR (DMSO-$d_6$, 400 MHz) δ ppm: 2.12-2.19 (m, 1 H), 2.28 (s, 3 H), 2.54-2.60 (m, 1 H), 2.62 (s, 3 H), 2.93 (s, 3 H), 3.34-3.42 (m, 1 H), 3.47-3.52 (m, 1 H), 4.89 (t, J=6.4 Hz, 1 H), 6.56 (d, J=1.2 Hz, 1 H), 7.00 (t, J=2 Hz, 1 H), 7.11 (d, J=8.8 Hz, 2 H), 7.16 (t, J=1.6 Hz, 1 H), 7.40 (t, J=1.6 Hz, 1 H), 8.01 (d, J=8.8 Hz, 2 H), 09.95 (bs, 1 H); ESI MS m/z (relative intensities): 505.9 (M+H)+, UPLC Purity: 97.96%, Ret.time: 3.75 min.

EXAMPLE 82

(R)-3-(4-(5-Methyl-1,3,4-oxadiazol-2-yl)phenoxy)-5-((1-methyl-2-oxopyrrolidin-3-yl)oxy)-N-(5-methylthiazol-2-yl)benzamide $^1$H NMR (DMSO-$d_6$, 400 MHz) δ ppm: 2.12-2.21 (m, 1 H), 2.36 (s, 3 H), 2.52-2.60 (m, 1 H), 2.61 (s, 3 H), 2.93 (s, 3 H), 3.36-3.42 (m, 1 H), 3.47-3.53 (m, 1 H), 4.90 (t, J=1.6 Hz, 1 H), 6.98 (m, 2 H), 7.11 (d, J=8.8, 2H), 7.22 (t, J=1.6 Hz, 1 H), 7.40° (t, J=2 Hz, 1 H), 8.00 (d, J=8.8 Hz, 2 H), 10.69 (bs, 1 H); ESI MS m/z (relative intensities): 505.9 (M+H)+ (100%); UPLC Purity: 98.56%, Ret.time: 3.75 min.

Testing of Compounds of the Invention Using In-Vitro Assay

The compound of the invention was incubated with glucokinase (GK) enzyme (0.2 units) for 10 minutes in assay buffer at 26° C. After incubation, addition of glucose-6-phosphate dehydrogenase (2.5 units), ATP (1 mM) and glucose (2.5 mM). Absorbance is measured at 340 nM for 15 minutes with 10 second interval using UV transparent plate in kinetic mode on Spectramax-190 at 30° C.

The results obtained from the above test using representative compounds of the formula (I) as the test compound are summarized in the following table 1:

TABLE 1

| Ex. No. | EC50 (μM) | % of GK activity wrt DMSO | | | |
|---|---|---|---|---|---|
| | | 0.1 uM | 1 uM | 5 uM | 10 uM |
| 1 | 0.021 | 275.8 | 308.7 | 315.9 | 308.7 |
| 2 | 0.04 | 204.6 | 226.7 | 232.9 | 235.9 |
| 3 | 0.196 | 185.9 | 283.8 | 312.5 | 316.5 |
| 4 | 0.32 | 148.44 | 272.9 | 330.5 | 321.7 |

TABLE 1-continued

| Ex. No. | EC50 (μM) | % of GK activity wrt DMSO | | | |
|---|---|---|---|---|---|
| | | 0.1 uM | 1 uM | 5 uM | 10 uM |
| 5 | | 113.67 | 159.48 | 287.46 | 329.22 |
| 6 | | 100.1 | 114.8 | 190.2 | 275.2 |
| 7 | | 164.3 | 313.6 | 356.4 | 347 |
| 8 | | 133.8 | 194.7 | 218 | 234.7 |
| 9 | | 167.5 | 291.6 | 344.8 | 346 |
| 10 | | 129.9 | 204 | 232.3 | 227.7 |
| 11 | | 101 | 109 | 130.5 | 148.1 |
| 12 | | 107 | 119 | 138.6 | 150.3 |
| 13 | 0.074 | 233.7 | 302.1 | 319.5 | 318.1 |
| 14 | | 271.2 | 297.8 | 288.5 | 267 |
| 15 | | 95.46 | 125.56 | 206.29 | 236.78 |
| 16 | | 106.39 | 168.72 | 258.61 | 279.59 |
| 17 | | 125.09 | 157.73 | 192.23 | 178.27 |
| 18 | | 125.38 | 201.48 | 253.06 | 279.96 |
| 19 | | 113.85 | 208.04 | 304.7 | 281.72 |
| 20 | | 121.03 | 188.08 | 208.16 | 196.21 |
| 21 | | 120.21 | 212.74 | 277.57 | 280.95 |
| 22 | | 163.28 | 283.1 | 347.4 | 320.19 |
| 23 | | 168.14 | 249.96 | 287.03 | 282.32 |
| 24 | | 145.95 | 147.45 | 172.69 | 188.52 |
| 25 | | 124.63 | 149 | 202.94 | 208.08 |
| 26 | | 109.37 | 204.67 | 338.92 | 357.07 |
| 27 | | 177.16 | 261.91 | 355.08 | 365.14 |
| 28 | | 131.25 | 248.3 | 335.61 | 337.73 |
| 29 | | 166.88 | 267.56 | 334.7 | 347.32 |
| 30 | | 125.52 | 249.11 | 370.37 | 385.58 |
| 31 | | 146.21 | 294.66 | 356.46 | 342.96 |
| 32 | | 186.81 | 303.85 | 366.49 | 381.89 |
| 33 | | 201.11 | 308.73 | 382.51 | 374.62 |
| 34 | | 182.48 | 350.46 | 396 | 337.42 |
| 35 | | 181 | 322.1 | 382.1 | 366.1 |
| 36 | | 133.1 | 176.9 | 253.6 | 224.7 |
| 37 | | 107 | 151.4 | 289.6 | 329.2 |
| 38 | | 150 | 205.3 | 251.5 | 255.5 |
| 39 | | 150.7 | 179 | 215.3 | 262 |
| 68 | 0.034 | 144.4 | 237.5 | 255.4 | 271.11 |
| 69 | | 116.7 | 170.1 | 249.2 | 255.3 |
| 70 | | 238.3 | 315.1 | 318.4 | 325.6 |
| 77 | 0.356 | 112.4 | 141.2 | 230.4 | 261.2 |

Accordingly, the compounds of the present invention have an excellent GK activating potency as indicated by GK activation at different concentrations as well as EC$_{50}$ as mentioned in the above table 1.

Testing of Compounds of the Invention Using In-Vivo Assay

The antihyperglycemic effect of compounds of the present invention was demonstrated by following in-vivo test.

Effect of Glucokinase Activators (GKAs) of the Present Invention on Glucose Reduction Determined by Oral Glucose Tolerence Test (OGTT):

Male C57 mice, aged 8-10 weeks were fasted overnight and subjected to the treatment of selected GK activator at time denoted as −30 min. At time 0 min, mice were given oral glucose load of 3 g/kg, and the glucose excursion was observed upto 120 min. The percentage change against the change in glucose levels of control are mentioned in the table 2.

TABLE 2

| | Overnight fasted OGTT | | | | |
|---|---|---|---|---|---|
| | % change in glucose levels Vs Control | | | | |
| | 0 min Vs −30 min | 30 min Vs −30 min | 60 min Vs −30 min | 120 min Vs −30 min | Mean |
| Ex. 1 | −32.7 ± 2.8 | 3.3 ± 9.7 | −39.5 ± 7.0 | −24.3 ± 9.0 | −23.3 |
| Ex. 2 | −34.5 ± 3.2 | −13.5 ± 8.8 | −49.6 ± 11.2 | −53.2 ± 3.1 | −37.7 |
| Ex. 3 | −18.8 ± 5.8 | −4.1 ± 6.0 | −3.9 ± 4.3 | −15.8 ± 3.7 | −10.6 |
| Ex. 4 | −23.3 ± 3.1 | −22.1 ± 6.1 | −21.8 ± 5.9 | −16.7 ± 5.9 | −21.0 |

TABLE 2-continued

| | Overnight fasted OGTT | | | | |
|---|---|---|---|---|---|
| | % change in glucose levels Vs Control | | | | |
| | 0 min Vs −30 min | 30 min Vs −30 min | 60 min Vs −30 min | 120 min Vs −30 min | Mean |
| Ex. 37 | 11.9 ± 8.2 | −26.5 ± 12.8 | −43.5 ± 3.8 | −24.9 ± 5.3 | −17.0 |
| Ex. 68 | −46.7 ± 0.8 | −25.6 ± 7.2 | −51.5 ± 4.9 | −58.2 ± 6.7 | −46.6 |
| Ex. 69 | −58.6 ± 5.6 | −91.2 ± 1.3 | −84.4 ± 0.9 | −72.9 ± 5.6 | −75.2 |
| Ex. 77 | −4.8 ± 7.5 | −15.1 ± 6.6 | −13.9 ± 7.3 | −22.0 ± 3.3 | −11.2 |
| Ex. 13 | −38.7 ± 3.5 | −34.5 ± 9.3 | −48.2 ± 7.5 | −60.5 ± 4.5 | −45.5 |

The novel compounds of the present invention can be formulated into suitable pharmaceutically acceptable compositions by combining with suitable excipients by techniques and processes and concentrations as are well known.

The compounds of Formula (I) or pharmaceutical compositions containing them are useful as antidiabetic compounds suitable for humans and other warm blooded animals, and may be administered either by oral, topical or parenteral administration.

The novel compounds of the present invention can be formulated into suitable pharmaceutically acceptable compositions by combining with suitable excipients by techniques and processes and concentrations as are well known. Thus, a pharmaceutical composition comprising the compounds of the present invention may comprise a suitable binder, suitable bulking agent &/or diluent and any other suitable agents as may be necessary. Optionally, the pharmaceutical composition may be suitably coated with suitable coating agents.

The compounds of the present invention (1) are glucokinase activators and are useful in the treatment of disease states mediated by glucokinase, preferably diabetes and related disorders.

The quantity of active component, that is, the compounds of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

While the present invention has been described in terms of its specific embodiment, certain modifications and equivalents will be apparent to those skilled in the art and are intended to be included within the scope of the present invention.

We claim:
1. Compounds having the structure of Formula (I),

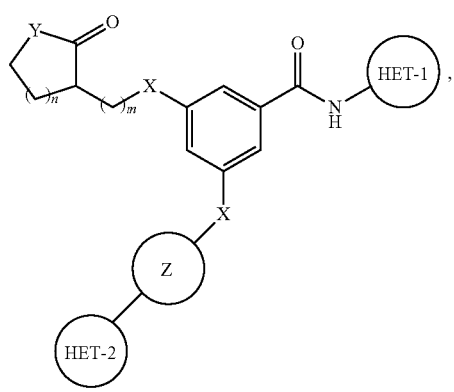

(I)

their pharmaceutically acceptable salts, pharmaceutically acceptable solvates, enantiomers, or diastereomers thereof, wherein X=O, $CH_2$, S; Y=O, $CH_2$, $CR^1R^2$, $NR^1$, $NCOR^1$; HET-1 is a 5- or 6-membered, C-linked heteroaryl ring containing a nitrogen atom in 2-position relative to the amide nitrogen to which the ring is attached and optionally containing 1 or 2 further ring heteroatoms independently selected from O, N and S, which ring is optionally substituted on available carbon, nitrogen and/or sulfur atom with one or more $R^3$; Ring 'Z' is selected from phenyl or 'HET-3', wherein 'HET-3' is a 5- or 6-membered heteroaryl or heterocyclic ring containing 1, 2 or 3 hetero atoms independently selected from O, S and N and wherein either the phenyl or the 'HET-3' independently is further substituted with one or more of $R^3$;

'Het-2' is selected from the following cyclic groups

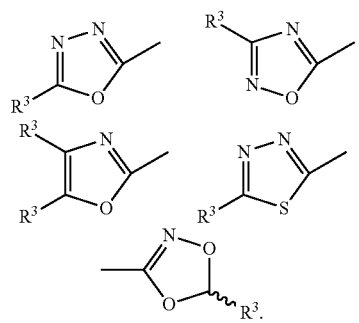

$R^3$ at each occurrence is independently selected from hydrogen, halogen, cyano, optionally substituted groups selected from —$NR^1R^2$, $C_{(1-6)}$ alkyl, $C_{(2-6)}$ alkenyl, $C_{(2-6)}$ alkyne, $C_{(1-6)}$ haloalkyl, $C_{(1-6)}$ alkoxy, $C_{(1-6)}$ haloalkoxy, —$C_{(3-6)}$ cycloalkyl, —$(CH_2)_p$—$COOR^1$, —$(CH_2)_p$—$CONR^1R^2$, $CONHR^1$, perfluoroalkyl, $C_{(1-4)}$ alkoxyalkyl, aryl, arylalkyl, amino, aminoalkyl, alkylamino, alkylaminoalkyl, alkyl$C_{(1-4)}$alkoxy, wherein each of $R^3$ when further substituted, the substituents are independently selected from amino, halo, cyano, nitro, hydroxyl, alkoxy groups; and $R^1$ and $R^2$ at each occurrence is independently selected from hydrogen, halogen, amino, cyano, nitro, optionally substituted groups selected from $C_{(1-4)}$ alkyl, $C_{(2-4)}$ alkenyl, $C_{(2-4)}$ alkynyl, $C_{(1-4)}$ alkoxy, $C_{(1-4)}$ haloalkyl groups or alternatively, when possible, $R^1$ & $R^2$ together with the atom to which they are attached may further form a cycloalkyl or heterocyclic ring containing heteroatoms selected from O, S and N; m=0, 1, 2; n=0, 1, 2; p=0, 1, 2.

2. The compounds as claimed in claim 1, wherein
'HET-1' is a 5- or 6-membered, C-linked heteroaryl ring containing a nitrogen atom in 2-position relative to the amide nitrogen to which the ring is attached, and optionally containing 1 or 2 further ring heteroatoms independently selected from O, N and S, which ring is optionally substituted with one or more R³; ring 'Z' is phenyl, substituted with 1 to 3 substituents selected from R³; X=O, CH₂, S; Y=O, CH₂, CR¹R²,NR¹, NCOR¹; and R³, R¹, R², m, n, p, and 'HET-2' are as defined earlier.

3. The compounds as claimed in claim 1, wherein 'HET-1' is a 5- or 6-membered, C-linked heteroaryl ring containing a nitrogen atom in 2-position relative to the amide nitrogen to which the ring is attached, and optionally containing 1 or 2 further ring heteroatoms independently selected from O, N and S, which ring is optionally substituted with one or more R³; ring 'Z' represents 'HET-3', optionally substituted with 1 to 3 substituents selected from R³; X=O, CH₂, S; Y=O, CH₂, CR¹R², NR¹, NCOR¹; and R³, R¹, R², m, n, p, and 'HET-2' are as defined earlier.

4. The compounds as claimed in claim 1, wherein 'HET-1' is a 5- or 6-membered, C-linked heteroaryl ring containing a nitrogen atom in 2-position relative to the amide nitrogen to which the ring is attached and optionally containing 1 or 2 further ring heteroatoms independently selected from O, N and S, which ring is optionally substituted with one or more R³; ring 'Z' is phenyl, substituted with 1 to 3 substituents selected from R³; X=O, CH₂, S; Y=O, CH₂, CR¹R², N NR¹, NCOR¹; and R³, R¹, R², m, n, and p are as defined earlier.

5. The compounds as claimed in claim 1, wherein 'HET-1' is a 5- or 6-membered, C-linked heteroaryl ring containing a nitrogen atom in 2-position relative to the amide nitrogen to which the ring is attached and optionally containing 1 or 2 further ring heteroatoms independently selected from O, N and S, which ring is optionally substituted with one or more R³; ring 'Z' represents 'HET-3', optionally substituted with 1 to 3 substituents selected from R³; X=O, CH₂, S; Y=O, CH₂, CR¹R², NR¹, NCOR¹; and R³, R¹, R², m, n, p are as defined earlier.

6. The compounds of claim 1, wherein
X=O, CH₂;
Y=O, CH₂, CR¹R²;
ring 'Z' represents phenyl, substituted with 1 to 3 substituents selected from R³; and
HET-1, HET-2, R¹, R², R³, m, n, and p are as defined earlier.

7. The compounds of claim 1, wherein R³ at each occurrence independently represents hydrogen, halo, C₍₁₋₆₎ alkyl, C₍₂₋₆₎alkenyl, and aryl groups.

8. The compounds of claim 1, wherein the substituents on R³ are selected from halo, nitro, hydroxyl, and alkoxy groups.

9. The compounds of claim 1, wherein R¹ and R² at each occurrence is independently selected from hydrogen, halo, hydroxyl, cyano, C₍₁₋₄₎alkyl, and C₍₁₋₄₎alkoxy groups.

10. The compounds of Formula (I) of claim 1, wherein
X=O, CH₂;
Y=O, CR¹R², NR¹;
ring 'Z' is phenyl, substituted with 1 to 3 substituents selected from R³, wherein R³ at each occurrence independently represents hydrogen, halo, C₍₁₋₆₎alkyl groups;
R¹ and R² at each occurrence is independently selected from hydrogen, halo, hydroxyl, cyano, C₍₁₋₄₎alkyl, C₍₁₋₄₎alkoxy;
m=0, 1;
n=0, 1;
p=0, 1;

HET-2 is selected from the following cyclic groups,

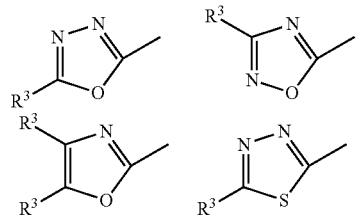

and all other symbols are as defined earlier.

11. A compound selected from the group consisting of:
3-(4-(5-Methyl-1,3,4-oxadiazol-2-yl)phenoxy)-5-((1-methyl-2-oxopyrrolidin-3-yl)methoxy) -N-(thiazol-2-yl)benzamide;
3-(4-(5-Methyl-1,3,4-oxadiazol-2-yl)phenoxy)-5-((1-methyl-2-oxopyrrolidin-3-yl)methoxy)-N-(4-methylthiazol-2-yl)benzamide;
3-(4-(5-Methyl-1,3,4-oxadiazol-2-yl)phenoxy)-5-((1-methyl-2-oxopyrrolidin-3-yl)methoxy)-N-(5-methylthiazol-2-yl)benzamide;
N-(5-Chlorothiazol-2-yl)-3-(4-(5-methyl-1,3,4-oxadiazol-2-yl)phenoxy)-5-((1-methyl-2-oxopyrrolidin-3-yl)methoxy)benzamide;
N-(5-Fluorothiazol-2-yl)-3-(4-(5-methyl-1,3,4-oxadiazol-2-yl)phenoxy)-5-((1-methyl-2-oxopyrrolidin-3-yl)methoxy)benzamide;
Ethyl 4-(hydroxymethyl)-2-(3-(4-(5-methyl-1,3,4-oxadiazol-2-yl)phenoxy)-5-((1-methyl-2-oxopyrrolidin-3-yl)methoxy)benzamido)thiazole-5-carboxylate;
Ethyl 2-(3-(4-(5-methyl-1,3,4-oxadiazol-2-yl)phenoxy)-5-((1-methyl-2-oxopyrrolidin-3-yl)methoxy)benzamido)thiazole-5-carboxylate;
Ethyl 4-(methoxymethyl)-2-(3-(4-(5-methyl-1,3,4-oxadiazol-2-yl)phenoxy)-5-((l-methyl-2-oxopyrrolidin-3-yl)methoxy)benzamido)thiazole-5-carboxylate;
Ethyl 2-(2-(3-(4-(5-methyl-1,3,4-oxadiazol-2-yl)phenoxy)-5-((1-methyl-2-oxopyrrolidin-3-yl)methoxy)benzamido)thiazol-4-yl)acetate;
2-(2-(3-(4-(5-Methyl-1,3,4-oxadiazol-2-yl)phenoxy)-5-((1-methyl-2-oxopyrrolidin-3-yl)methoxy)benzamido)thiazol-4-yl)acetic acid;
N-(4-(2-Amino-2-oxoethyl)thiazol-2-yl)-3-(4-(5-methyl-1,3,4-oxadiazol-2-yl)phenoxy)-5-((l-methyl-2-oxopyrrolidin-3-yl)methoxy)benzamide;
N-(4-(2-(diethylamino)-2-oxoethyl)thiazol-2-yl)-3-(4-(5-methyl-1,3,4-oxadiazol-2-yl)phenoxy)-5-((1-methyl-2-oxopyrrolidin-3-yl)methoxy)benzamide;
3-(4-(5-Methyl-1,3,4-oxadiazol-2-yl)phenoxy)-5-((1-methyl-2-oxopyrrolidin-3-yl)methoxy)-N-(4-(2-oxo-2-(piperidin-1-yl)ethyl)thiazol-2-yl)benzamide;
3-(4-(5-Methyl-1,3,4-oxadiazol-2-yl)phenoxy)-5-((1-methyl-2-oxopyrrolidin-3-yl)methoxy)-N-(4-(2-(4-methylpiperazin-1-yl)-2-oxoethyl)thiazol-2-yl)benzamide;
3-(4-(5-Methyl-1,3,4-oxadiazol-2-yl)phenoxy)-5-((1-methyl-2-oxopyrrolidin-3-yl)methoxy)-N-(4-(2-morpholino-2-oxoethyl)thiazol-2-yl)benzamide;
3-(4-(5-Methyl-1,3,4-oxadiazol-2-yl)phenoxy)-5-((1-methyl-2-oxopyrrolidin-3-yl)methoxy)-N-(pyrazin-2-yl)benzamide;
Methyl 6-(3-(4-(5-methyl-1,3,4-oxadiazol-2-yl)phenoxy)-5-((1-methyl-2-oxopyrrolidin-3-yl)methoxy)benzamido)nicotinate;
N-(Benzo[d]thiazol-2-yl)-3-(4-(5-methyl-1,3,4-oxadiazol-2-yl)phenoxy)-5-((1-methyl-2-oxopyrrolidin-3-yl)methoxy)benzamide;

N-(1H-Indazol-4-yl)-3-(4-(5-methyl-1,3,4-oxadiazol-2-yl)phenoxy)-5-((1-methyl-2-oxopyrrolidin-3-yl)methoxy)benzamide;

N-(5,5-Dimethyl-4-oxo-4,5-dihydrothiazol-2-yl)-3-(4-(5-methyl-1,3,4-oxadiazol-2-yl)phenoxy)-5-((1-methyl-2-oxopyrrolidin-3-yl)methoxy)benzamide;

3-(4-(5-Methyl-1,3,4-oxadiazol-2-yl)phenoxy)-5-((1-methyl-2-oxopyrrolidin-3-yl)methoxy)-N-(1H-pyrazol-3-yl)benzamide;

3-(4-(5-Methyl-1,3,4-oxadiazol-2-yl)phenoxy)-N-(5-methyl-1,3,4-thiadiazol-2-yl)-54(1-methyl-2-oxopyrrolidin-3-yl)methoxy)benzamide;

N-(5-Cyclopropyl-1,3,4-thiadiazol-2-yl)-3-(4-(5-methyl-1,3,4-oxadiazol-2-yl)phenoxy)-5-((1-methyl-2-oxopyrrolidin-3-yl)methoxy)benzamide;

N-(5-Cyclopropyl-1,3,4-thiadiazol-2-yl)-3-(4-(3-methyl-1,2,4-oxadiazol-5-yl)phenoxy)-5-((1-methyl-2-oxopyrrolidin-3-yl)methoxy)benzamide;

3-(4-(3-Methyl-1,2,4-oxadiazol-5-yl)phenoxy)-5-((1-methyl-2-oxopyrrolidin-3-yl)methoxy)-N-(thiazol-2-yl)benzamide;

3-(4-(3-Methyl-1,2,4-oxadiazol-5-yl)phenoxy)-5-((1-methyl-2-oxopyrrolidin-3-yl)methoxy)-N-(4-methylthiazol-2-yl)benzamide;

3-(4-(3-Methyl-1,2,4-oxadiazol-5-yl)phenoxy)-5-((1-methyl-2-oxopyrrolidin-3-yl)methoxy)-N-(5-methylthiazol-2-yl)benzamide;

N-(5-Chlorothiazol-2-yl)-3-(4-(3-methyl-1,2,4-oxadiazol-5-yl)phenoxy)-5-((1-methyl-2-oxopyrrolidin-3-yl)methoxy)benzamide;

N-(5-Fluorothiazol-2-yl)-3-(4-(3-methyl-1,2,4-oxadiazol-5-yl)phenoxy)-5-((1-methyl-2-oxopyrrolidin-3-yl)methoxy)benzamide;

3-(4-(3-Ethyl-1,2,4-oxadiazol-5-yl)phenoxy)-5-((1-methyl-2-oxopyrrolidin-3-yl)methoxy)-N-(thiazol-2-yl)benzamide;

3-(4-(3-Ethyl-1,2,4-oxadiazol-5-yl)phenoxy)-5-((1-ethyl-2-oxopyrrolidin-3-yl)methoxy)-N-(thiazol-2-yl)benzamide;

3-(4-(3-Ethyl-1,2,4-oxadiazol-5-yl)phenoxy)-5-((1-isopropyl-2-oxopyrrolidin-3-yl)methoxy)-N-(thiazol-2-yl)benzamide;

3-(4-(1,2,4-Oxadiazol-5-yl)phenoxy)-5-((1-methyl-2-oxopyrrolidin-3-yl)methoxy)-N-(thiazol-2-yl)benzamide;

3-(4-(1,2,4-Oxadiazol-5-yl)phenoxy)-5-((1-methyl-2-oxopyrrolidin-3-yl)methoxy)-N-(5-methylthiazol-2-yl)benzamide;

3-(4-(1,2,4-Oxadiazol-5-yl)phenoxy)-N-(5-fluorothiazol-2-yl)-5-((1-methyl-2-oxopyrrolidin-3-yl)methoxy)benzamide;

3-(4-(5-Methyl-1,3,4-oxadiazol-2-yl)phenoxy)-54 1-methyl-2-oxopyrrolidin-3-yloxy)-N-(thiazol-2-yl)benzamide;

3-(4-(5-Methyl-1,3,4-oxadiazol-2-yl)phenoxy)-5-(1-methyl-2-oxopyrrolidin-3-yloxy)-N-(4-methylthiazol-2-yl)benzamide;

3-(4-(5-Methyl-1,3,4-oxadiazol-2-yl)phenoxy)-5-(1-methyl-2-oxopyrrolidin-3-yloxy)-N-(5-methylthiazol-2-yl)benzamide;

N-(5-Chlorothiazol-2-yl)-3-(4-(5-methyl-1,3,4-oxadiazol-2-yl)phenoxy)-5-(1-methyl-2-oxopyrrolidin-3-yloxy)benzamide;

N-(5-Fluorothiazol-2-yl)-3-(4-(5-methyl-1,3,4-oxadiazol-2-yl)phenoxy)-5-(1-methyl-2-oxopyrrolidin-3-yloxy)benzamide;

Ethyl 4-(methoxymethyl)-2-(3-(4-(5-methyl-1,3,4-oxadiazol-2-yl)phenoxy)-5-(1-methyl-2-oxopyrrolidin-3-yloxy)benzamido)thiazole-5-carboxylate;

Ethyl 2-(2-(3-(4-(5-methyl-1,3,4-oxadiazol-2-yl)phenoxy)-5-(1-methyl-2-oxopyrrolidin-3-yloxy)benzamido)thiazol-4-yl)acetate;

2-(2-(3-(4-(5-Methyl-1,3,4-oxadiazol-2-yl)phenoxy)-5-(1-methyl-2-oxopyrrolidin-3-yloxy) benzamido)thiazol-4-yl)acetic acid;

N-(4-(2-Amino-2-oxoethyl)thiazol-2-yl)-3-(4-(5-methyl-1,3,4-oxadiazol-2-yl)phenoxy)-5-(1-methyl-2-oxopyrrolidin-3-yloxy)benzamide;

N-(4-(2-(Diethylamino)-2-oxoethyl)thiazol-2-yl)-3-(4-(5-methyl-1,3,4-oxadiazol-2-yl) phenoxy)-5-(1-methyl-2-oxopyrrolidin-3-yloxy)benzamide;

3-(4-(5-Methyl-1,3,4-oxadiazol-2-yl)phenoxy)-5-(1-methyl-2-oxopyrrolidin-3-yloxy)-N-(4-(2-oxo-2-(piperidin-1-yl)ethyl)thiazol-2-yl)benzamide;

3-(4-(5-Methyl-1,3,4-oxadiazol-2-yl)phenoxy)-5-(1-methyl-2-oxopyrrolidin-3-yloxy)-N-(4-(2-morpholino-2-oxoethyl)thiazol-2-yl)benzamide;

3-(4-(5-Methyl-1,3,4-oxadiazol-2-yl)phenoxy)-5-(1-methyl-2-oxopyrrolidin-3-yloxy)-N-(4-(2-(4-methylpiperazin-1-yl)-2-oxoethyl)thiazol-2-yl)benzamide;

3-(1-Ethyl-2-oxopyrrolidin-3-yloxy)-5-(4-(5-methyl-1,3,4-oxadiazol-2-yl)phenoxy)-N-(thiazol-2-yl)benzamide;

3-(1-Isopropyl-2-oxopyrrolidin-3-yloxy)-5-(4-(5-methyl-1,3,4-oxadiazol-2-yl)phenoxy)-N-(thiazol-2-yl)benzamide;

3-(4-(5-Ethyl-1,3,4-oxadiazol-2-yl)phenoxy)-5-(1-methyl-2-oxopyrrolidin-3-yloxy)-N-(thiazol-2-yl)benzamide;

N-(5,5-dimethyl-4-oxo-4,5-dihydrothiazol-2-yl)-3-(4-(5-methyl-1,3,4-oxadiazol-2-yl) phenoxy)-5-(1-methyl-2-oxopyrrolidin-3-yloxy)benzamide;

N-(Benzo[d]thiazol-2-yl)-3-(4-(5-methyl-1,3,4-oxadiazol-2-yl)phenoxy)-5-(1-methyl-2-oxopyrrolidin-3-yloxy)benzamide;

3-(4-(5-Methyl-1,3,4-oxadiazol-2-yl)phenoxy)-N-(5-methyl-1,3,4-thiadiazol-2-yl)-5-(1-methyl-2-oxopyrrolidin-3-yloxy)benzamide;

N-(5-Cyclopropyl-1,3,4-thiadiazol-2-yl)-3-(4-(5-methyl-1,3,4-oxadiazol-2-yl)phenoxy)-5-(1-methyl-2-oxopyrrolidin-3-yloxy)benzamide;

N-(1H-Indazol-4-yl)-3-(4-(5-methyl-1,3,4-oxadiazol-2-yl)phenoxy)-5-(1-methyl-2-oxopyrrolidin-3-yloxy) benzamide;

3-(4-(5-Methyl-1,3,4-oxadiazol-2-yl)phenoxy)-5-(1-methyl-2-oxopyrrolidin-3-yloxy)-N-(pyrazin-2-yl)benzamide;

Methyl 6-(3-(4-(5-methyl-1,3,4-oxadiazol-2-yl)phenoxy)-5-(1-methyl-2-oxopyrrolidin-3-yloxy)benzamido)nicotinate;

3-(4-(5-Ethyl-1,3,4-oxadiazol-2-yl)phenoxy)-5-(1-methyl-2-oxopyrrolidin-3-yloxy)-N-(thiazol-2-yl)benzamide;

3-(4-(5-Isopropyl-1,3,4-oxadiazol-2-yl)phenoxy)-5-(1-methyl-2-oxopyrrolidin-3-yloxy)-N-(thiazol-2-yl)benzamide;

3-(1-Ethyl-2-oxopyrrolidin-3-yloxy)-5-(4-(5-methyl-1,3,4-oxadiazol-2-yl)phenoxy)-N-(thiazol-2-yl)benzamide;

3-(4-(3-Methyl-1,2,4-oxadiazol-5-yl)phenoxy)-5-(1-methyl-2-oxopyrrolidin-3-yloxy)-N-(thiazol-2-yl)benzamide;

3-(4-(3-Methyl-1,2,4-oxadiazol-5-yl)phenoxy)-5-(1methyl-2-oxopyrrolidin-3-yloxy)-N-(4-methylthiazol-2-yl)benzamide;

3-(4-(3-Methyl-1,2,4-oxadiazol-5-yl)phenoxy)-5-(1-methyl-2-oxopyrrolidin-3-yloxy)-N-(5-methylthiazol-2-yl)benzamide;

N-(5-Chlorothiazol-2-yl)-3-(4-(3-methyl-1,2,4-oxadiazol-5-yl)phenoxy)-5-(1-methyl-2-oxopyrrolidin-3-yloxy)benzamide;

N-(5-Fluorothiazol-2-yl)-3-(4-(3-methyl-1,2,4-oxadiazol-5-yl)phenoxy)-5-(1-methyl-2-oxopyrrolidin-3-yloxy)benzamide;

N-(Benzo [d] thiazol-2-yl)-3-(4-(3-methyl-1,2,4-oxadiazol-5-yl)phenoxy)-5 - (1-methyl-2-oxopyrrolidin-3-yloxy)benzamide;

3-(4-(3-Methyl-1,2,4-oxadiazol-5-yl)phenoxy)-N-(5-methyl-1,3,4-thiadiazol-2-yl)-5-(1-methyl-2-oxopyrrolidin-3-yloxy)benzamide;

N-(5-Cyclopropyl-1,3,4-thiadiazol-2-yl)-3-(4-(3-methyl-1,2,4-oxadiazol-5-yl)phenoxy)-5-(1-methyl-2-oxopyrrolidin-3-yloxy)benzamide; 1 3-(4-(3-Methyl-1,2,4-oxadiazol-5-yl)phenoxy)-5-(1-methyl-2-oxopyrrolidin-3-yloxy)-N-(1H-pyrazol-3-yl)benzamide;

3-(4-(3-Methyl-1,2,4-oxadiazol-5-yl)phenoxy)-N-(1-methyl-1H-pyrazol-3-yl)-5-(1-methyl -2-oxopyrrolidin-3-yloxy)benzamide;

3-(4-(1H-Imidazol-2-yl)phenoxy)-5-(1-methyl-2-oxopyrrolidin-3-yloxy)-N-(thiazol-2-yl)benzamide;

3-(4-(1-Methyl-1H-imidazol-2-yl)phenoxy)-5-(1-methyl-2-oxopyrrolidin-3-yloxy)-N-(thiazol-2-yl)benzamide;

3-(4-(1H-Benzo[d]imidazol-2-yl)phenoxy)-5-(1-methyl-2-oxopyrrolidin-3-yloxy)-N-(thiazol-2-yl)benzamide;

3-(4-(1-Methyl-1H-benzo[d]imidazol-2-yl)phenoxy)-5-(1-methyl-2-oxopyrrolidin-3-yloxy) -N-(thiazol-2-yl)benzamide;

3-(4-(4,5-Dihydro-1H-imidazol-2-yl)phenoxy)-5- (1-methyl-2-oxopyrrolidin-3-yloxy)-N-(thiazol-2-yl)benzamide;

3-(1-Methyl-2-oxopyrrolidin-3-yloxy)-5-(4-(1-methyl-4,5-dihydro-1H-imidazol-2-yl)phenoxy)-N-(thiazol-2-yl)benzamide;

3-(4-Cyanophenoxy)-5-(1-methyl-2-oxopyrrolidin-3-yloxy)-N-(thiazol-2-yl)benzamide;

3-(1-Methyl-2-oxopyrrolidin-3-yloxy)-5-(4-(oxazol-2-yl)phenoxy)-N-(thiazol-2-yl)benzamide;

3-(4-(1,3 -Dimethyl-1H-1,2,4-triazol-5-yl)phenoxy)-5-(1-methyl-2-oxopyrrolidin-3-yloxy) -N-(thiazol-2-yl)benzamide;

(S)-3-(4-(5-Methyl-1,3,4-oxadiazol-2-yl)phenoxy)-5-((2-oxopyrrolidin-3-yl)oxy)-N-(thiazol -2-yl)benzamide;

(R)-3-(4-(5 -Methyl-1,3,4-oxadiazol-2-yl)phenoxy)-5-((2-oxopyrrolidin-3-yl)oxy)-N -(thiazol-2-yl)benzamide;

(S)-N-(Benzo [d] thiazol-2-yl)-3-(4-(5-methyl-1,3,4-oxadiazol-2-yl)phenoxy)-5-((2-oxopyrrolidin-3-yl)oxy)benzamide;

(R)-N-(Benzo[d]thiazol-2-yl)-3-(4-(5-methyl-1,3,4-oxadiazol-2-yl)phenoxy)-5-((2-oxopyrrolidin-3-yl)oxy)benzamide;

(R)-3-(4-(5 -Methyl-1,3,4-oxadiazol-2-yl)phenoxy)-N-(4-methylthiazol-2-yl)-5-((2-oxopyrrolidin-3-yl)oxy)benzamide;

(S)-3-(4-(5-Methyl-1,3,4-oxadiazol-2-yl)phenoxy)-N-(4-methylthiazol-2-yl)-5-((2-oxopyrrolidin-3-yl)oxy)benzamide;

(R)-3-(4-(5 -Methyl-1,3,4-oxadiazol-2-yl)phenoxy)-N-(5-methylthiazol-2-yl)-5-((2-oxopyrrolidin-3-yl)oxy)benzamide;

(S)-3-(4-(5-Methyl-1,3,4-oxadiazol-2-yl)phenoxy)-N-(5-methylthiazol-2-yl)-5-((2-oxopyrrolidin-3-yl)oxy)benzamide;

(R)-3-(4-(5 -Methyl-1,3,4-oxadiazol-2-yl)phenoxy)-5-((2-oxopyrrolidin-3-yl)oxy)-N-(4-phenylthiazol-2-yl)benzamide;

(S)-3-(4-(5-Methyl-1,3,4-oxadiazol-2-yl)phenoxy)-5-((2-oxopyrrolidin-3-yl)oxy)-N-(4-phenylthiazol-2-yl)benzamide;

(R)-Ethyl 2-(3-(4-(5-methyl-1,3,4-oxadiazol-2-yl)phenoxy)-5-((2-oxopyrrolidin-3-yl)oxy)benzamido)thiazole-4-carboxylate;

(S)-Ethyl 2-(3 -(4-(5-methyl-1,3,4-oxadiazol-2-yl)phenoxy)-5-((2-oxopyrrolidin-3-yl)oxy)benzamido)thiazole-4-carboxylate;

3-(4-(1,3 -Dimethyl-1H-1,2,4-triazol-5-yl)phenoxy)-5-(1-methyl-2-oxopyrrolidin-3-yloxy)-N-(thiazol-2-yl)benzamide;

3-(4-(1,3-Dimethyl-1H-1,2,4-triazol-5-yl)phenoxy)-5-(1-methyl-2-oxopyrrolidin-3-yloxy)-N-(4-methylthiazol-2-yl)benzamide;

3-(4-(1,3-Dimethyl-1H-1,2,4-triazol-5-yl)phenoxy)-5-(1-methyl-2-oxopyrrolidin-3-yloxy)-N-(5-methylthiazol-2-yl)benzamide;

N- (5-Chlorothiazol-2-yl)-3- (4-(1,3-dimethyl-1H-1,2,4-triazol-5-yl)phenoxy)-5-(1-methyl-2-oxopyrrolidin-3-yloxy)benzamide;

3-(4-(1,3 -Dimethyl-1H-1,2,4-triazol-5-yl)phenoxy)-N-(5-fluorothiazol-2-yl)-5-(1 -methyl-2-oxopyrrolidin-3-yloxy)benzamide;

3-(4-(1,3 -Dimethyl-1H-1,2,4-triazol-5-yl)phenoxy)-5-(1-ethyl-2-oxopyrrolidin-3-yloxy)-N-(thiazol-2-yl)benzamide;

3-(4-(1,3 -Dimethyl-1H-1,2,4-triazol-5-yl)phenoxy)-5-(1-isopropyl-2-oxopyrrolidin-3-yloxy)-N-(thiazol-2-yl)benzamide;

3-(4-(1,3 -Dimethyl-1H-1,2,4-triazol-5-yl)phenoxy)-N-(5,5-dimethyl-4-oxo-4,5-dihydrothiazol-2-yl)-5 -(1-methyl-2-oxopyrrolidin-3-yloxy)benzamide;

N-(Benzo[d]thiazol-2-yl)-3-(4-(1,3-dimethyl-1H-1,2,4-triazol-5-yl)phenoxy)-5-(1 -methyl-2-oxopyrrolidin-3-yloxy)benzamide;

3-(4-(1,3 -Dimethyl-1H-1,2,4-triazol-5-yl)phenoxy)-N-(1H-indazol-4-yl)-54 1-methyl-2-oxopyrrolidin-3-yloxy)benzamide;

(S)-3-(4-(5-Methyl-1,3,4-oxadiazol-2-yl)phenoxy)-5-((1-methyl-2-oxopyrrolidin-3-yl)oxy)-N-(thiazol-2-yl)benzamide;

(R)-3-(4-(5 -Methyl-1,3,4-oxadiazol-2-yl)phenoxy)-5-((1-methyl-2-oxopyrrolidin-3-yl)oxy)-N-(thiazol-2-yl)benzamide;

(S)-3-(4-(5-Methyl-1,3,4-oxadiazol-2-yl)phenoxy)-5-((1-methyl-2-oxopyrrolidin-3-yl)oxy)-N-(5-methylthiazol-2-yl)benzamide;

(R)-3-(4-(5 -Methyl-1,3,4-oxadiazol-2-yl)phenoxy)-5-((1-methyl-2-oxopyrrolidin-3-yl)oxy)-N-(5-methylthiazol-2-yl)benzamide;

(S)-3-(4-(5-Methyl-1,3,4-oxadiazol-2-yl)phenoxy)-5-((1-methyl-2-oxopyrrolidin-3-yl)oxy)-N-(4-methylthiazol-2-yl)benzamide;

(R)-3-(4-(5 -Methyl-1,3,4-oxadiazol-2-yl)phenoxy)-5-((1-methyl-2-oxopyrrolidin-3-yl)oxy)-N-(4-methylthiazol-2-yl)benzamide;

(S)-3-(4-(5-Ethyl-1,3,4-oxadiazol-2-yl)phenoxy)-5-((1-methyl-2-oxopyrrolidin-3-yl)oxy)-N-(thiazol-2-yl)benzamide;

(R)-3-(4-(5-Ethyl-1,3,4-oxadiazol-2-yl)phenoxy)-5-((1-methyl-2-oxopyrrolidin-3-yl)oxy)-N-(thiazol-2-yl)benzamide;

(S)-3-(4-(5-Isopropyl-1,3,4-oxadiazol-2-yl)phenoxy)-5-((1-methyl-2-oxopyrrolidin-3-yl)oxy)-N-(thiazol-2-yl)benzamide;

(R)-3-(4-(5-Isopropyl-1,3,4-oxadiazol-2-yl)phenoxy)-5-((1-methyl-2-oxopyrrolidin-3-yl)oxy)-N-(thiazol-2-yl)benzamide;

(S)-3-(4-(5-Isopropyl-1,3,4-oxadiazol-2-yl)phenoxy)-5-((1-methyl-2-oxopyrrolidin-3-yl)oxy)-N-(5-methylthiazol-2-yl)benzamide;

(R)-3-(4-(5-Isopropyl-1,3,4-oxadiazol-2-yl)phenoxy)-5-((1-methyl-2-oxopyrrolidin-3-yl)oxy)-N-(4-methylthiazol-2-yl)benzamide;

(S)-3-(4-(5-Isopropyl-1,3,4-oxadiazol-2-yl)phenoxy)-5-((1-methyl-2-oxopyrrolidin-3-yl)oxy)-N-(4-methylthiazol-2-yl)benzamide;

(S)-3-((1-Ethyl-2-oxopyrrolidin-3-yl)oxy)-5-(4-(5-methyl-1,3,4-oxadiazol-2-yl)phenoxy)-N-(thiazol-2-yl)benzamide;

(R)-3-((1-Ethyl-2-oxopyrrolidin-3-yl)oxy)-5-(4-(5-methyl-1,3,4-oxadiazol-2-yl)phenoxy)-N-(thiazol-2-yl)benzamide;

(R)-3-((1-Ethyl-2-oxopyrrolidin-3-yl)oxy)-5-(4-(5-methyl-1,3,4-oxadiazol-2-yl)phenoxy)-N-(5-methylthiazol-2-yl)benzamide;

(S)-3-((1-Ethyl-2-oxopyrrolidin-3-yl)oxy)-5-(4-(5-methyl-1,3,4-oxadiazol-2-yl)phenoxy)-N-(5-methylthiazol-2-yl)benzamide;

(R)-3-((1-Ethyl-2-oxopyrrolidin-3-yl)oxy)-5-(4-(5-methyl-1,3,4-oxadiazol-2-yl)phenoxy)-N-(4-methylthiazol-2-yl)benzamide;

(S)-3-((1-Ethyl-2-oxopyrrolidin-3-yl)oxy)-5-(4-(5-methyl-1,3,4-oxadiazol-2-yl)phenoxy)-N-(4-methylthiazol-2-yl)benzamide, their pharmaceutically acceptable salts, pharmaceutically acceptable solvates, enantiomers, or diastereomers thereof.

12. A pharmaceutical composition comprising a therapeutically effective amount of a compound of claim 1 and optionally one or more pharmaceutically acceptable carriers, diluents or excipients.

13. A method of reducing blood glucose levels and increasing insulin secretion comprising administering to a patient in need thereof an effective amount of a compound of claim 1.

14. A method of treating type II diabetes comprising administering to a patient in need thereof an effective amount of a compound of claim 1.

* * * * *